US007968306B2

(12) United States Patent
Tsao et al.

(10) Patent No.: US 7,968,306 B2
(45) Date of Patent: Jun. 28, 2011

(54) METHOD FOR MEASURING ACTIVITY OF A SPECIFIC FRACTION OF ALBUMIN

(75) Inventors: Francis H. C. Tsao, Madison, WI (US); Keith C. Meyer, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 413 days.

(21) Appl. No.: 12/334,084

(22) Filed: Dec. 12, 2008

(65) Prior Publication Data

US 2009/0230325 A1 Sep. 17, 2009

Related U.S. Application Data

(63) Continuation-in-part of application No. 10/365,738, filed on Feb. 12, 2003, now Pat. No. 7,579,156.

(60) Provisional application No. 60/407,114, filed on Aug. 30, 2002, provisional application No. 60/357,188, filed on Feb. 13, 2002, provisional application No. 61/013,697, filed on Dec. 14, 2007.

(51) Int. Cl.
*G01N 1/00* (2006.01)
*G01N 33/53* (2006.01)

(52) U.S. Cl. ........ 435/7.21; 435/7.1; 436/501; 436/506; 436/518; 424/1.11; 424/1.21

(58) Field of Classification Search ........................ None
See application file for complete search history.

(56) References Cited

U.S. PATENT DOCUMENTS 4,444,879 A 4/1984 Foster et al.
4,668,623 A 5/1987 Kinnunen et al.
6,143,545 A 11/2000 Clausen et al.
6,180,596 B1 1/2001 Tsao

FOREIGN PATENT DOCUMENTS

EP 0037583 10/1981
JP 04-282391 10/1992
WO 00/67025 11/2000

OTHER PUBLICATIONS

Ascoli et al., Chirality 2006; 18; 9:667-679.
Balsinde et al., Annu. Rev. Pharmacol. Toxicol. 1999; 39: 175-189.
Banda et al., J. Biol. Chem. 1988; 263: 4481-4484.
Barton et al., J. Lab. Clin. Med. 1976; 88:423-426.
Blanque et al., General pharmacology 1998; 31:301-306.
Bligh et al., Can. J. Biochem. Physiol. 1955; 37:911-917.
Bruce et al., Am. Rev. Respir. Dis. 1985; 132: 529-535.
Buckland et al., Biochim. Biophys. Acta. 2000; 1488:71-82.
Cantin et al., Pediatr. Pulmon. 1989; 7: 12-17.
Carter et al., Adv. Protein Chem. 1994;45: 153-203.
Conricode et al., Biochim. Biophys. Acta. 1989; 1003:36-43.
Curry et al., Biochim. Biophys. Acta. 1999; 1441 : 131-140.
Davis et al., Am. J. Respir. Crit. Care Med. 1996; 154:1229-1256.
Dinges et al., Infect. Immun. 2001; 69: 7169-7172.
Doumas et al., Clin. Chim. Acta. 1971 ; 31:87-96.
Doweiko et al., Parenter Enternal Nutr. 1991; 15:212-214.
Endo et al., Brit. J. Pharmacol. 1999; 128:5-12.
Freedman et al., Proc. Natl. Acad. Sci. USA 1999; 96:13995-14000.
Funk CD. Science 2001; 294: 1871-1 875.
Galantai et al., Internat. J. Pharmaceu. 2000; 195:207-218.
Gilljam et al., Scan. J. Clin. Lab. Invest. 1986; 46:511-518.
Griffiths, Prostaglandins and inflammation. 3rd ed, 1999; 349-360.
Heinrikson et al., "A novel bifunctional mechanism of surface recognition by phospholipase A2" Biochem. Molec. Biol., and Physi. of Phospholipase A2 and Its Regulatory Factors. 1990; 297: 37-40.
Kim et al., J. Biol. Chem. 1997; 272:2542-2550.
Kramer et al., J. Biol. Chem. 1989; 264: 5768-5775.
Lai et al., Biochem. Biophys. Res. Comm. 1988; 157:488-493.
Martin et al., N. Engl. J. Med. 2003, 348:1546-1554.
Meshulam et al. J. Biol. Chem. 1992; 267: 21465-21470.
Miele et al., DNA Cell Biol. 1997; 16:749-759.
Maurer et al., Biophysic. J. 2001; 80:2310-2326.
Moraga et al., Arch. Biochem. Biophys. 2001; 386: 221-226.
Murakami et al., J. Biochem. 2002; 131:285-292.
Nevalainen et al., Biochim. Biophys. Acta. 2000; 1488:83-90.
Noel et al., J. Biol. Chem. 1972; 247:7391-7406.
Ostberg et al., J. Leukoc. Biol. 2000; 68:815-820.
Pappas et al., Chem-Biologic Interact 2003; 143-144:55-62.
Parviainen et al., Scand. J. Clin. Lab Invest. 1985; 45:561-564.
Seilhamer et al., J. Biol. Chem. 1989; 264:5335-5338.
Penrose et al., Leukotrienes: Biosynthetic pathways. Release, and receptor-mediated actions with relevance to disease states. In Inflammation: Basic Principles and Clinical Correlates, 3rd ed., 1999; 361-372.
Ruggiero et al., Mediators of inflammation 1993; 2:S43-S50.
Semple et al., Biochim. Biophys. Acta. 2001 ; 1510:152-166.
Tsao, Biochim. Biophys. Acta 1990; 1045:29-39.
Tsao et al., Clin. Chim. Acta. 2007; 379:119-126.
Tsao et al., Am. J. Respir. Cell. Mol. Biol. 1998; 18: 120-128.
Tsao et al., Biochim. Biophys. Acta 1991; 1081:141-150.
Valentin et al., Biochim. Biophys. Acta. 2000; 1488:59-70.
Vadas et al., Phospholipase A2 activation is the pivotal step in the effector pathway of inflammation. 1990; p. 83-101.
Vissers et al., J. Clin. Invest. 1988; 82:706-711.
Yedgar et al., Biochim. Biophys. Acta. 2000; 1488: 182-187.
Blanchard et al., Analytical Biochemistry 1994. 222:435-440.
Cantin et al., Pediatric Pulmonology 1991. 11:249-253.
El-Hariri et al., Journal of Pharm. Pharmacol. 1992. 44:651-654.
Fuller et al., Journal of Biological Chemistry 1972. 247:22, 7391-7406.

(Continued)

*Primary Examiner* — Lisa Cook
(74) *Attorney, Agent, or Firm* — Quarles & Brady, LLP

(57) ABSTRACT

Methods of measuring the SFA and $sPLA_2$ activities in a mammalian subject are provided. The methods include: providing a substrate comprising a fluorescently labeled carboxylic acid and a negatively charged phospholipid in an organic solvent such as ethanol, mixing the substrate with phospholipase $A_2$ and a biological sample from the subject, and detecting the fluorescence intensity change to determine the SFA and $sPLA_2$ activity in the sample. A decrease in SFA activity in the test sample as compared to the SFA activity in the control sample indicates that the subject has developed or is about to develop inflammation. An increase in $sPLA_2$ activity in the test sample as compared to the $sPLA_2$ activity in the control sample indicates that the subject has developed or is about to develop inflammation. Further disclosed is a kit for practicing the above methods.

20 Claims, 56 Drawing Sheets

OTHER PUBLICATIONS

Kisel et al., Biochemistry (Moscow) 2001. 66:2, 168-172.
Mustonen et al., Biochemistry 1993. 32:53-73.
Radvanyi et al., Anal Biochem. 1989. 177:1, 103-109.
Thuren et al., Clinical Chemistry 1985. 31:5, 714-717.
Tsao et al., Biochimica et Biophysica Acta. 1991. 1081:141-150.
Wang, Annu. Rev. Plant Mol. Biol. 2001. 52:211-231.
Wichmann et al., Chemical Communications 2001. 23:2500-2501.
Non Final Rejection from the USPTO mailed Feb. 23, 2007 in U.S. Appl. No. 10/365,738, filed Feb. 12, 2003.
Response filed Jun. 22, 2007, to USPTO Non Final Office Action mailed Feb. 23, 2007 in U.S. Appl. No. 10/365,738, filed Feb. 12, 2003.
Non Final Rejection from the USPTO mailed Sep. 13, 2007 in U.S. Appl. No. 10/365,738, filed Feb. 12, 2003.
Response filed Feb. 12, 2008, to USPTO Non Final Office Action mailed Sep. 13, 2007 in U.S. Appl. No. 10/365,738, filed Feb. 12, 2003.
Final Rejection from the USPTO mailed May 15, 2008 in U.S. Appl. No. 10/365,738, filed Feb. 12, 2003.
Response filed Nov. 17, 2008, to USPTO Final Office Action mailed May 15, 2008 in U.S. Appl. No. 10/365,738, filed Feb. 12, 2003.
Non Final Rejection from the USPTO mailed Dec. 15, 2008 in U.S. Appl. No. 10/365,738, filed Feb. 12, 2003.
Response filed Mar. 13, 2009, to USPTO Non Final Office Action mailed Dec. 15, 2008 in U.S. Appl. No. 10/365,738, filed Feb. 12, 2003.

Column
1: PLA2 (4)
2: PLA2 + CF BALF (4)
3: PLA2 + CF BALF (37 C 1 h) (4)
4: CF BALF (8)
5: PLA2 + NV BALF (4)

Column
1: PLA2 (5)
2: PLA2 + 25 ug CF BALF (heat) (3)
3: PLA2 + 50 ug CF BALF (heat) (3)
4: PLA2 + 100 ug CF BALF (heat) (3)
5: PLA2 + 100 ug CF BALF (no heat) (3)

Column
1: PLA2 (4)
2: PLA2 + CF BAL (4)
3: PLA2 + CF BAL + Annexin I (4)
4: PLA2 + CF BAL + 33 kD PLBP (4)
5: PLA2 + Annexin I (4)

A

B

METHOD FOR MEASURING ACTIVITY OF A SPECIFIC FRACTION OF ALBUMIN

CROSS-REFERENCE TO RELATED APPLICATIONS

This application is a continuation-in-part of U.S. Application No. 10/365,738 filed Feb. 12, 2003, now U.S. Pat. No. 7,579,156, entitled "Fluorescent phospholipase assay, phospholipase A2 inhibitor and stimulator, and the use thereof," currently pending, which claims the benefit of U.S. Provisional Application No. 60/407,114 filed Aug. 30, 2002 and U.S. Provisional Application No. 60/357,188 filed Feb. 13, 2002. This application also claims priority to U.S. Provisional Application No. 61/013,697, filed Dec. 14, 2007. All of these applications are hereby incorporated by reference herein in their entirety for all purposes.

STATEMENT REGARDING FEDERALLY-SPONSORED RESEARCH OR DEVELOPMENT

This invention was made with United States government support awarded by the following agency: NIH HL38744 and AI48624. The United States government has certain rights in this invention.

BACKGROUND OF THE INVENTION

The inflammatory response governs a wide range of illness from injury to infections and allergies. Initiating inflammation involves activating immune cells that trigger the phospholipase $A_2$ ($PLA_2$)-involved inflammatory processes. $PLA_2$ enzymes are a diverse family of enzymes that hydrolyze the sn-2 fatty acyl bond of phospholipids to produce, among other things, arachidonic acid (AA). They have a wide range of functions involving dietary phospholipid digestion, cellular phospholipid metabolism and turnover, membrane phospholipid remodeling, and critical roles in the inflammatory processes. $PLA_2$ enzymes are abundant in pancreatic juice and venoms of snakes and bees. They are also present in small amounts in many types of cells, including immune cells.

Three types of $PLA_2$ have been found in mammalian tissues: secretory $PLA_2$ ($sPLA_2$); cytosolic $PLA_2$ ($cPLA_2$); and the calcium-independent $PLA_2$ ($ciPLA_2$). $sPLA_2$ hydrolyzes the fatty acyl group at the sn-2 position of phospholipids at the air/water interface. They require millimolar calcium for their enzymatic reactions. $sPLA_2$ has been found to correlate with local and systemic inflammatory responses (1). For example, high levels of $sPLA_2$ have been found in the plasma of patients with acute sepsis, in synovial fluids from patients with arthritis, and in peritoneal fluids from patients with peritonitis.

$sPLA_2$ $sPLA_2$ enzymes have been implicated in human diseases, particularly in inflammatory diseases including COPD, cystic fibrosis and sepsis. However, the precise function of $sPLA_2$ is not clear. For instance, it is not clear how $sPLA_2$ enzymes exert their action on cells without indiscriminately destroying the cells.

At least ten $sPLA_2$ isoforms have been identified in humans, each with molecular weights around 14 kDa (2-4). The various isoforms of $sPLA_2$ have the same catalytic reactions in terms of phospholipid hydrolysis, i.e., hydrolyzing the fatty acyl group at the sn-2 position of phospholipids at the air/water interface. All $sPLA_2$ require millimolar calcium for enzymatic reactions and interact strongly with membranes containing anionic phospholipids but interact weakly with an interface composed of zwitterionic phosphatidylcholine (PC). Isoforms $sPLA_2$-IB and $sPLA_2$-IIA have been most extensively studied. $sPLA_2$-IB is considered a pancreatic enzyme whose function mainly involves digestion of dietary phospholipids. $sPLA_2$-IIA is a non-pancreatic enzyme and has been found to correlate with local and systemic inflammatory responses (5). $sPLA_2$-IIA is present in platelets and inflammatory cells including neutrophils and has been found in circulating blood and rheumatoid arthritic synovial fluid (5-7). The primary structure of human $sPLA_2$-IIA in platelets and synovial fluid has been determined and its gene cloned (7, 8).

Both $sPLA_2$-IB and $sPLA_2$-IIA have been implicated in human diseases, particularly in inflammatory diseases (9). High levels of $sPLA_2$-IIA have been found in the plasma of patients with acute sepsis, in synovial fluids from patients with arthritis, and in peritoneal fluids from patients with peritonitis (7, 9). $sPLA_2$-IIA may also act as an antibacterial agent to destroy bacteria during infection (10) due to the high cationic charge of $sPLA_2$-IIA (pI>10.5) that, in conjunction with bactericidal/permeability-increasing protein, enables $sPLA_2$-IIA to readily penetrate the cell wall of gram-negative bacteria and disrupt the anionic bacterial membrane.

Inhibiting $sPLA_2$ production has long been considered for therapeutic purposes (11). However, conventional drugs developed to inhibit $sPLA_2$ production or to restrain $PLA_2$ activity have serious side effects and sometimes even exacerbate the pathological conditions. This is, in part, because the complexity of $PLA_2$ enzymes makes drug design for detecting, treating and preventing inflammatory disease more difficult (12).

Conventionally, $PLA_2$ activity is measured by methods that involve the use of radioactive materials, which are inconvenient, time-consuming and biohazardous. A fluorescent liposome-based method has been described but the method is of low sensitivity in comparison to the radioactive methods (13). Another available fluorescence method incorporates fluorescent bis-BODIPY FL $C_{11}$-PC into the cellular membrane; however, it can only measure the $PLA_2$ activity indirectly (14). Other prior art methods include the pH titration method and the monolayer method, both of which require bulk volumes of reaction solutions, substrates and enzymes.

Therefore, a need exists for an efficient method for detecting, inhibiting and preventing $sPLA_2$ activity in a controlled, non-invasive manner to treat or prevent specific diseases.

Albumin

It has long been shown that some serum proteins including albumin can affect the activity of $sPLA_2$ in the in vitro assay. Albumin possesses dual effects on $sPLA_2$ activity, either stimulating or inhibiting $sPLA_2$ activity, depending on the assay conditions (15). It is generally believed that albumin stimulates $sPLA_2$ activity by removing the $PLA_2$-generated product lyso phospholipids, and inhibits $sPLA_2$ activity by binding the substrates, particularly with low concentrations of substrate liposomes, or removing negatively charged fatty acid from the enzyme/substrate interface (15).

Human serum albumin, a heart-shaped protein, consists of 585 amino acid residues with a calculated molecular weight of 66,439 and a pI value of 5.2. Albumin constitutes more than 60% of total blood plasma protein and plays important roles in fluid distribution throughout the body because of its colloidal properties, in acid-base physiology because of its unique composition and abundance, and in transport because of its high ligand-binding affinity. Although albumin is a monomeric protein, it is organized into three homologous domains (labeled I-III) and each domain is comprised of two sub-domains (A and B) which share common structural elements (16, 17). Its diverse bound-ligands and potential subjection to oxidation of its high content of disulphide bridges, albumin is considered to consist of heterogeneous forms that can be fractionated by passing through an anionic exchange column (18).

An array of different drugs have been found to bind to albumin with great affect on the pharmacokinetics of the drugs (19). Most of the associations between albumin and the bound-substances involve albumin's hydrophobic interaction property. In disease and malnutrition, the quantity and quality of albumin in the circulating blood are diminished. Changes in albumin quantity and quality not only affect on albumin's multiple roles, it may also have a consequence on drug transport efficacy and elimination mechanisms (20). Although the quantity of albumin in the plasma is widely determined by the bromocresol dye methods in clinical laboratories (21, 22), the quality change of albumin such as its binding or interaction properties with $PLA_2$ substrates or products in the blood cannot be simply determined.

Chronic Obstructive Pulmonary Disease

Chronic obstructive pulmonary disease (COPD) is a complex group of conditions associated with progressive airway obstruction and loss of lung function. Two major respiratory disorders associated with COPD—chronic bronchitis and emphysema—damage the lungs and make it difficult for air to move in and out of the lungs and for normal gas exchange to occur. Typical symptoms include shortness of breath, chronic cough and dyspnea on exertion. These symptoms worsen during periods of exacerbation that are typically caused by viral or bacterial infections but may be triggered for other reasons. Patients suffering from COPD often exhibit an increased level of $sPLA_2$-mediated inflammation.

Approximately eleven percent of the United States population, both diagnosed and undiagnosed, suffer from COPD. COPD is the fourth leading cause of death in the United States, and the cost of caring for patients with COPD is estimated to be as high as $40 billion annually (23).

Existing diagnostic methods for detecting and characterizing COPD include pulmonary function testing, pulse oximetry, radiological procedures and monitoring arterial blood gases. However, such testing only picks up relatively advanced cases of COPD and may not detect subtle abnormalities in individuals who have early or mild disease.

COPD treatments are not curative and are mainly focused on palliative care and preventing disease progression and complications. Current treatments include smoking cessation, prevention and management of infections, antioxidant supplementation, vaccinations, life style changes (i.e. avoiding exposure to inhaled irritants), pulmonary rehabilitation, medications (bronchodilators and corticosteroids) and lung transplantation.

Slowing disease progression is currently the objective of most treatments. However, successfully halting or slowing COPD progression is predicated upon early diagnosis and intervention. Currently, there is no reliable way to predict which individuals will develop COPD or which patients with COPD will become progressively worse and develop severe respiratory dysfunction. Efforts to develop a method to monitor the level of inflammation and oxidative stress present in patients with COPD, especially during periods of exacerbation, continue. These efforts involve invasive testing to monitor biomarkers such as carbon monoxide (CO) levels and noninvasive measures of CO, nitric oxide, and other oxidants and cytokines using expired breath condensates. A recent study of screening using an array of 36 systemic biomarkers for assessing COPD exacerbation found that those systemic biomarkers were not helpful in predicting exacerbation severity. The most selective biomarker was C-reactive protein (CRP). However, this was neither sufficiently sensitive nor specific by itself.

Therefore, a need exists for a non-invasive method of diagnosing and monitoring the subtle, sPLA2-mediated inflammation associated with COPD.

Cystic Fibrosis

Cystic fibrosis (CF) is a lung disease characterized by bacterial infection and intense inflammation that is often fatal. CF is caused by the defect of the gene encoding the CF transmembrane conductance regulator (CFTR), a large, membrane-spanning protein that regulates ion flux through the apical surfaces of epithelial cells. Pulmonary complications due to progressive bronchiectasis are the major cause of morbidity and mortality of the CF patients (24). Lower respiratory tract secretions of most CF patients contain high amounts of proteases, particularly the elastase from polymorphonuclear neutrophils (PMN). The abundant neutrophil elastase (NE) is thought to be a major cause of the epithelial tissue damage that leads to bronchiectasis and bronchial obstruction (25, 26).

It has long been recognized that elevating levels of AA in the lungs of patients with CF is linked to the pathogenesis of chronic lung inflammation (27). High arachidonic acid (AA) levels are also associated with phospholipids in lung tissue of CFTR gene knockout $cftr^{-/-}$-mice (28), and high levels of AA have been linked to low amounts of phospholipid-bound docosahexaenoic acid (DHA) in involved tissues (29). Epithelial cell lines with the deltaF508 mutation in their CFTR gene also released abnormally high levels of AA when induced by $Ca^{2+}$ (29).

Little is known about the regulation of the production of the high level of AA and the synthesis of the lipid mediators in the CF lung and airway. However, it appears that a cycle of enhanced LTB4 production from AA, chemoattraction of neutrophils, and intense inflammation due to neutrophil flux into lung tissue occurs and stimulates and sustains chronic inflammation (and progressive damage) in the CF lung. Also, the function of surfactant in the CF lung is impaired, and the surfactant phospholipid level is low. All these suggest that $PLA_2$-mediated inflammation may play a critical role in the CF lung injury.

To investigate whether the increase in AA in bronchial secretions of CF patients is due to the increase in $PLA_2$ activity, the inventors previously discovered that broncheal-veolar lavage fluid (BALF) from subjects with CF markedly induced $PLA_2$ activity in vitro (U.S. Pat. No. 6,180,596) (30). This revealed that there might be a $PLA_2$ stimulating factor in the BALFs of CF subjects.

Therefore, a need exists for a non-invasive method of diagnosing, monitoring and preventing the sPLA2-mediated inflammation associated with CF.

Sepsis

Infections are the most common causes of late deaths in trauma patients and a frequent cause of morbidity and mortality in hospitalized patients. Infected patients are at risk of developing sepsis, a systemic inflammatory response which causes a widespread and overwhelming activation of the immune system. Severe sepsis leads to tissue deterioration and multi-organ failure.

In the United States, sepsis is the 10th most common cause of death with the incidence of sepsis and sepsis-related deaths increasing by 1.5% per year (31). Recently, it was estimated that $16.7 billion in total national hospital cost in the United States is invoked by severe sepsis; this is based on 751,000 severe sepsis cases per year with 215,000 associated deaths annually. In the last decade, available therapies have been unsuccessful in significantly reducing the mortality rate from sepsis.

Early detection and diagnosis of sepsis is one of the most critical factors in determining patient outcome. Unfortunately, in early stages of sepsis, symptoms including $sPLA_2$-mediated inflammation are often subtle and non-specific, and warning signs, if present, can be easily overlooked or misdiagnosed. By the time the symptoms are obvious, treatment becomes much more challenging, and the likelihood of a successful outcome declines.

Thus, accurate early detection of evolving sepsis in the at-risk patient is a key to the successful treatment of sepsis and lowering the considerable mortality rates that are associated with sepsis. Therefore, a need exists for a non-invasive method of diagnosing, monitoring and preventing the $sPLA_2$-mediated inflammation associated with sepsis.

SUMMARY OF THE INVENTION

In one aspect, the present invention relates to a method for measuring the activity of a specific fraction of albumin (SFA) in a mammalian subject, which can be used to diagnose, monitor and prevent $PLA_2$-mediated inflammation. Specifically, the method of the present invention may be used for, among other applications, early detection of chronic obstructive pulmonary disease (COPD) and acute inflammation response to sepsis. The method includes providing a liposome comprising a fluorescently-labeled carboxylic acid and a negatively-charged phospholipid, mixing the liposome with phospholipase $A_2$ ($PLA_2$) and a biological sample from the subject, and measuring the change in fluorescence intensity to determine the SFA activity in the sample. The $PLA_2$ employed in the method may be a secretory $PLA_2$ ($sPLA_2$) such as human $PLA_2$-IIA (which can be recombinantly made, e.g., in bacteria) or a pancreatic $PLA_2$ (e.g., porcine pancreatic $PLA_2$-1B).

In another aspect, the present invention relates to a method for determining whether a mammalian subject has a decreased SFA activity. The method includes the steps of providing a liposome comprising a fluorescently-labeled carboxylic acid and a negatively-charged phospholipid, mixing the liposome with $PLA_2$ and a biological test sample from the subject, measuring a change in fluorescence intensity to determine the SFA activity in the sample, and comparing the SFA activity of the subject to an SFA activity from a control sample. The control sample can be a biological sample from the same subject measured at an earlier time and or a a normal range of SFA activity obtained from healthy subjects of the same species. The $PLA_2$ employed in the method may be a secretory $PLA_2$ ($sPLA_2$) such as human $PLA_2$-IIA (e.g., recombinant human $PLA_2$-IIA) or a pancreatic $PLA_2$ (e.g., porcine pancreatic $PLA_2$-1B).

In another aspect, the present invention relates to a kit for measuring SFA activity in a mammalian subject. The kit contains a fluorescently-labeled carboxylic acid, a negatively-charged phospholipid, $PLA_2$, and a positive control sample of SFA activity. Optionally, the kit may also include instructions for use on how to measure SFA activity in a biological sample from a mammalian subject according to the methods of the present invention described above.

Advantages

The present invention provides a novel, non-invasive method to detect inflammation in a mammalian subject. The method of the present invention therefore provides a sensitive and rapid test to allow the early detection of local or systemic inflammation, as well as facilitate monitoring of the development, progression, and severity of local or systemic inflammation. The assay may also facilitate timely interventions for at-risk patients such as those with CF, COPD or evolving infections.

Further, in comparison to the above-described prior art methods, the method of the present invention is advantageous in that it is simple, sensitive and involves no hazardous materials. Further still, the method of the present invention allows continuous recordation of the fluorescent intensity, making the result more reliable and can be readily applied to multi-well plates and thus adapted to high throughput applications.

Figure 3:
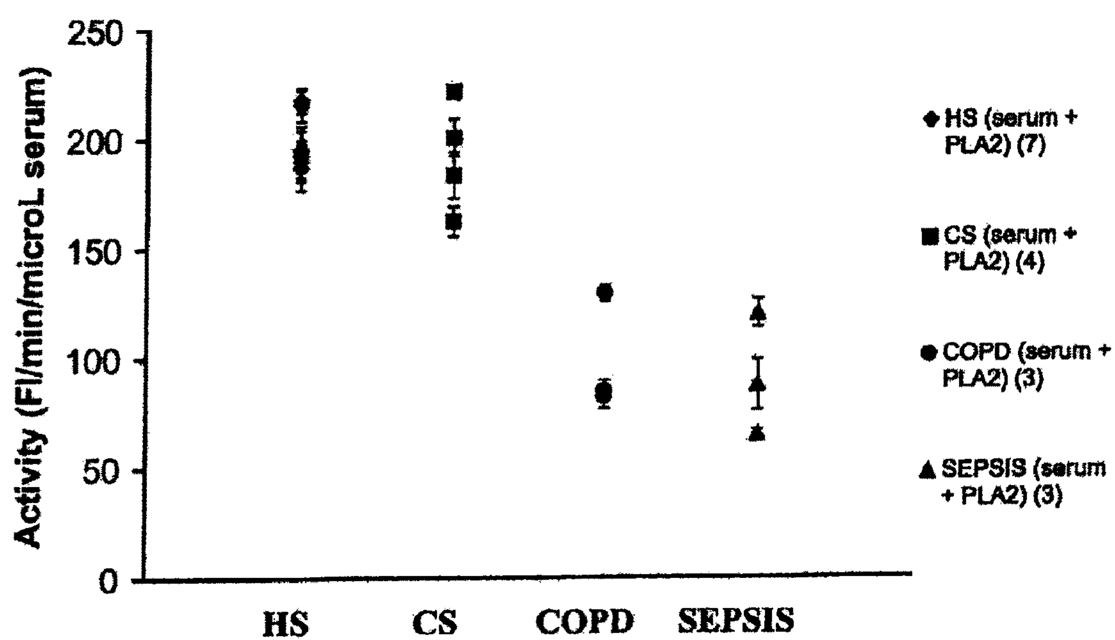
FIG. 3 illustrates exogenous $sPLA_2$-induced SFA activity in serum from HS, CS, COPD, and sepsis subjects. The SFA activity in the serum (1 μl) was determined in the presence of exogenous $sPLA_2$ (5 ng) in the reaction mixture. The activity was determined from the initial rate of the reaction curve after the curve is fitted to a second-order polynomial equation. The first-degree coefficient is taken to be the initial rate of reaction ($V_0$) and expressed as change in FI/min. The activity is expressed as mean±SEM (bar) from triplicate assays for each serum sample. Numbers of subjects in each group are shown in the parentheses. HS: healthy subjects, normal volunteers; CS: cigarette-smoking but otherwise healthy individuals; COPD: patients with chronic obstructive pulmonary disease; and SEPSIS: patients with acute respiratory decompensation requiring intensive care admission for treatment of pneumonia or sepsis at life trauma support center (TLC).
Figure 4:
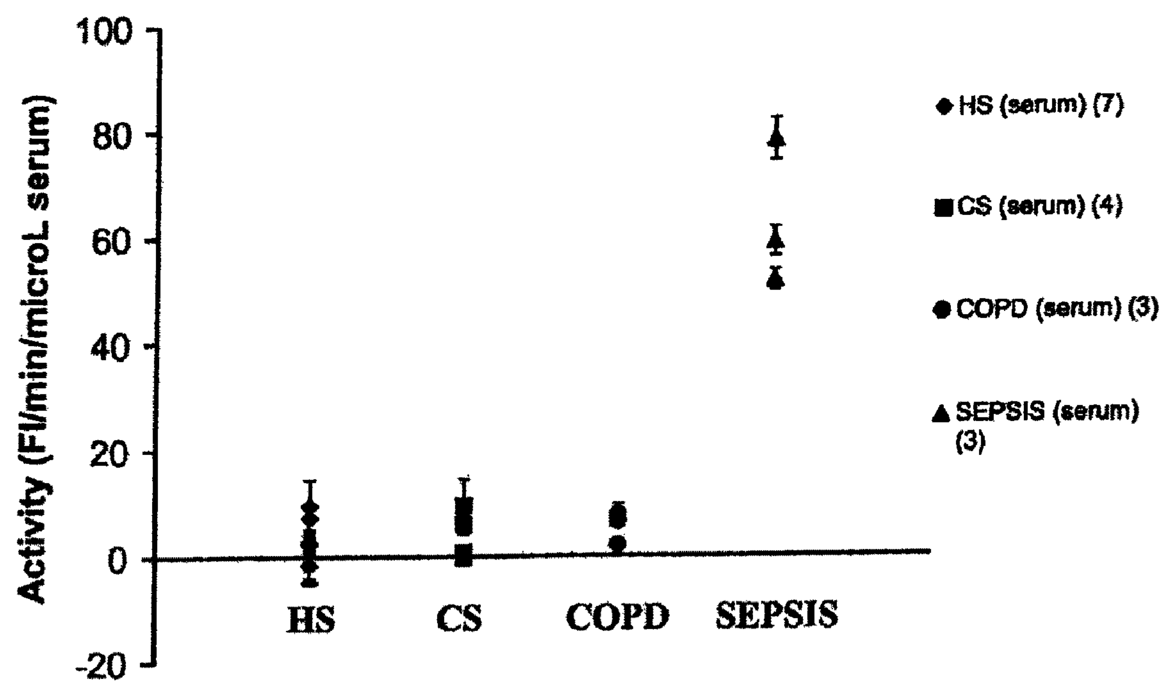
FIG. 4 illustrates endogenous $sPLA_2$-induced SFA activity in serum from HS, CS, COPD, and sepsis subjects. The activity in the serum (1 μl) was determined in the absence of exogenous $sPLA_2$ in the reaction mixture. The activity (FI/ min) is expressed as mean±SEM (bar) from triplicate assays for each serum sample. Numbers of subjects in each group are shown in the parentheses.
Figure 5:
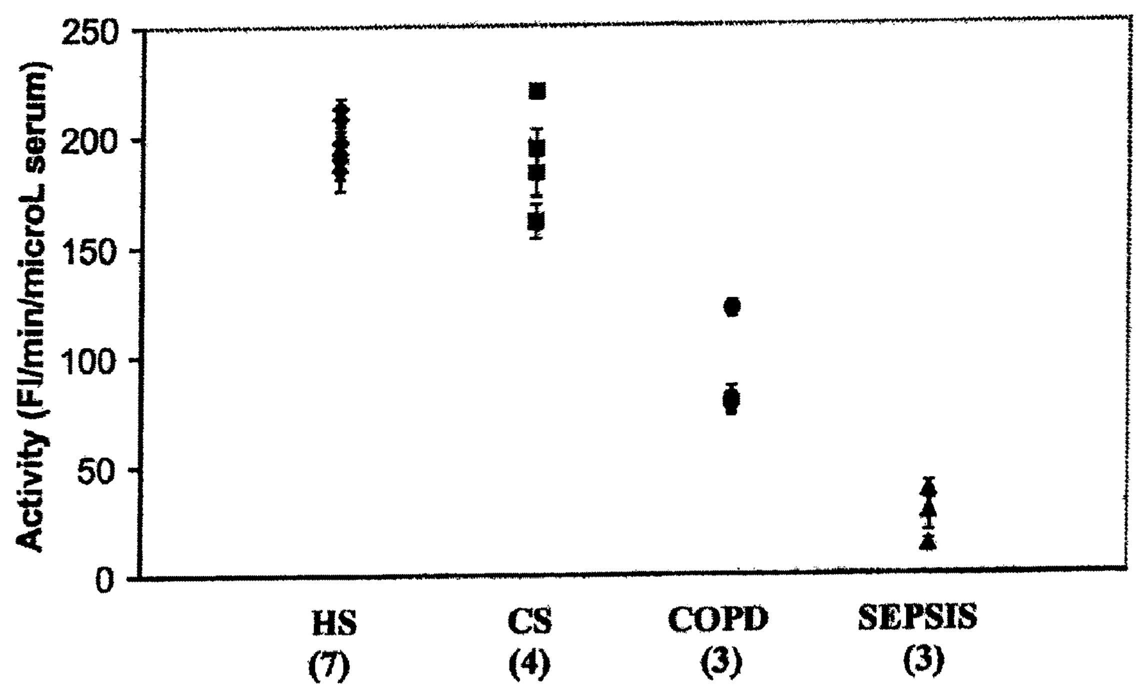

FIG. 5 illustrates SFA activity determined in 1 μl of serum from HS, CS, COPD, and sepsis subjects. The activity was determined by subtraction of endogenous $sPLA_2$-induced serum albumin activity (FIG. 4) from exogenous $sPLA_2$-induced serum albumin activity (FIG. 3). The results are expressed as means±SEM (bar) from triplicate assays for each serum sample. Numbers of subjects in each group are shown in the parentheses.

Figure 6:
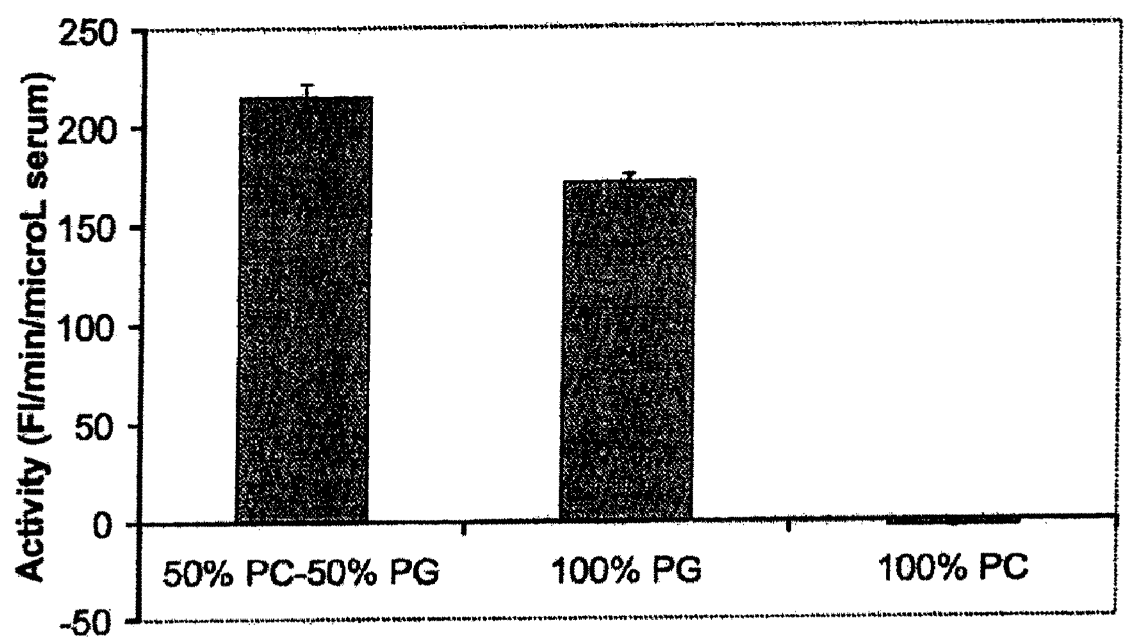

FIG. 6 illustrates the determination of $sPLA_2$-induced albumin-phospholipid interaction activity using liposomes with different phospholipid compositions. The reaction mixture contained 6 μg BODIPY-FA-labeled liposomes with different phospholipid compositions as shown in the figure, 1 μl human serum, and 5 ng $sPLA_2$ in 0.3 ml buffer (10 mM Tris-HCl, 10 mM $Ca^{2+}$, pH 7.4). The results are means±SEM (n=3).

Figure 7:
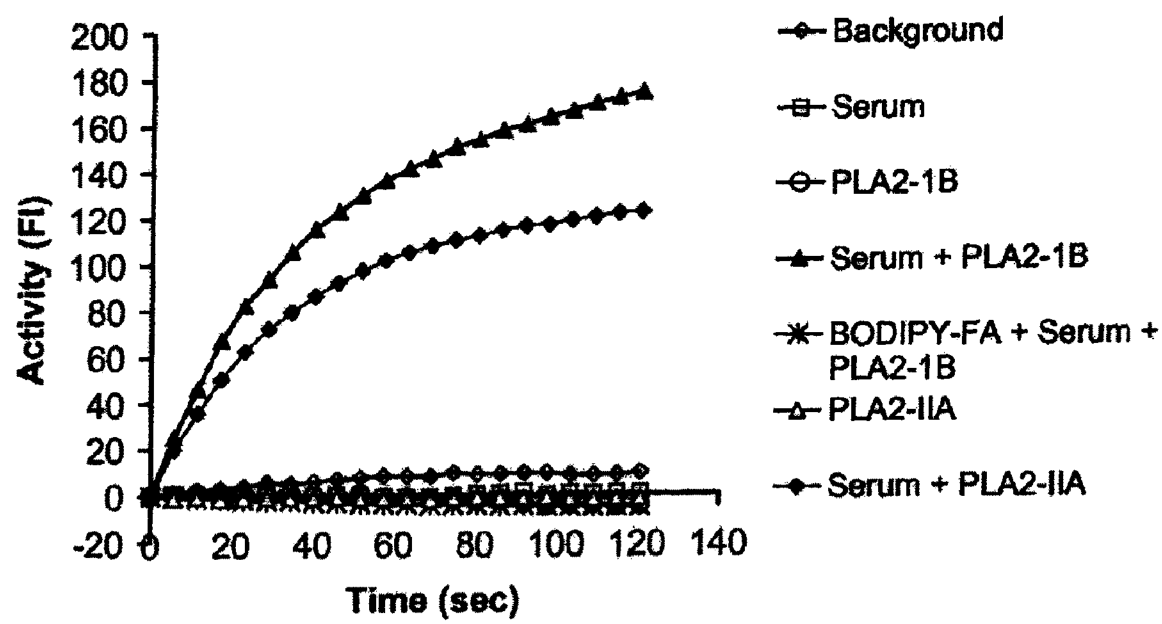

FIG. 7 is an example of microplate assay of determination of exogenous $sPLA_2$-induced serum albumin activity using DOPC-PG BODIPY-FA substrate in ethanol. Two different types of isoforms of $sPLA_2$, $PLA_2$-1B (porcine pancreatic protein) and $PLA_2$-IIA (recombinant human protein), were tested in this assay. The reaction mixture contained 6 μg BODIPY-FA-labeled 50% DOPC-50% PG prepared in ethanol, in the presence or absence of 1 μl human serum, or 5 ng $sPLA_2$ in 0.3 ml buffer (10 mM Tris-HCl, 10 mM $Ca^{2+}$, pH 7.4). The assay was conducted in a microplate well at room temperature for 3 min. Data from first 2 min reaction was plotted. The plot of BODIPY-FA was from the reaction containing the substrate of BODIPY-FA without DOPC and PG.

Figure 8A:
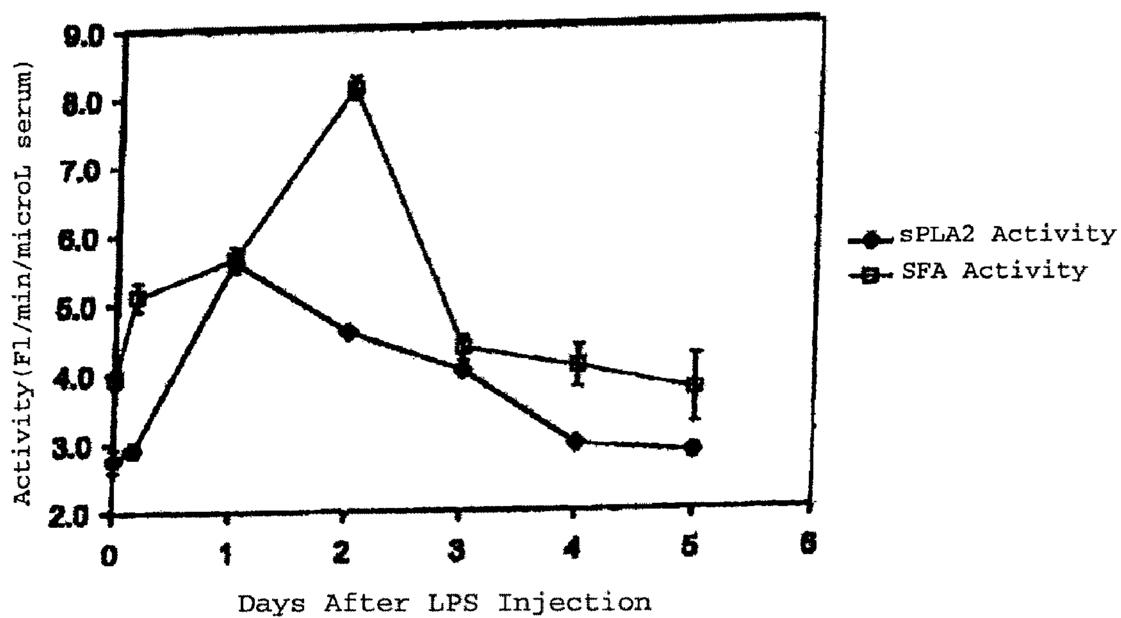

FIG. 8 illustrates (A) determining $sPLA_2$ activity and endogenous serum $sPLA_2$-induced SFA activity in the serum collected from rats prior and post peritoneal injection of LPS. Serum $sPLA_2$ activity was determined from the initial rate of each reaction using the microplate assay and 100% PG-BODIPY-PC in ethanol as substrate (example shown in FIG. 48). Serum SFA activity was determined from the initial rate of each reaction using the microplate assay and 50% DOPC-50% PG-BODIPY-FA in ethanol as substrate (example shown in FIG. 9). $sPLA_2$ and SFA activity was each determined in 1 μl of serum. Bars represent mean±SEM from triplicate assays. (B). Body weight of each rat was determined at the same time when the blood sample was collected as described in FIG. 8A. Bars represents mean±SEM from 3 rats.

Figure 9:
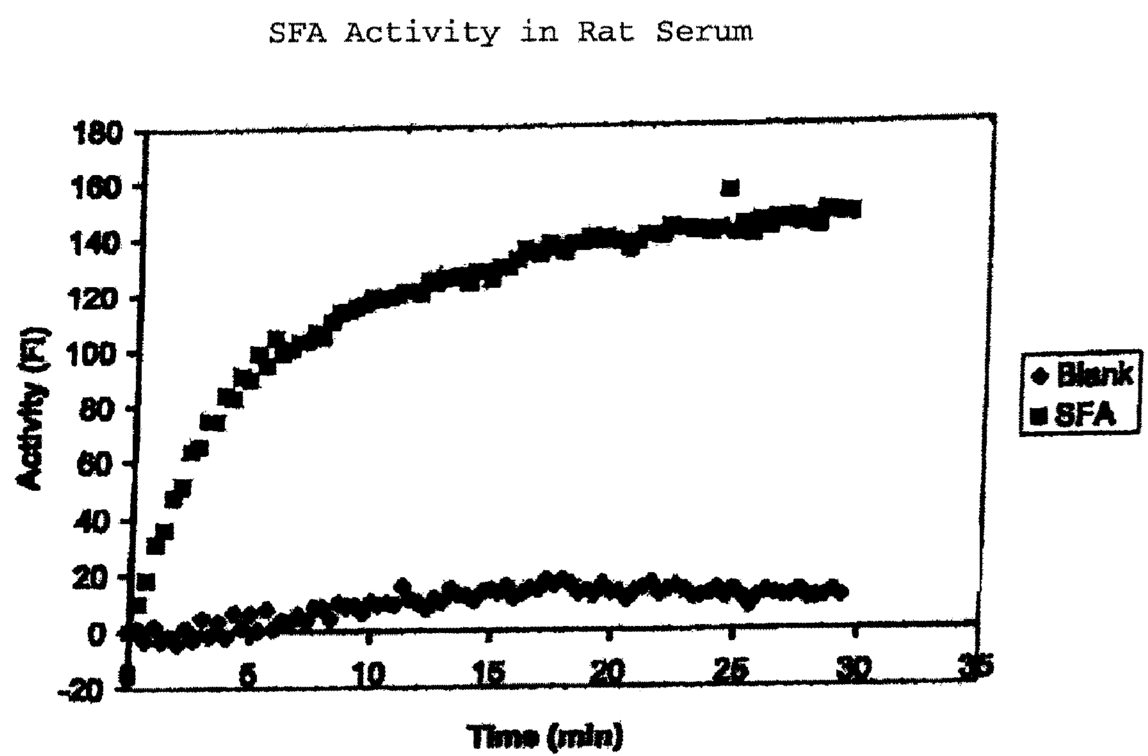

FIG. 9 illustrates an example of endogenous serum $sPLA_2$-induced SFA activity in rat serum with using 50% DOPC-50% PG-BODIPY-FA in ethanol as substrate. The serum sample used for SFA determination shown in this Figure was obtained from the rat 2 days after the rat received peritoneal injection of LPS. The amount of serum used in the assay was 1 μl. The activity time course profiles of serum $sPLA_2$ and SFA correlate well with the recovery of the rats following LPS injection. SFA activity peaked on day 2, the day the rats started to show recovery from LPS-induced illness. These results suggest that both serum $sPLA_2$ activity and SFA activity can be used as specific markers for assessing acute-phase response of inflammation and recovery.

Figure 10:
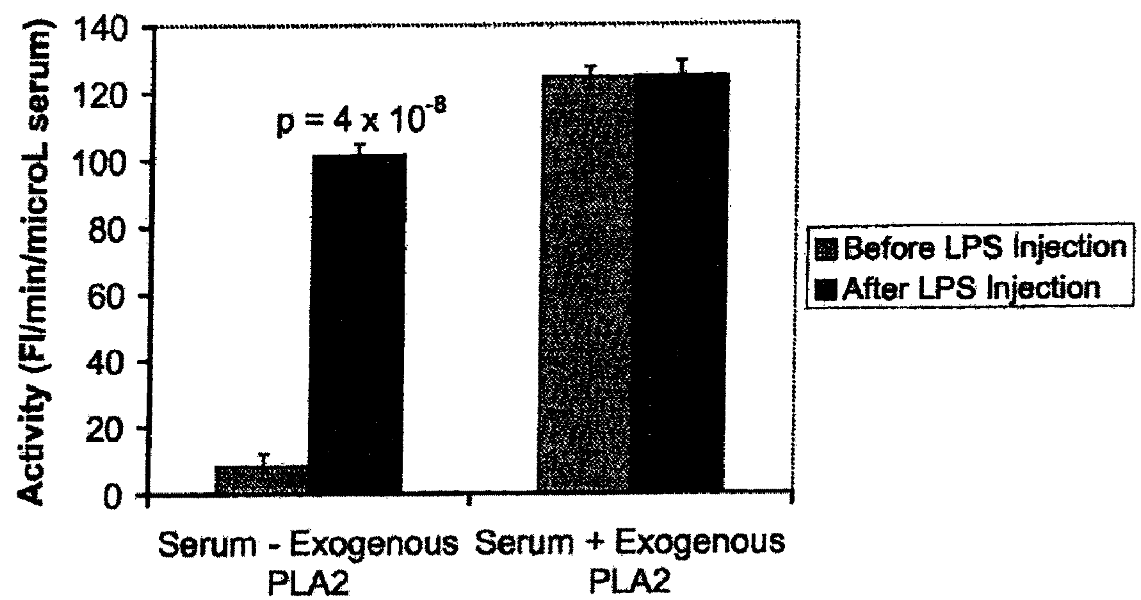

FIG. 10 illustrates exogenous $sPLA_2$-induced SFA activity in serum from rats before and after LPS injection. The assay was conducted in the absence (Serum−Exogenous $PLA_2$) and presence (Serum+Exogenous $PLA_2$) of pancreatic $sPLA_2$ (5 ng) in the reaction mixture containing DOPC-PG BODIPY FA liposomes as substrates. Five serum samples were collected from five rats before and after LPS injection; each assay was conducted in duplicate. The activity is expressed as mean±SEM.

Figure 11:
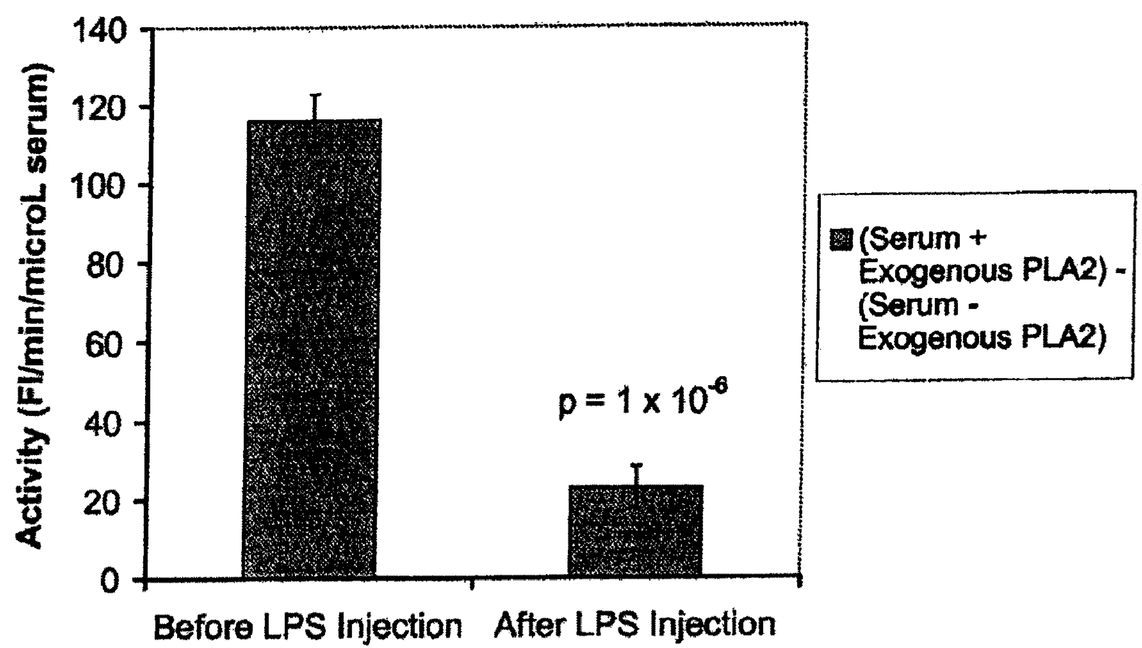

FIG. 11 illustrates SFA activity determined in the serum from rats before and after LPS injection. The activity was determined from the difference of the FI between the assay of (Serum+Exogenous $PLA_2$) and (Serum−Exogenous $PLA_2$). Five serum samples were collected from five rats before and after LPS injection; each assay was conducted in duplicate. The activity is expressed as mean+SEM.

Figure 12:
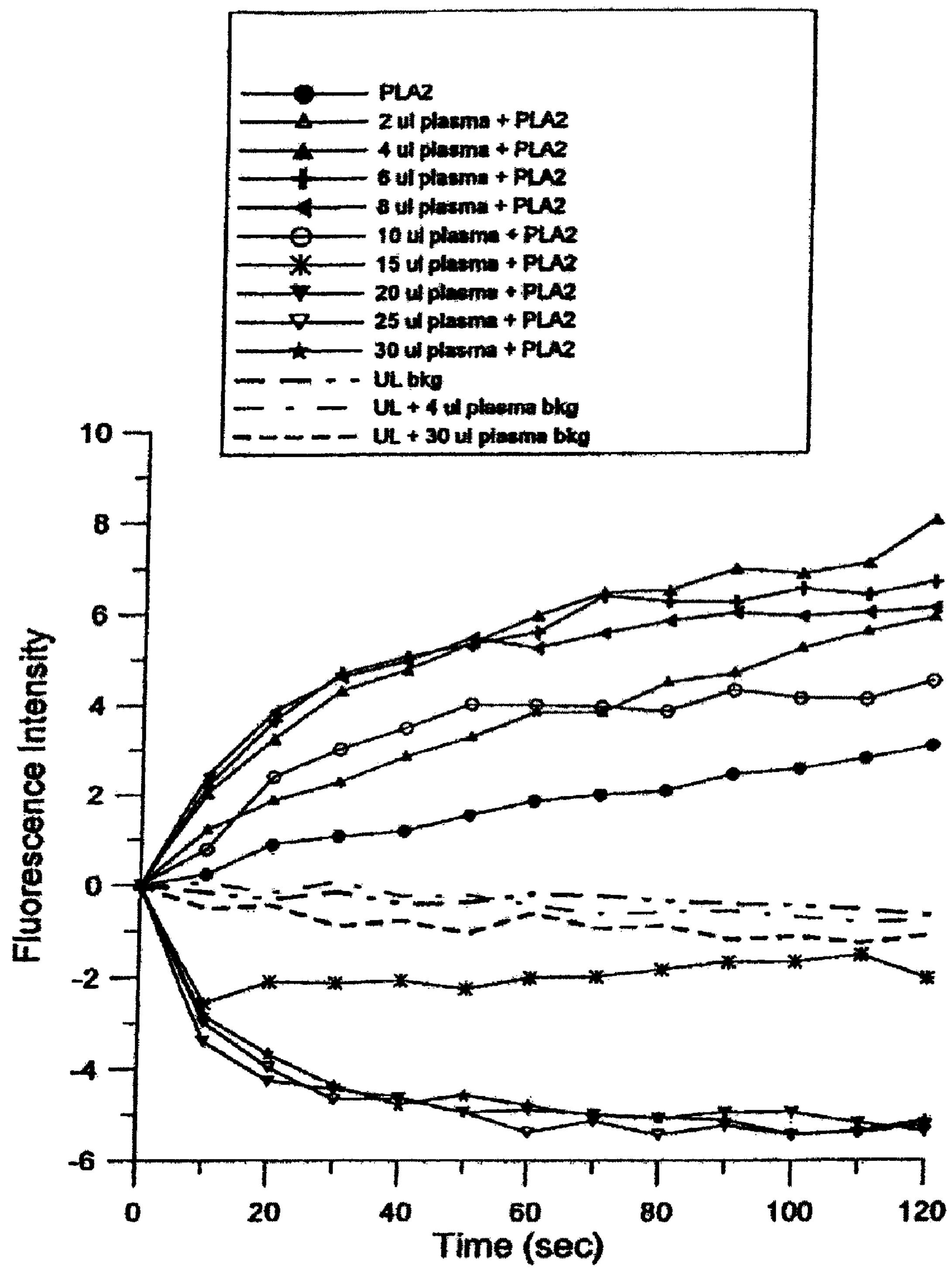

FIG. 12 shows the presence of $PLA_2$-stimulator ($PLA_2$-s) and $PLA_2$-inhibitor (SFA) activity in human plasma.

Figure 13:
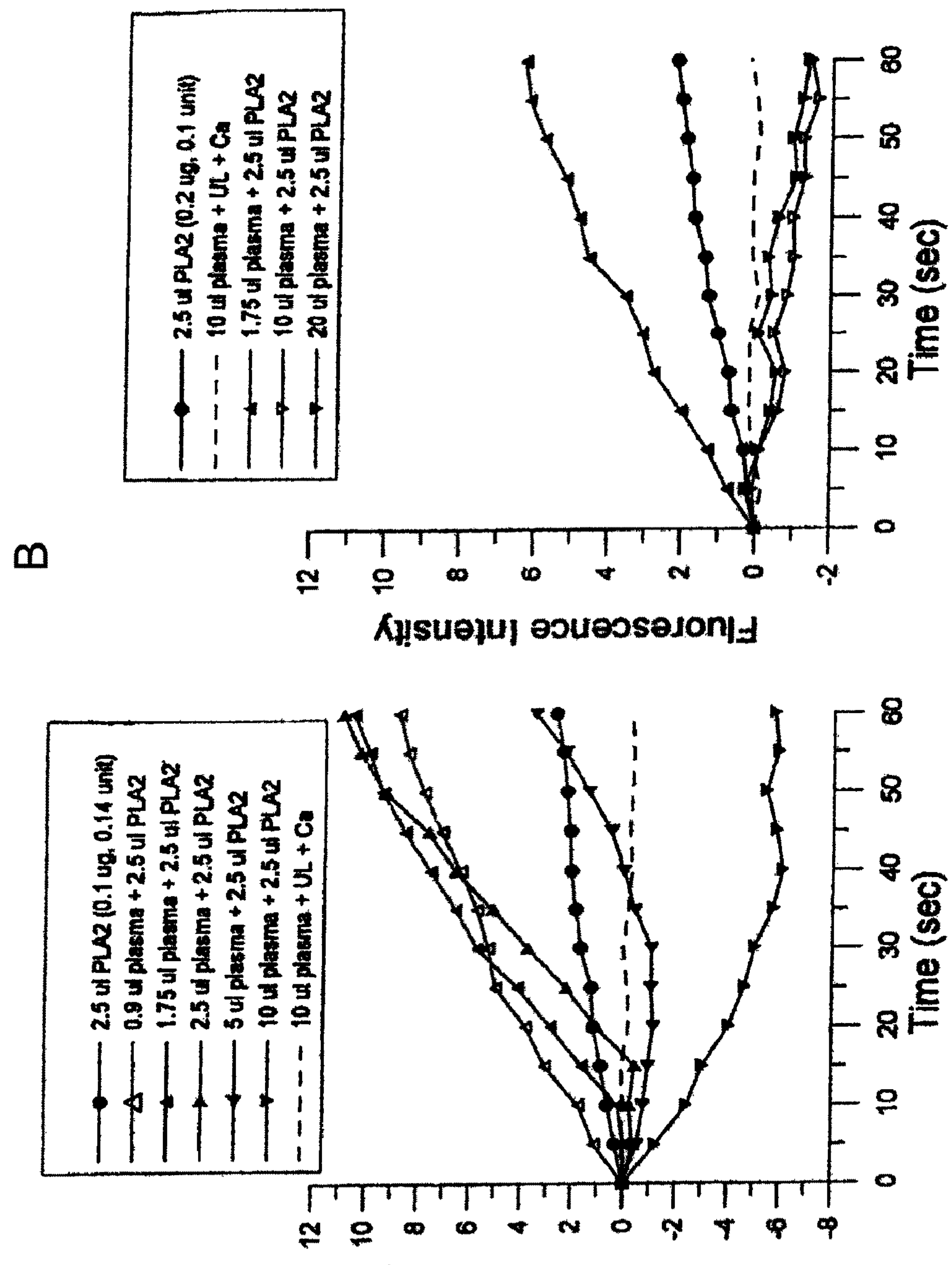

FIG. 13 shows the effects of human plasma on bee venom $PLA_2$ and snake venom $PLA_2$.

Figure 14:
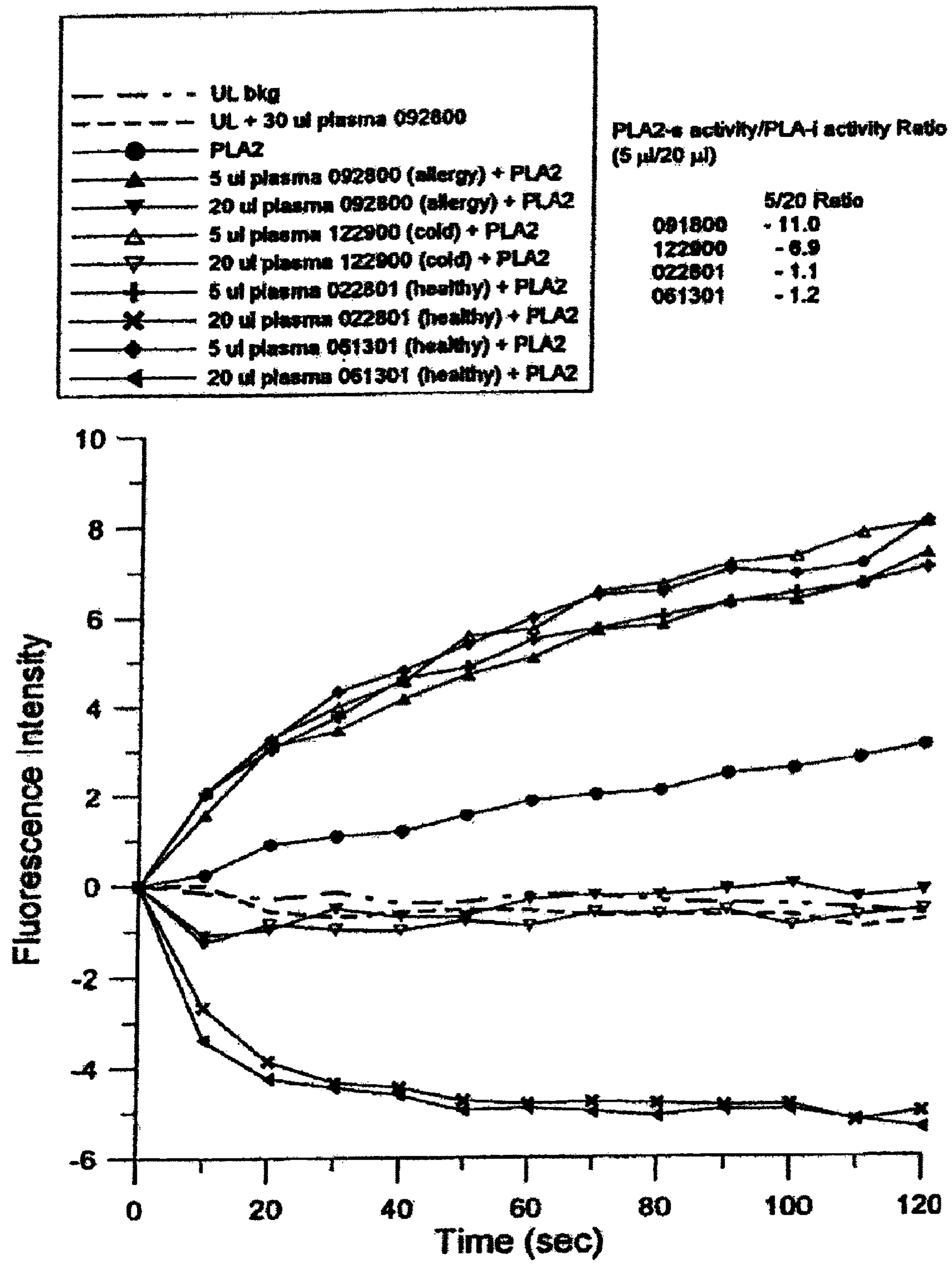

FIG. 14 compares the $PLA_2$-s and SFA activities in the plasma of a human subject when the subject was healthy and when the subject was suffering from allergy or cold.

Figure 15:
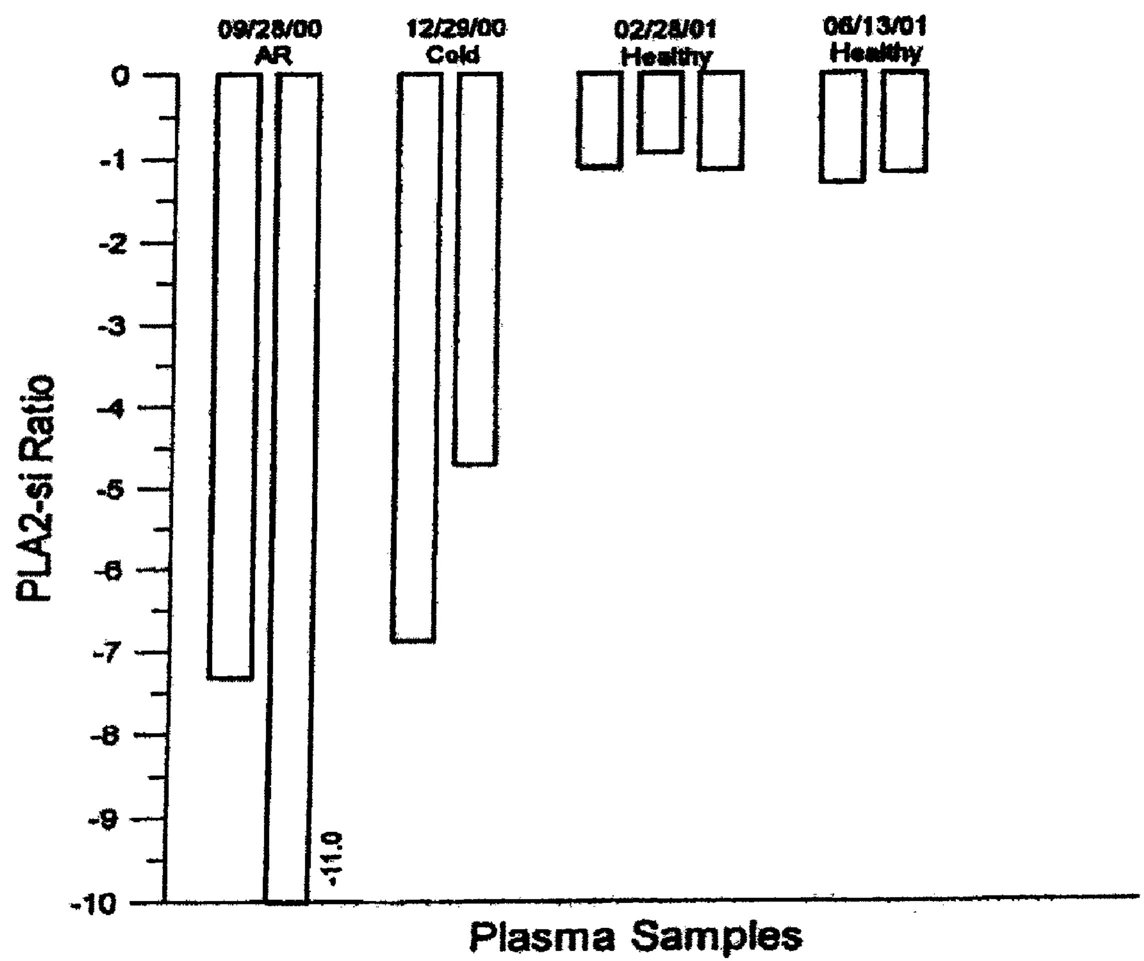

FIG. 15 compares the ratio of $PLA_2$-s to SFA in the plasma of a human subject when the subject was healthy and when the subject was suffering from allergy or cold.

Figure 16:
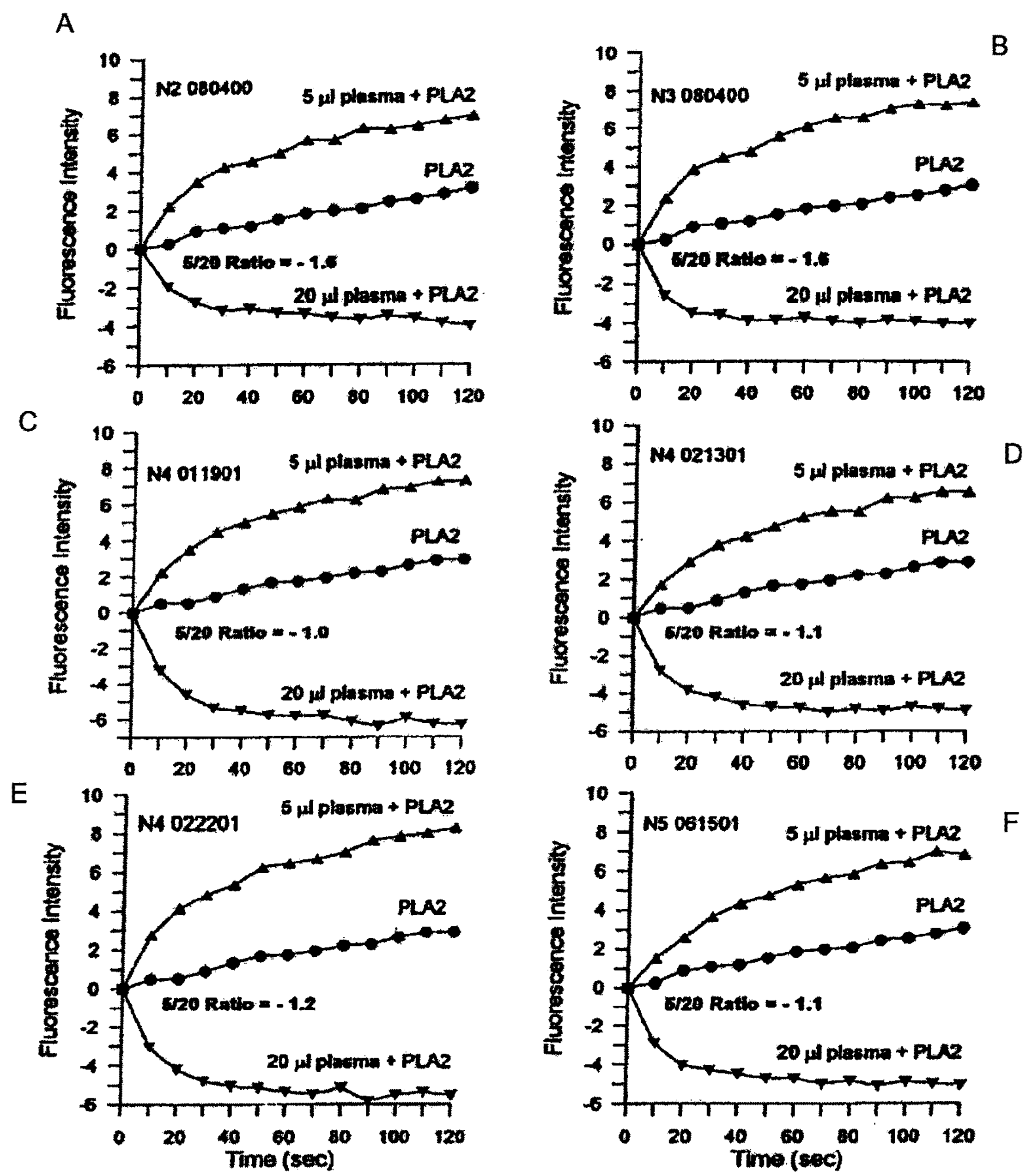

FIG. 16 shows that plasma obtained from four healthy human subjects had both $PLA_2$-s and SFA activities.

Figure 17:
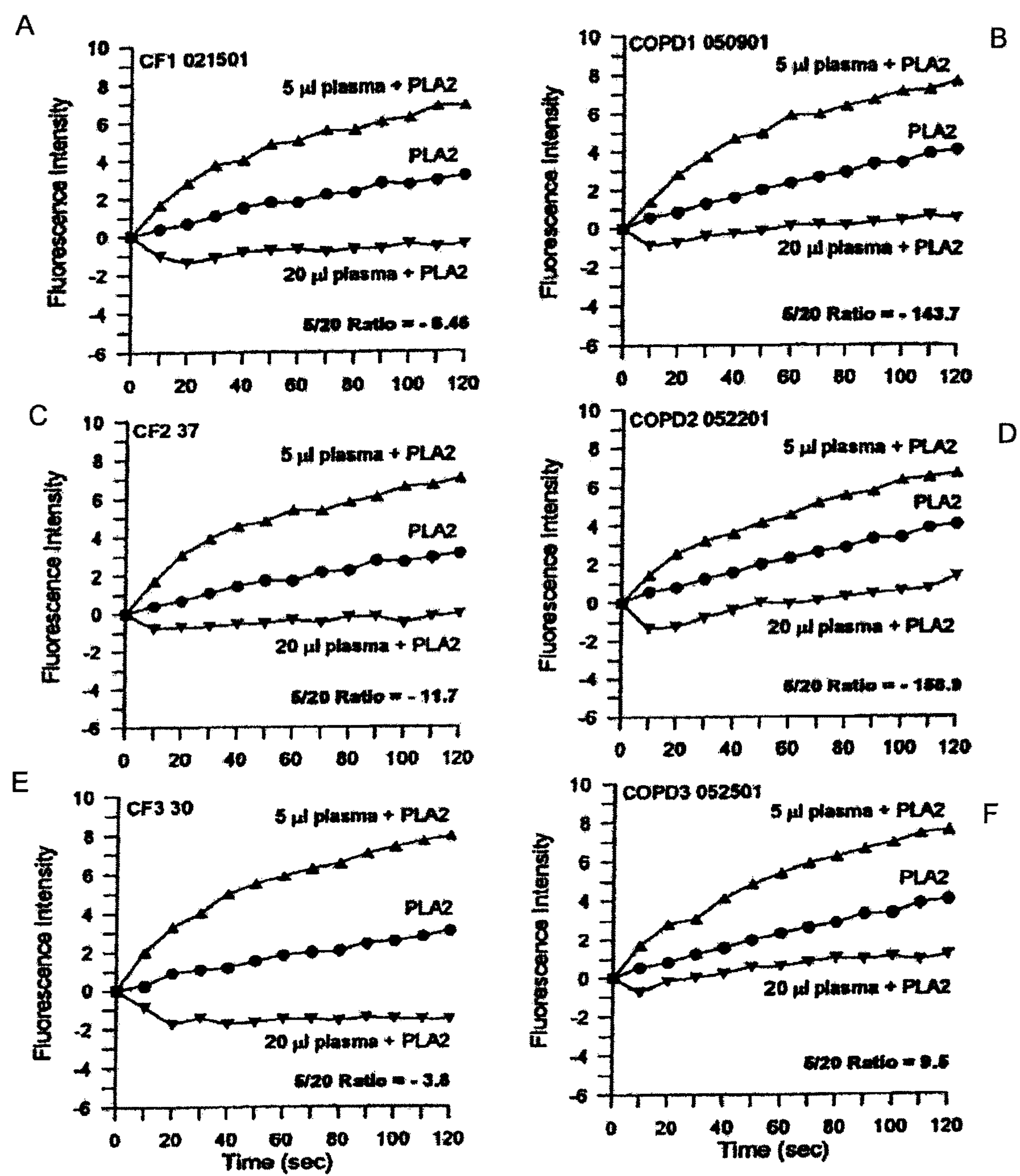

FIG. 17 shows that plasma obtained from four CF and COPD (Chronic Obstructive Pulmonary Disease) human subjects had only $PLA_2$-s activity.

Figure 18:
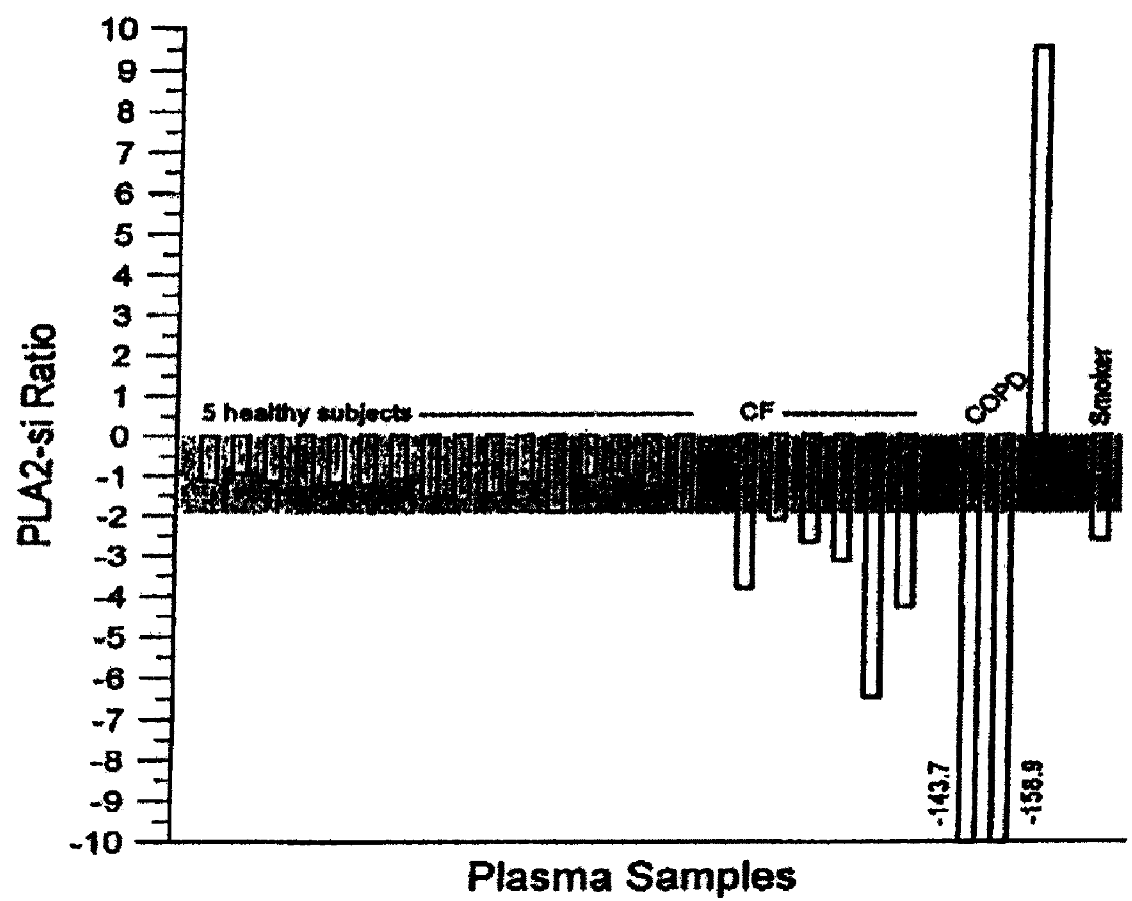

FIG. 18 shows the $PLA_2$-s to SFA ratios of plasma from healthy human subjects, human subjects with inflammation symptoms and a smoker.

Figure 19:
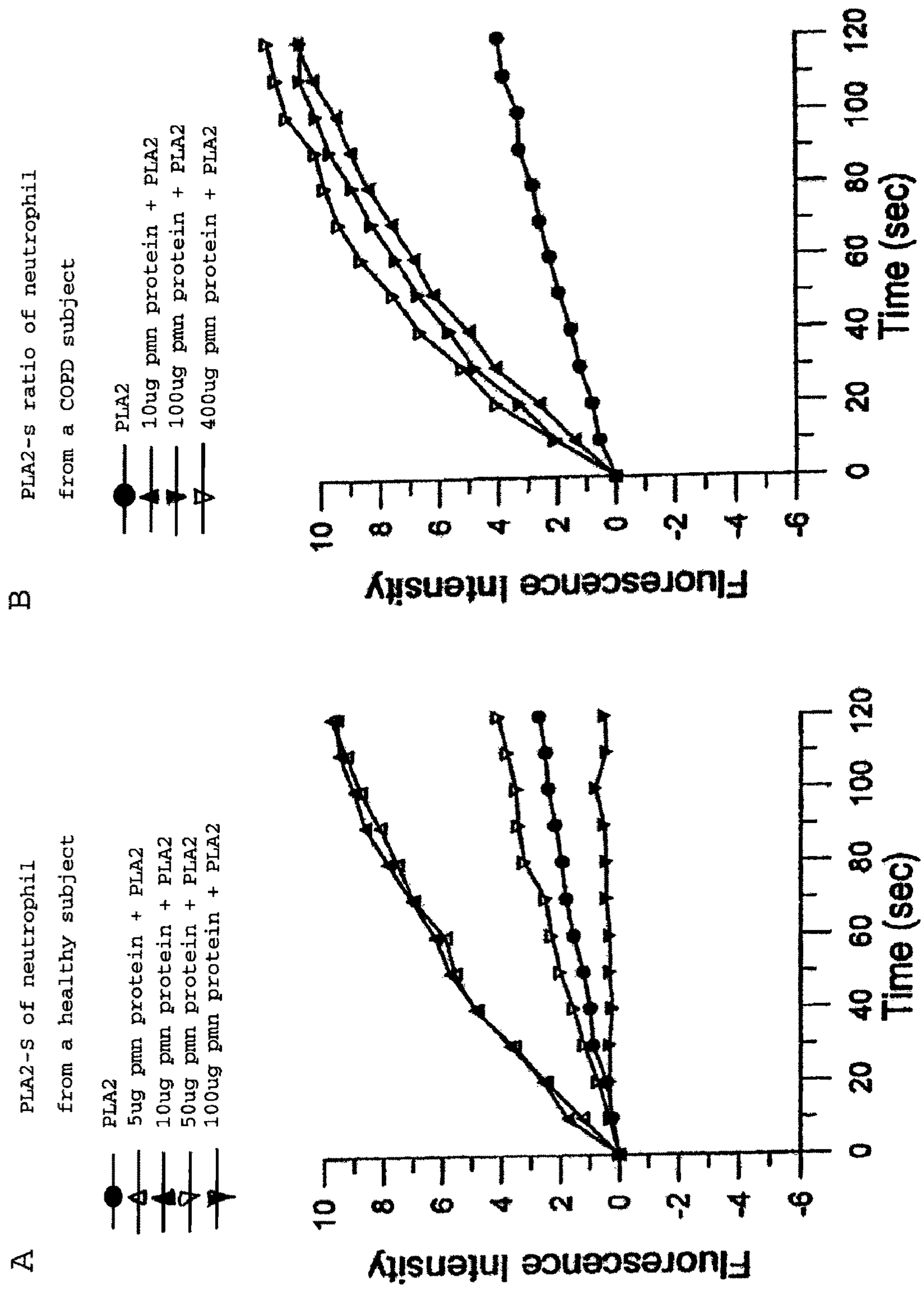

FIG. 19 shows $PLA_2$-s and SFA activities in neutrophils from a healthy subject and a COPD subject.

Figure 20:
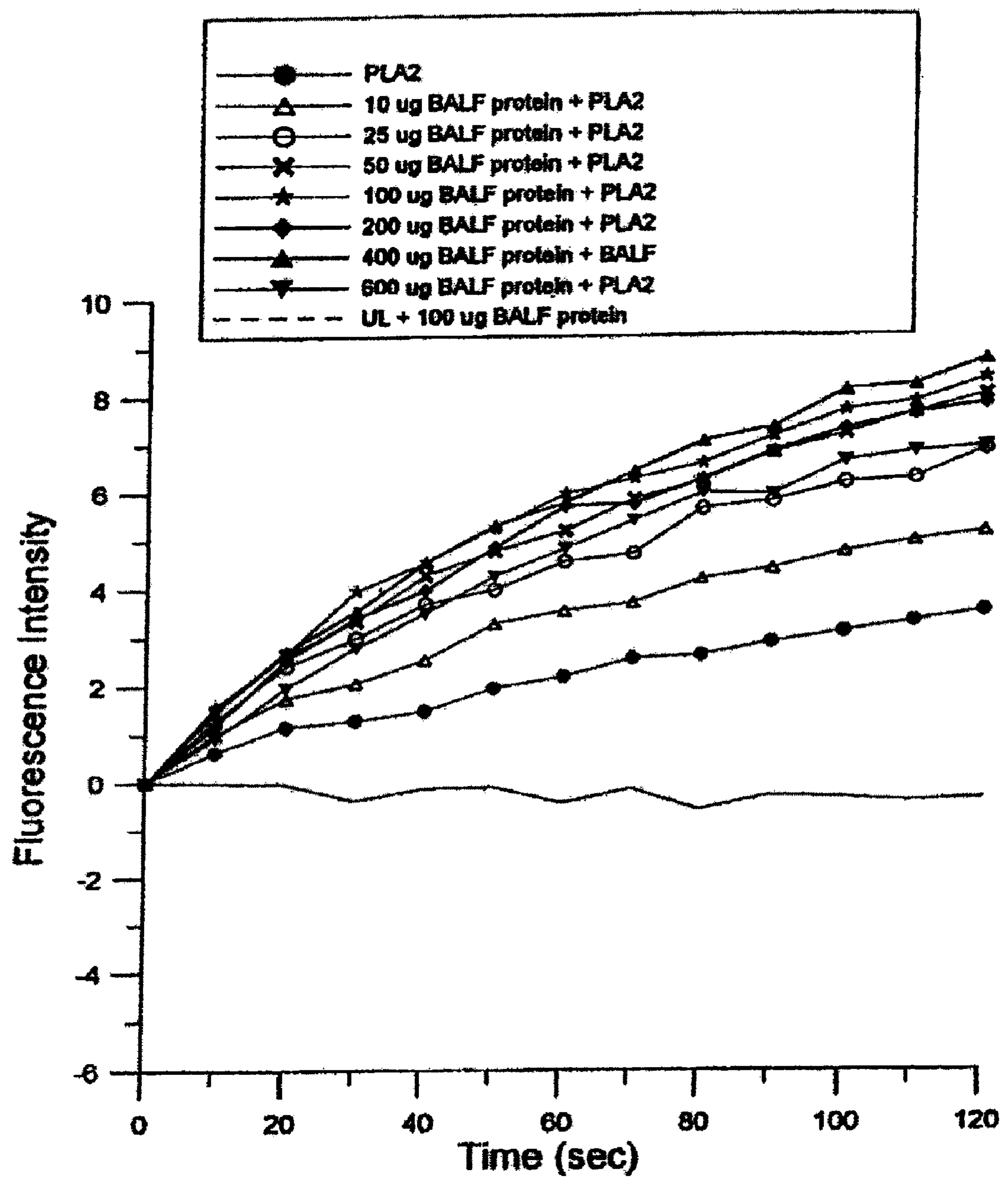

FIG. 20 shows $PLA_2$-s and SFA activities in BALF.

Figure 21:
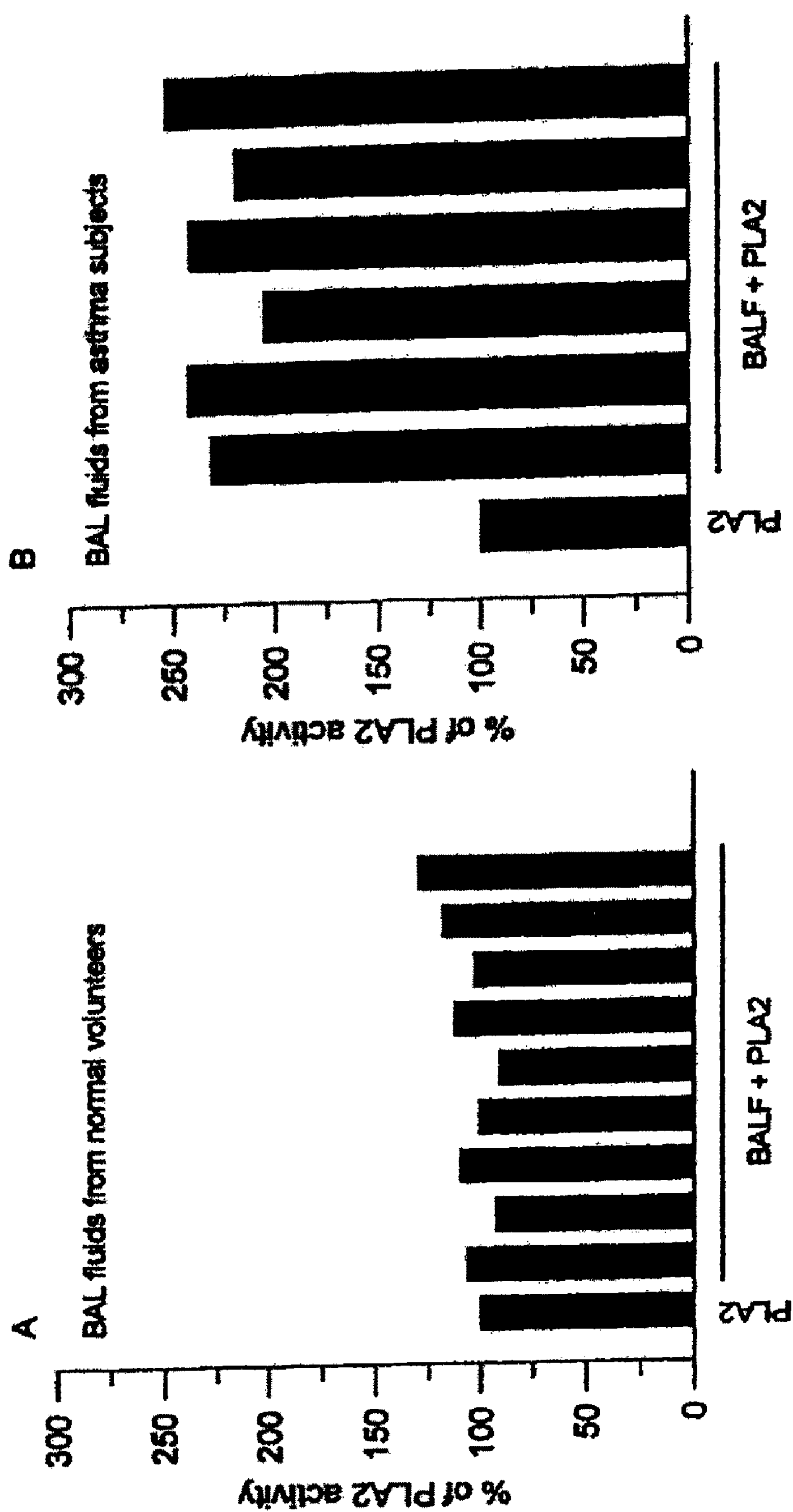

FIG. 21 shows the $PLA_2$-s activity of BALF from normal human subjects (A) and asthma human subjects (B).

Figure 22:
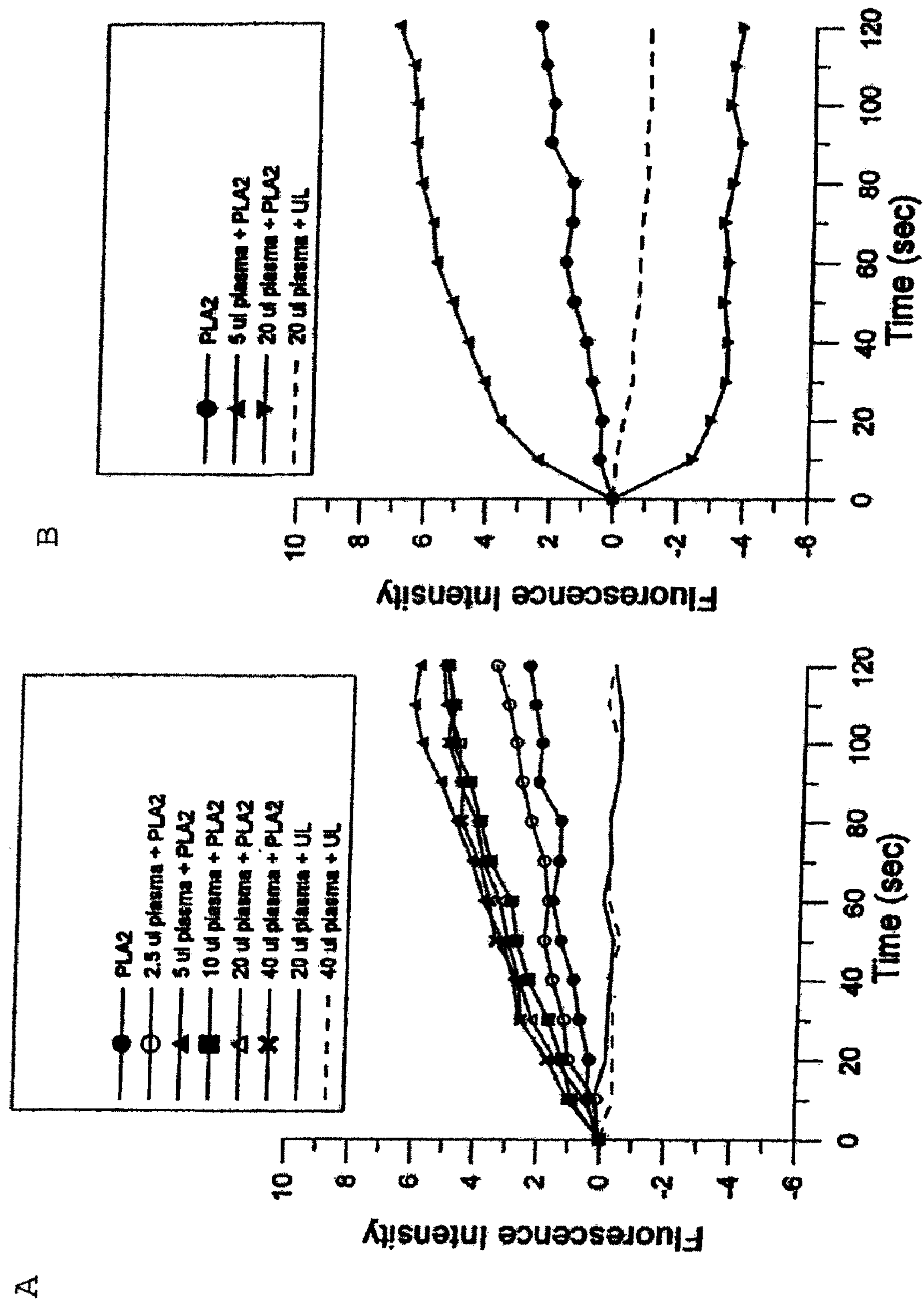

FIG. 22 shows the effect of heating on plasma $PLA_2$-s and SFA activities.

Figure 23:
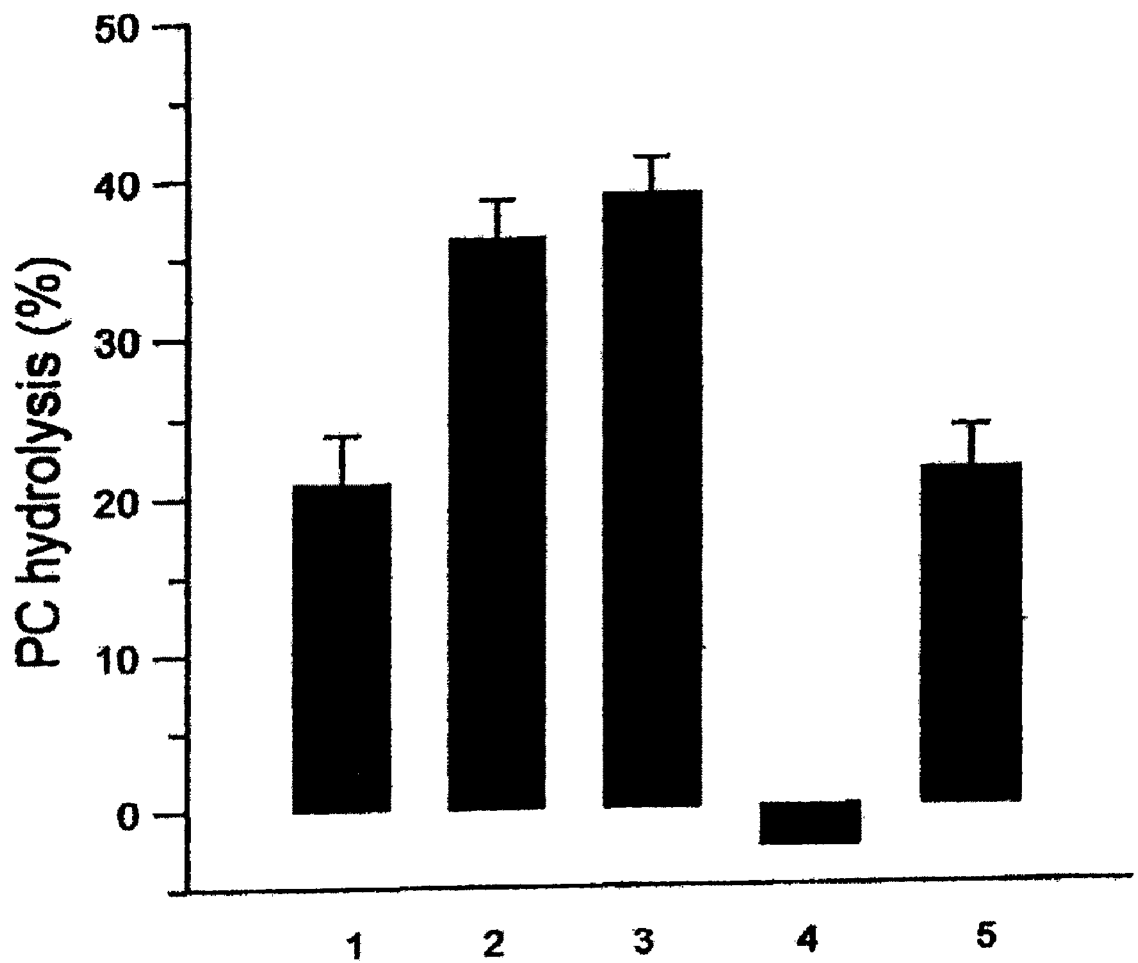

FIG. 23 compares the $PLA_2$-s activity of BALF from a normal human subject and a CF human subject using a radioactive assay.

Figure 24:
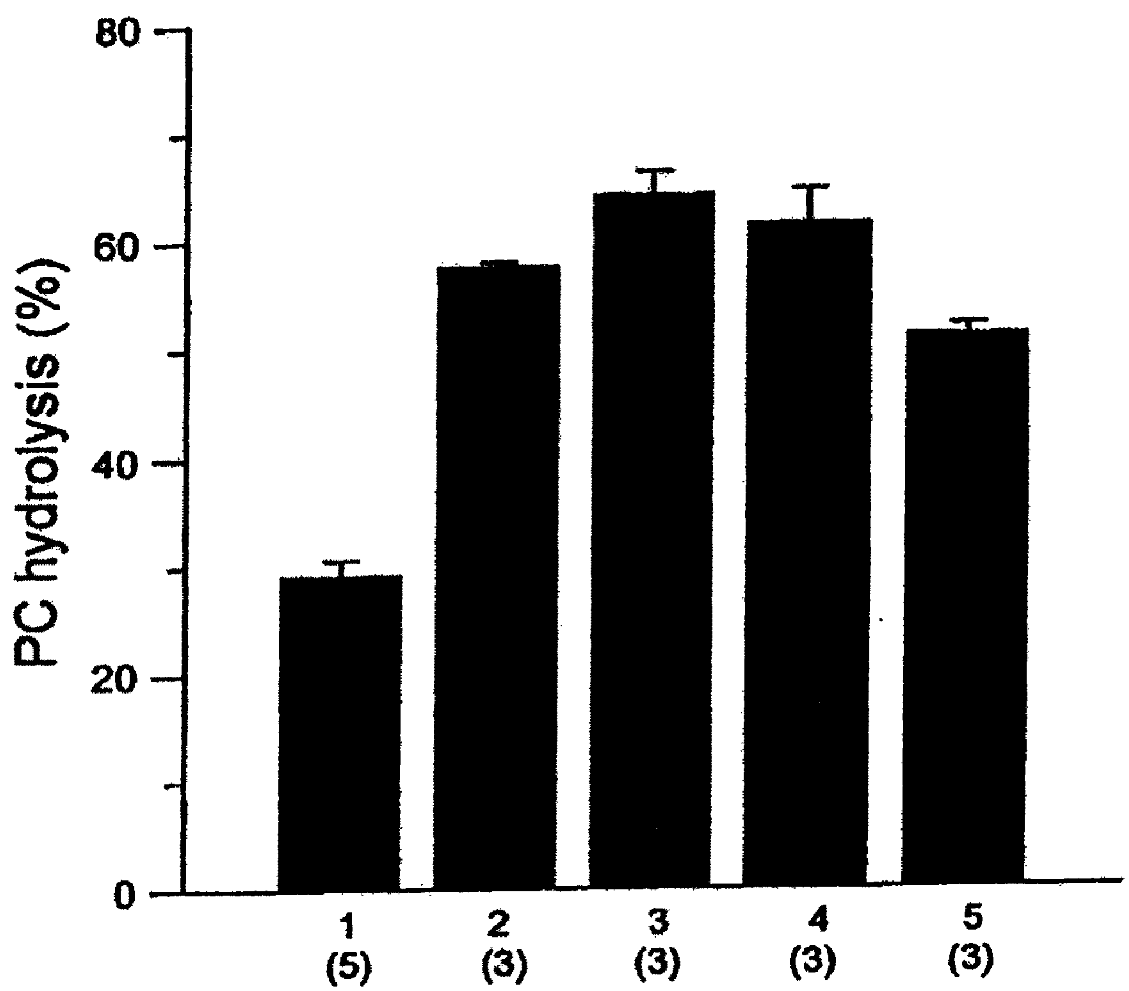

FIG. 24 shows the effect of heating on the $PLA_2$-s activity of BALF from a CF human subject using a radioactive assay.

Figure 25:
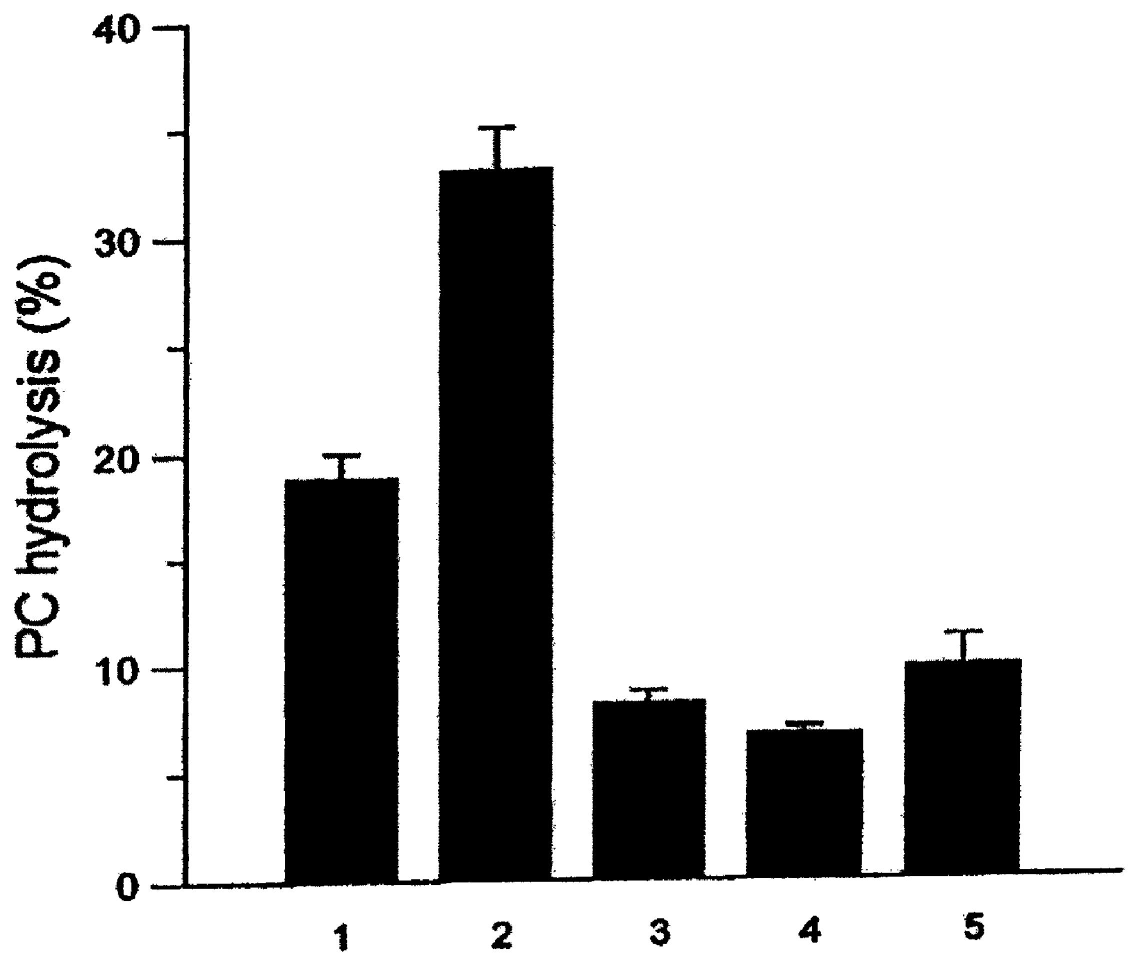

FIG. 25 shows that Annexins I and VIII can inhibit the $PLA_2$ activity and the $PLA_2$-s activity.

Figure 26:
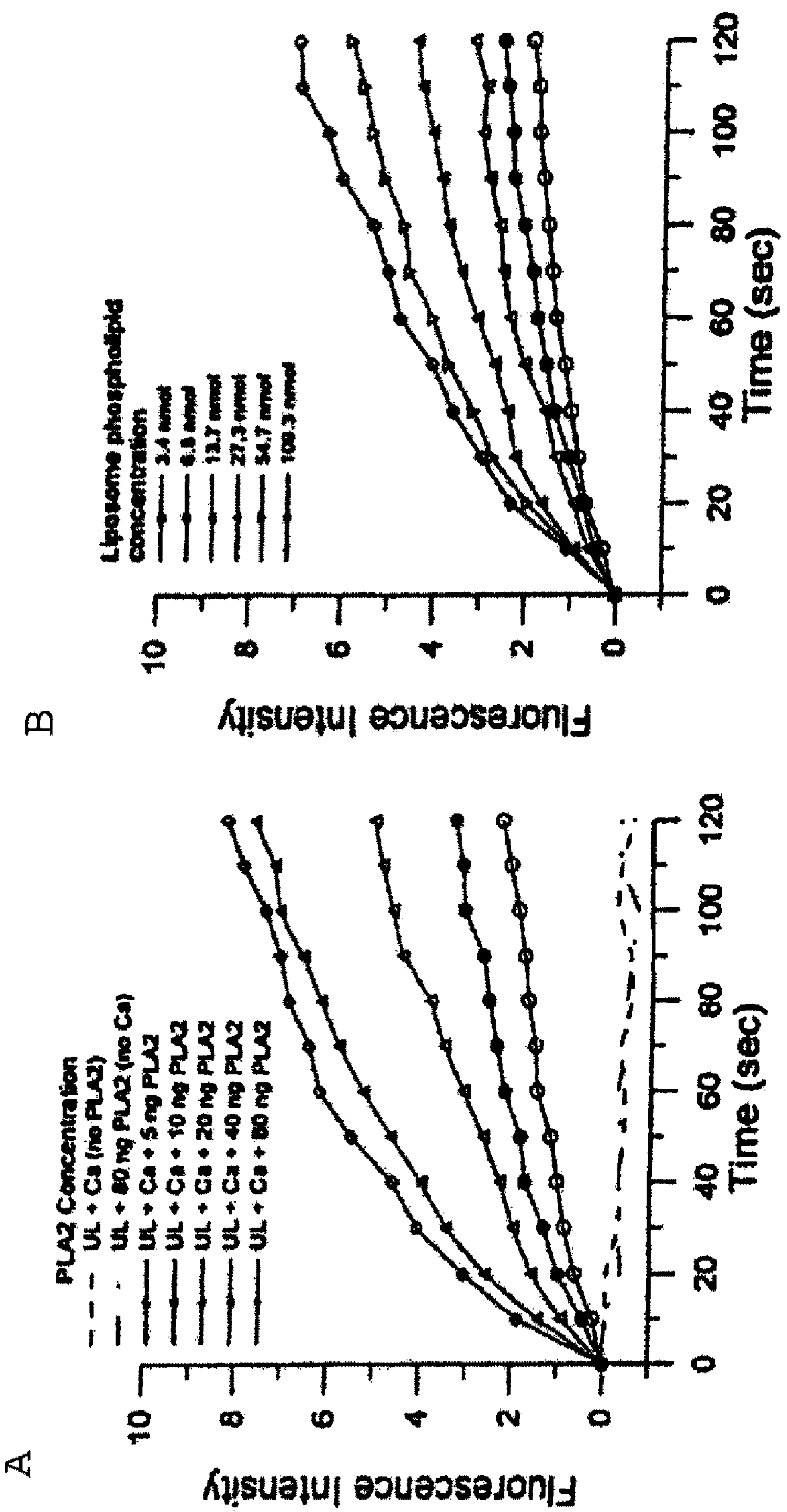

FIG. 26 shows protein and liposome concentration dependence of $PLA_2$ activity determined by the fluorescent assay. Porcine pancreatic $PLA_2$ was used as the enzyme source. Fluorescently labeled unilamellar liposomes were used as substrate.

Figure 27:
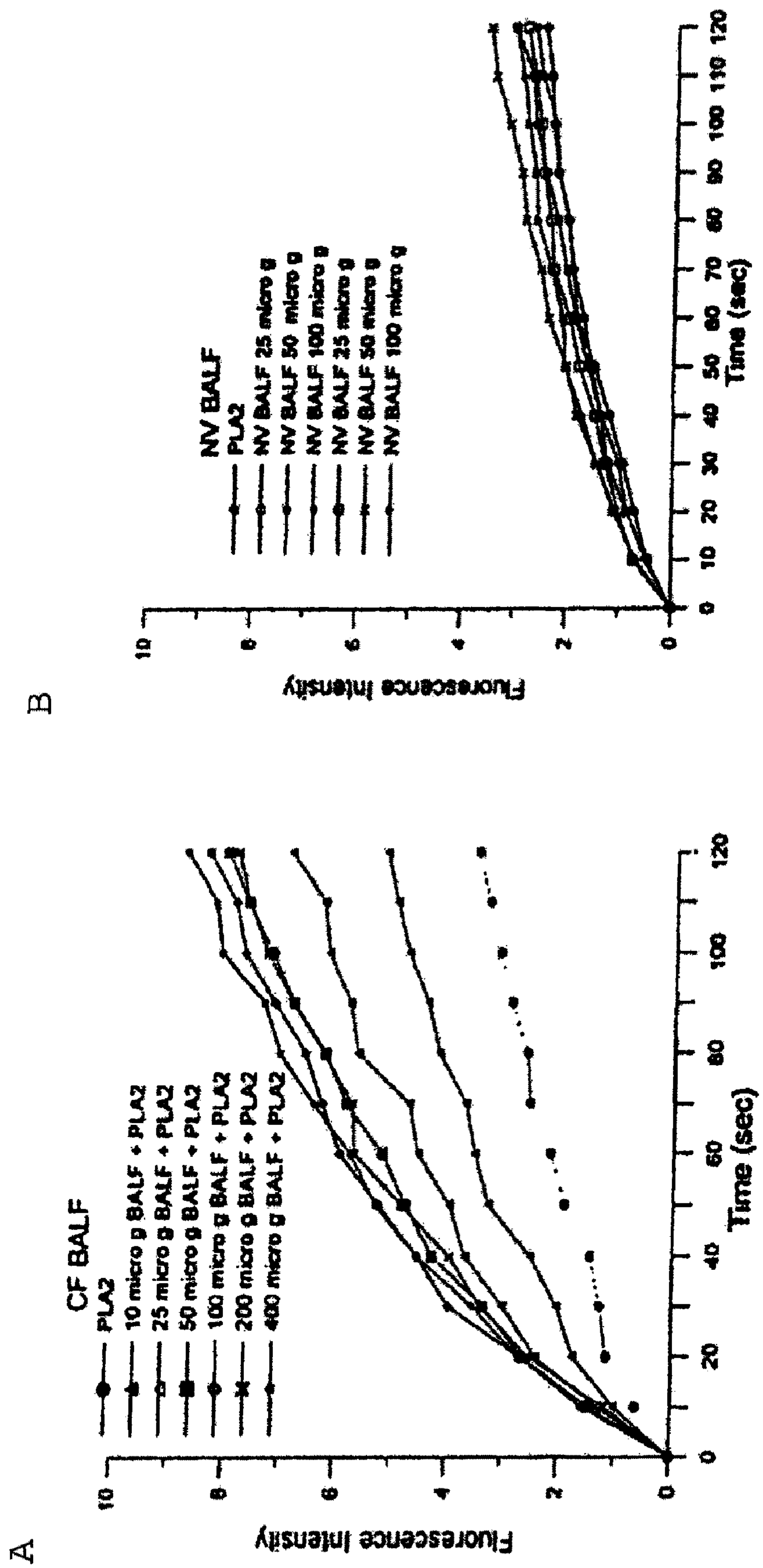

FIG. 27 shows the effect of BALF on $PLA_2$ activity. Left: CF BALF; Right: normal volunteer (NV) BALF.

Figure 28:
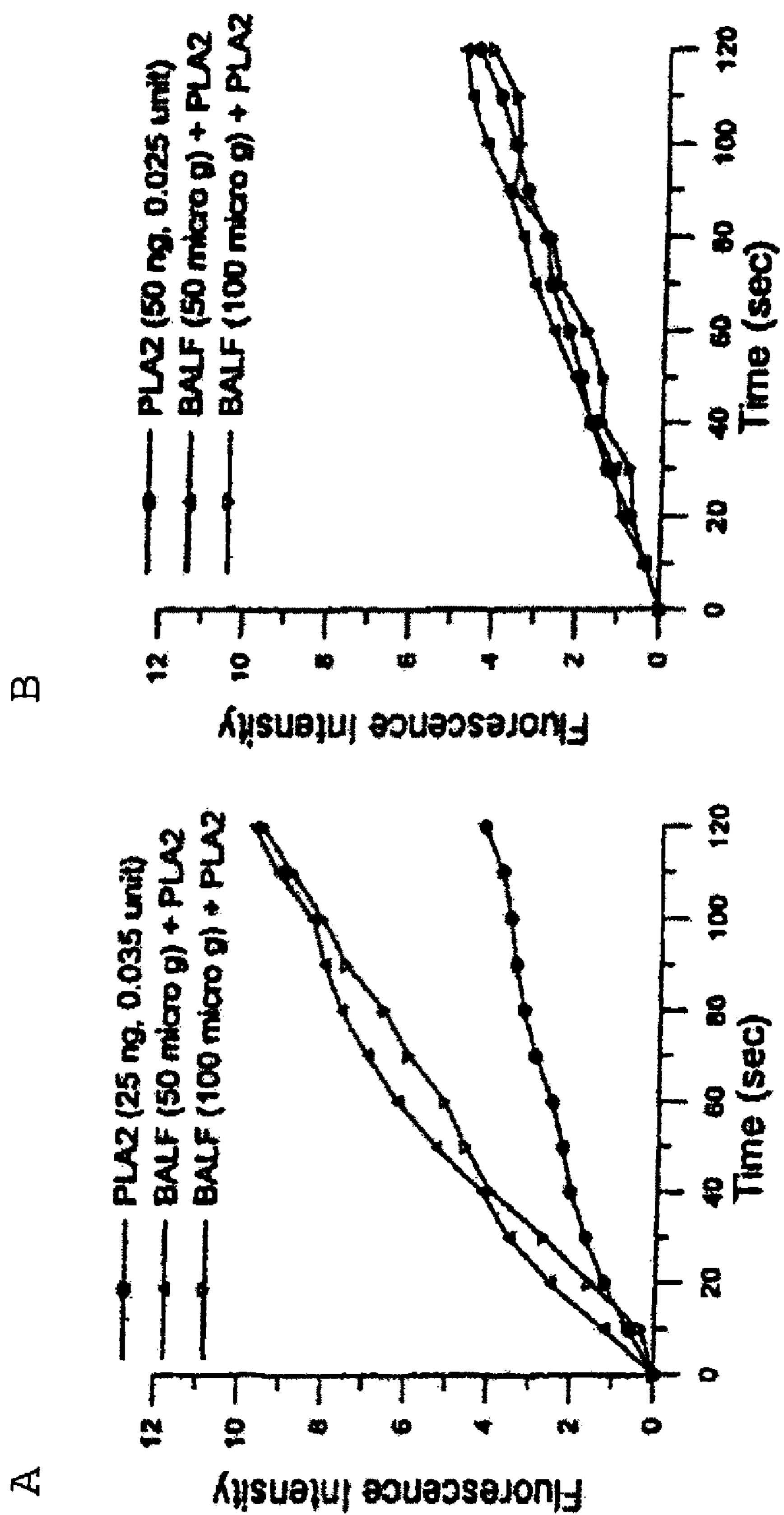

FIG. 28 shows the effect of CF BALF on bee venom $PLA_2$ (A) and rattlesnake venom $PLA_2$ (B).

Figure 29:
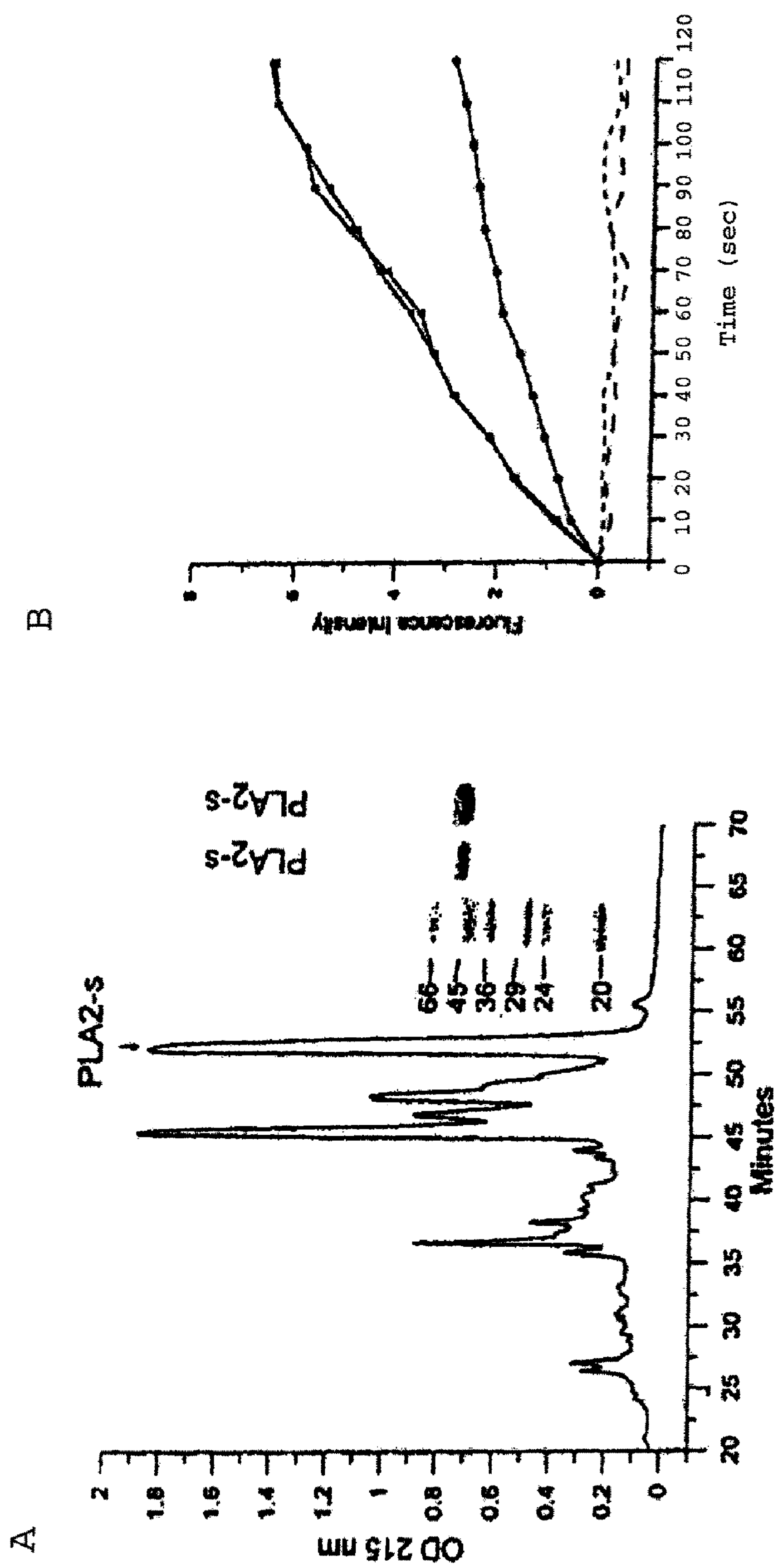

FIG. 29 shows reverse phase HPLC chromatogram and SDS gel electrophoresis of $PLA_2$-s (A) and the effect of the isolated $PLA_2$-s on pancreatic $PLA_2$ activity (B). The $PLA_2$-s samples applied to the SDS gel were from two HPLC preparations. An amount of 6 μg of $PLA_2$-s from two different HPLC preparations was tested by the fluorescent assay. The dotted lines represent the reaction containing $PLA_2$-s, liposomes and $Ca^{2+}$ but no $PLA_2$.

Figure 30:
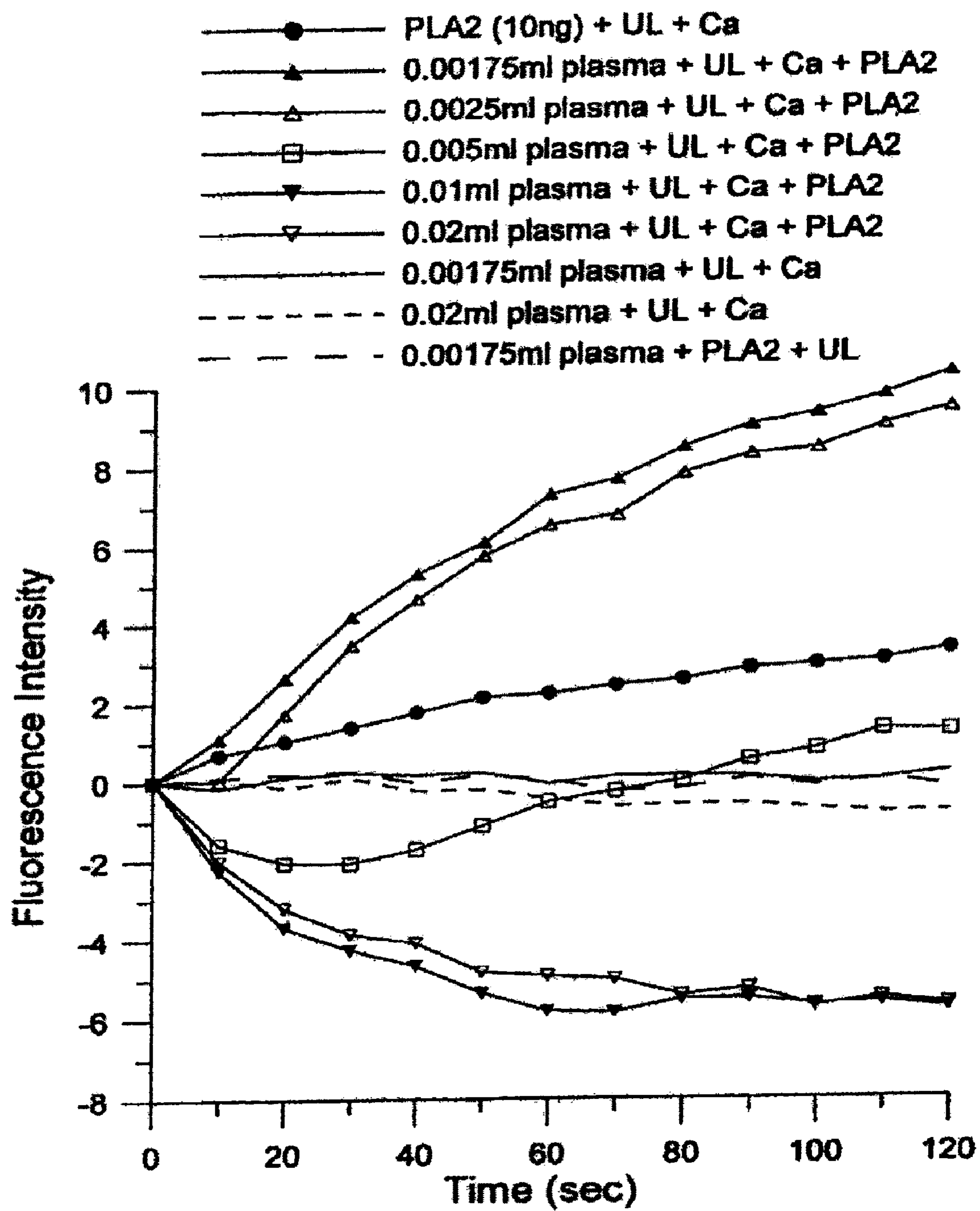

FIG. 30 shows the effects of plasma on pancreatic $PLA_2$ activity using the fluorescent assay. The assay mixture contained fluorescently labeled liposomes, 10 mM $CaCl_2$, and in the presence or absence of $PLA_2$ or plasma as detailed in the text. The reaction was carried out at room temperature.

Figure 31:
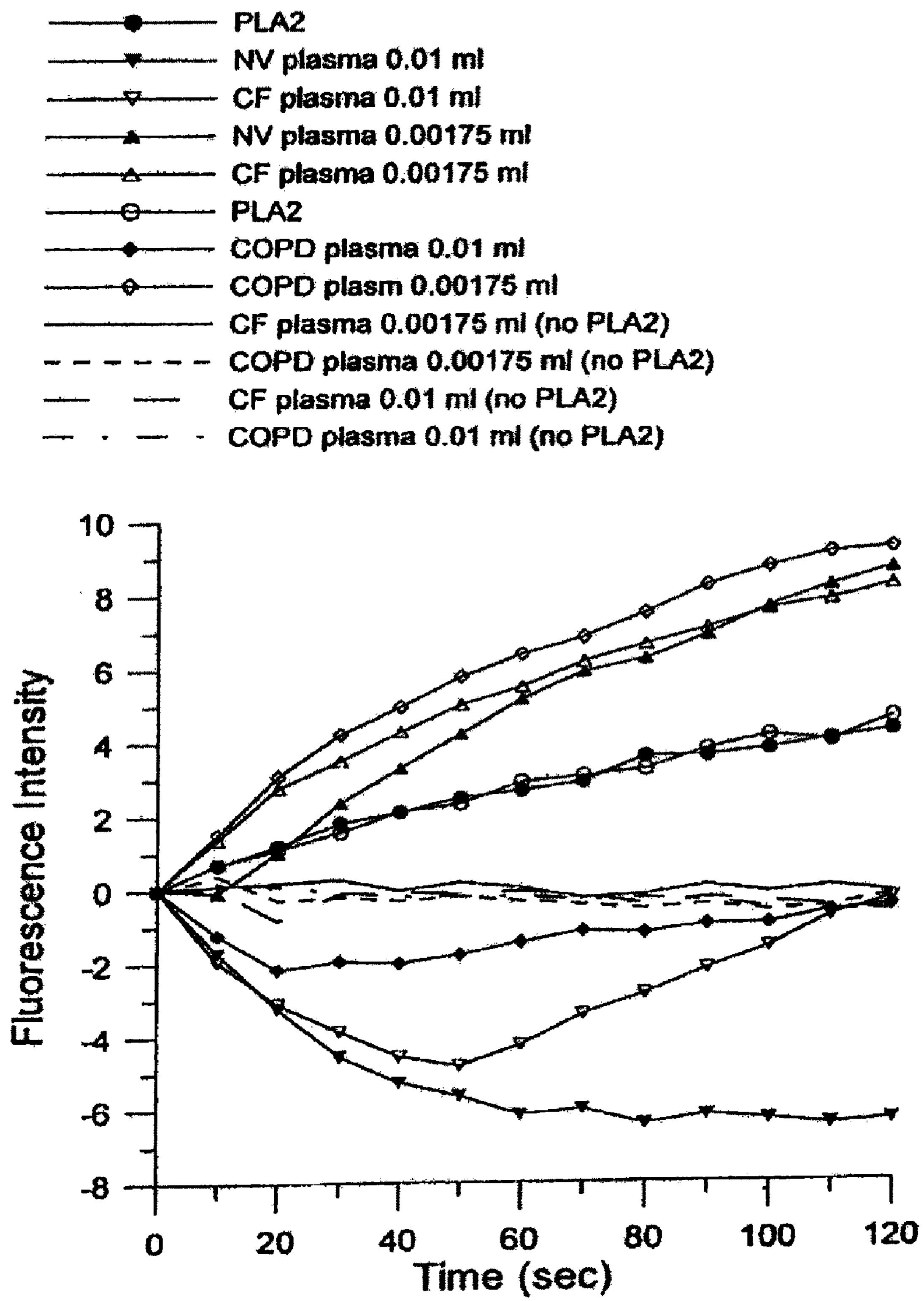

FIG. 31 compares the effects of plasma from a normal volunteer (NV) and subjects with CF or COPD on $PLA_2$ determined by the fluorescent assay.

Figure 32:
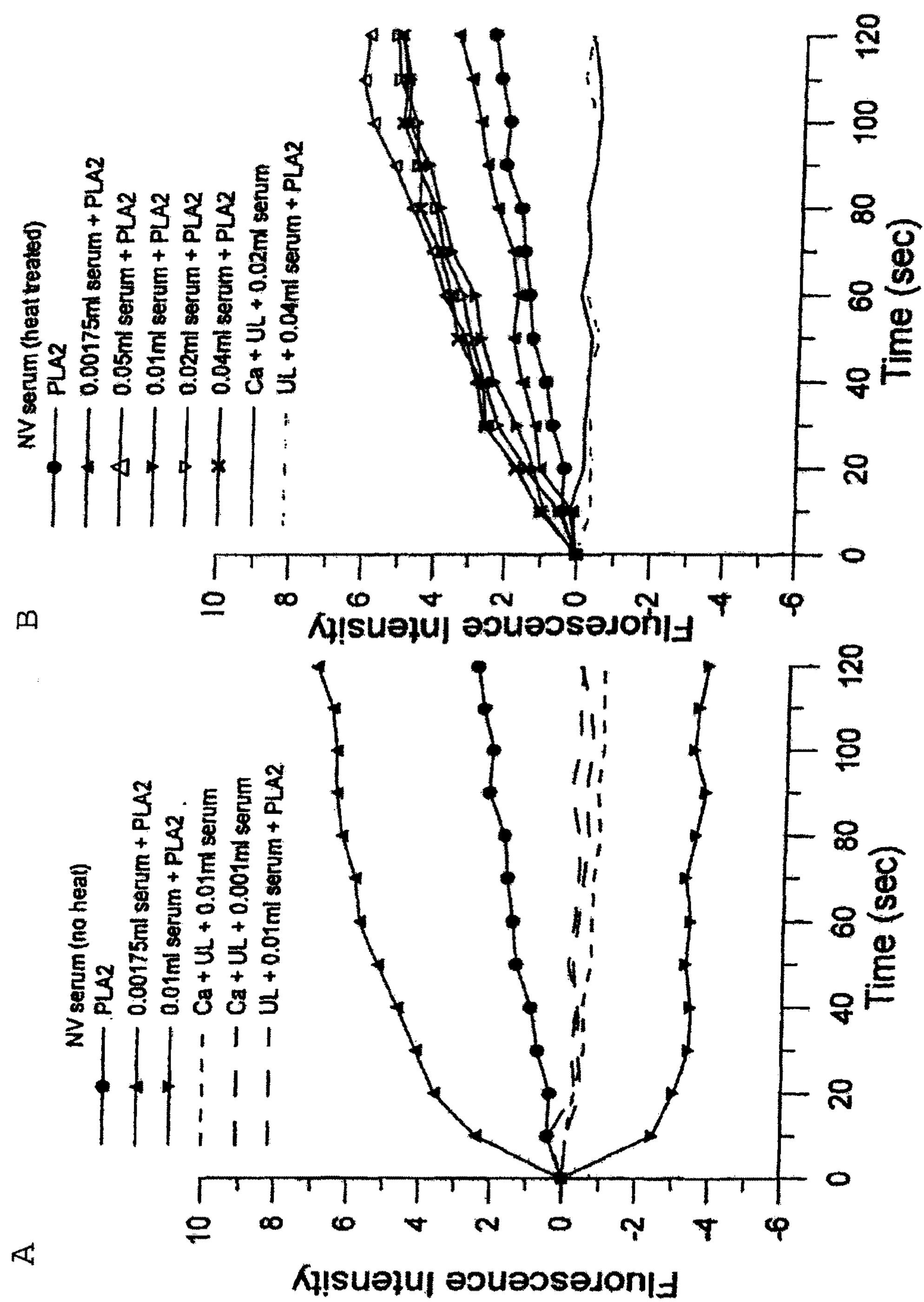

FIG. 32 shows effects of prior (A) or after (B) heat treatment of serum on $PLA_2$ activity determined by the fluorescent assay. Serum was obtained from a normal volunteer (NV). Heat treatment of serum was conducted by immersing serum in boiling water for 5 min followed by centrifugation to remove precipitated proteins. The supernatant was used for assay.

Figure 33:
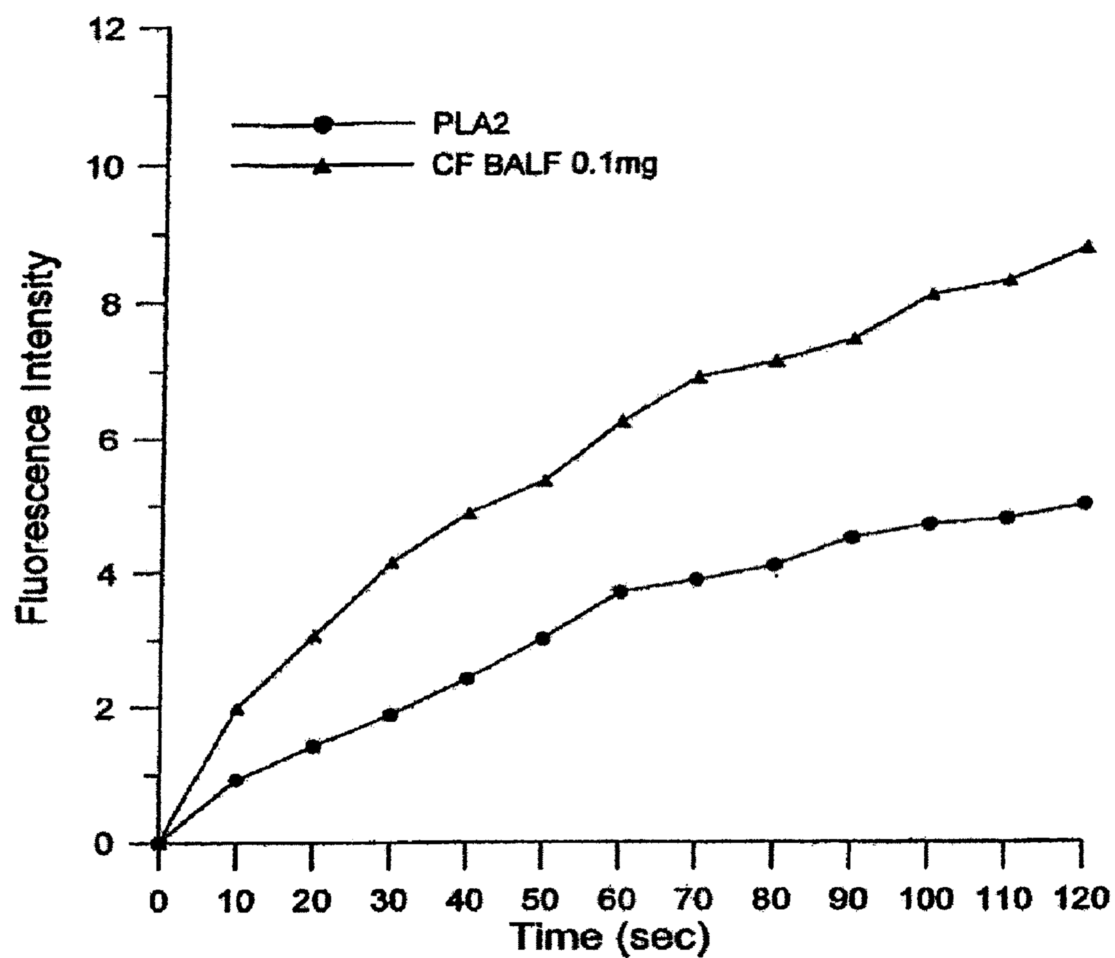

FIG. 33 shows the effect of BALF from CF subject on pancreatic $PLA_2$ activity determined by the fluorescent assay.

Figure 34:
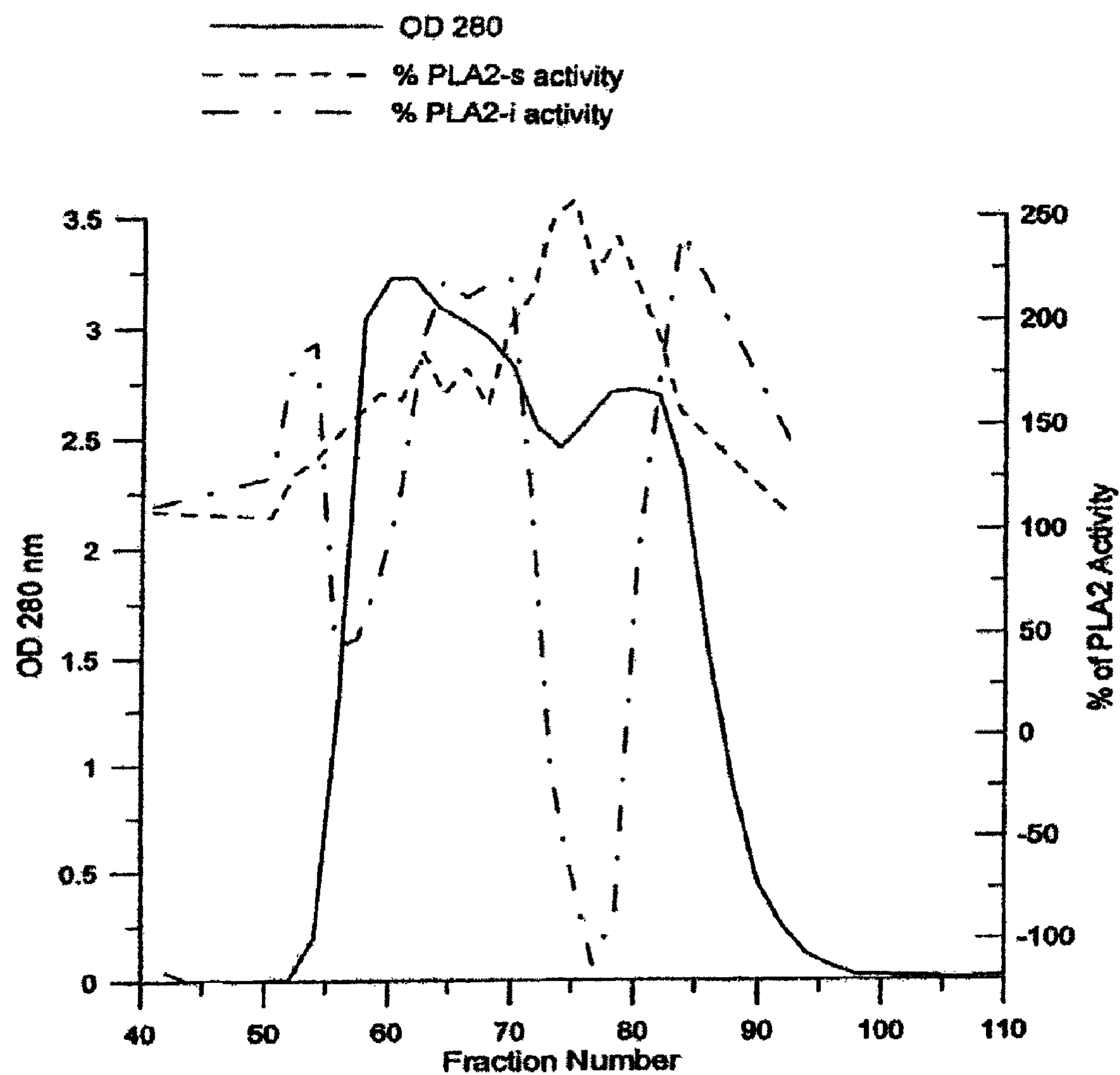

FIG. 34 shows gel filtration column chromatogram of serum. A total of 7 ml of serum from normal volunteers (NVs) was applied to a Sephadex G-100 column and serum components were eluted from the column with Tris buffer as described in text. The amount of protein in fractions was determined by measuring the optical density at 280 nm; $PLA_2$-s and SFA activities were determined by the fluorescent assay and expressed as percentage of the control $PLA_2$ activity.

Figure 35:
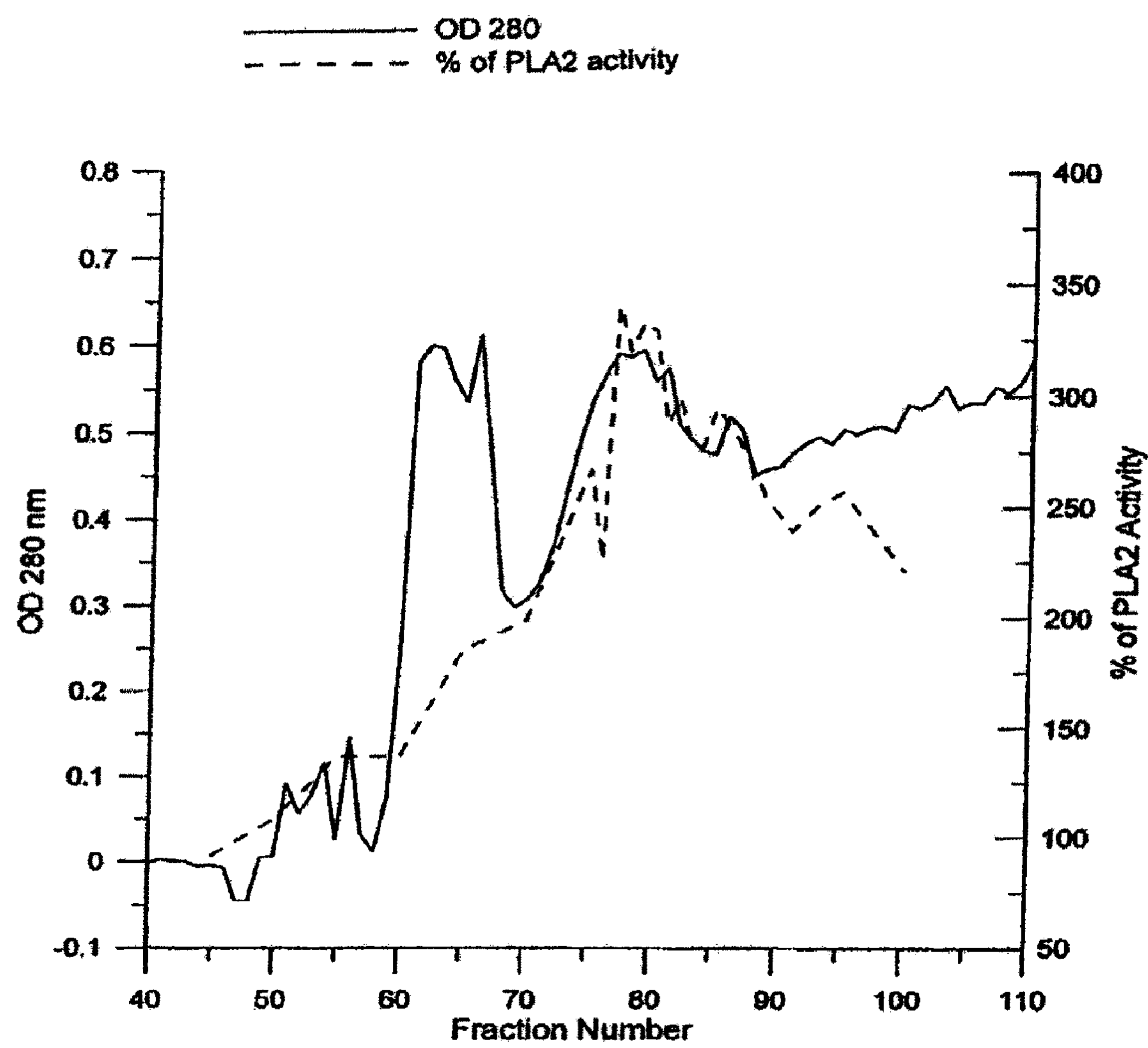

FIG. 35 shows gel filtration column chromatogram of heat-treated CF BALF. Protein and $PLA_2$-s activity in fractions were determined as described in FIG. 23.

Figure 36:
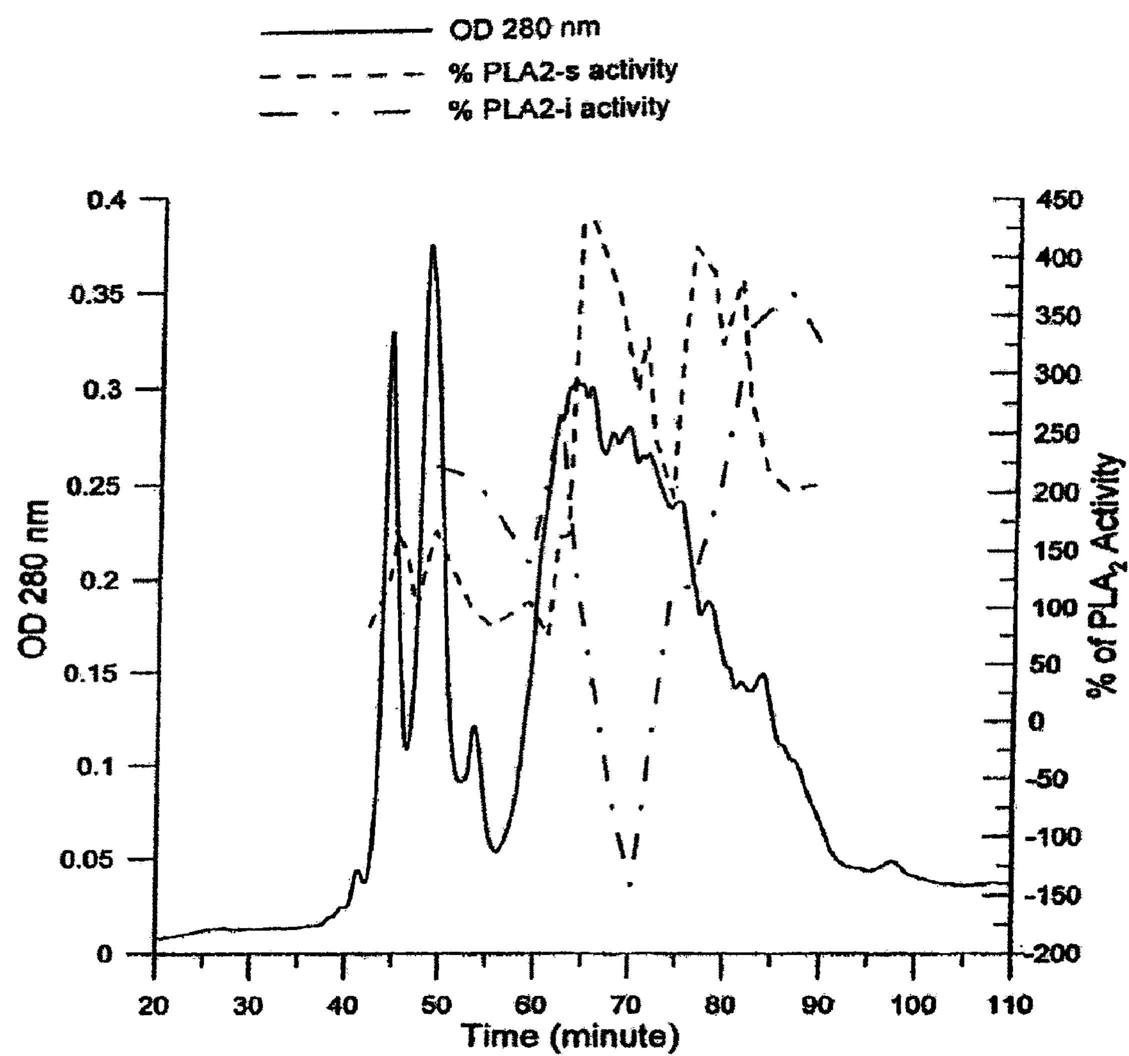

FIG. 36 shows HPLC anionic exchange column chromatogram of serum proteins. The serum proteins were partially purified from gel filtration column chromatography (FIG. 33) and the proteins were applied to an HPLC MonoQ anionic exchange column and eluted with Tris buffer with NaCl salt gradient as described in text. Protein and SFA and $PLA_2$-s activities were determined as described in FIG. 33.

Figure 37:
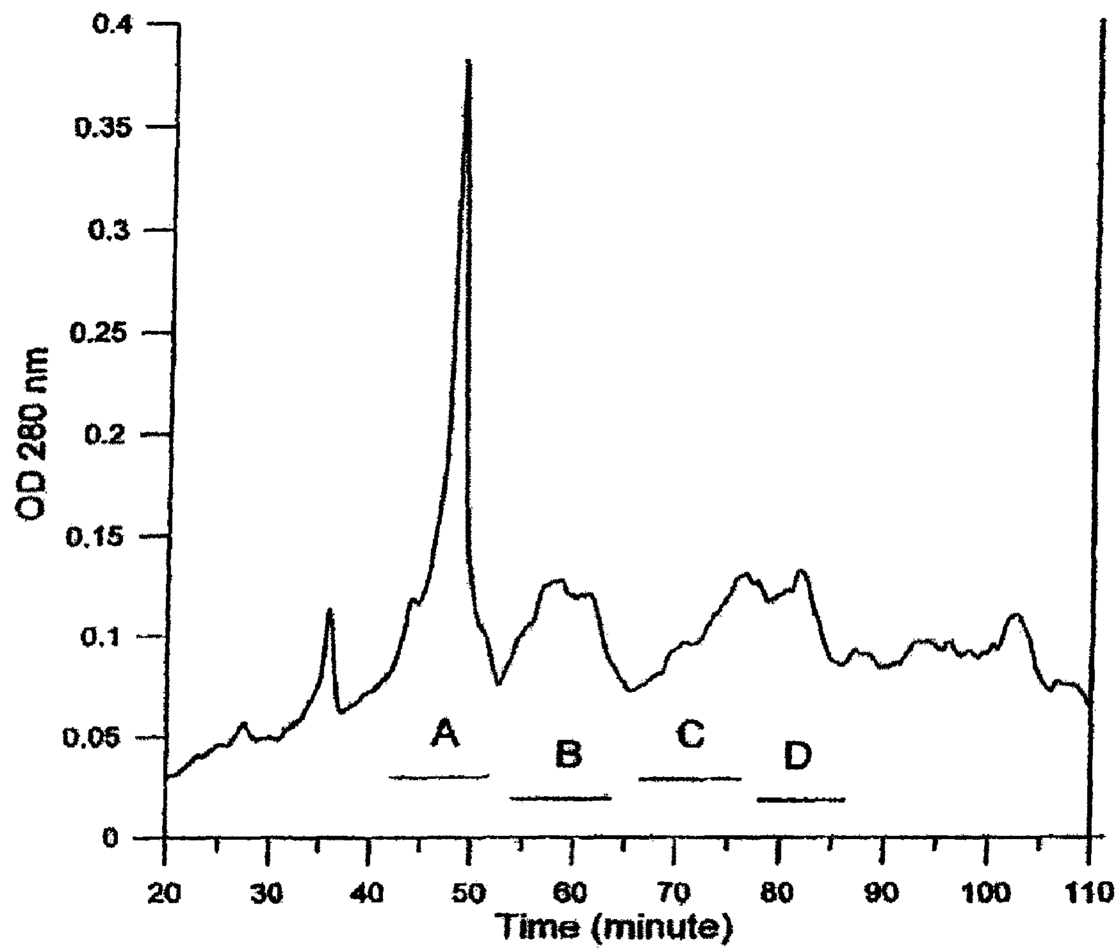

FIG. 37 shows HPLC anionic exchange column chromatogram of CF BALF proteins. The CF BALF proteins were partially purified from gel filtration column chromatography (FIG. 34) and the proteins were applied to an HPLC MonoQ anionic exchange column and eluted with Tris buffer with NaCl salt gradient as described in text. Protein and SFA and $PLA_2$-s activities were determined as described in FIG. 33.

Figure 38:
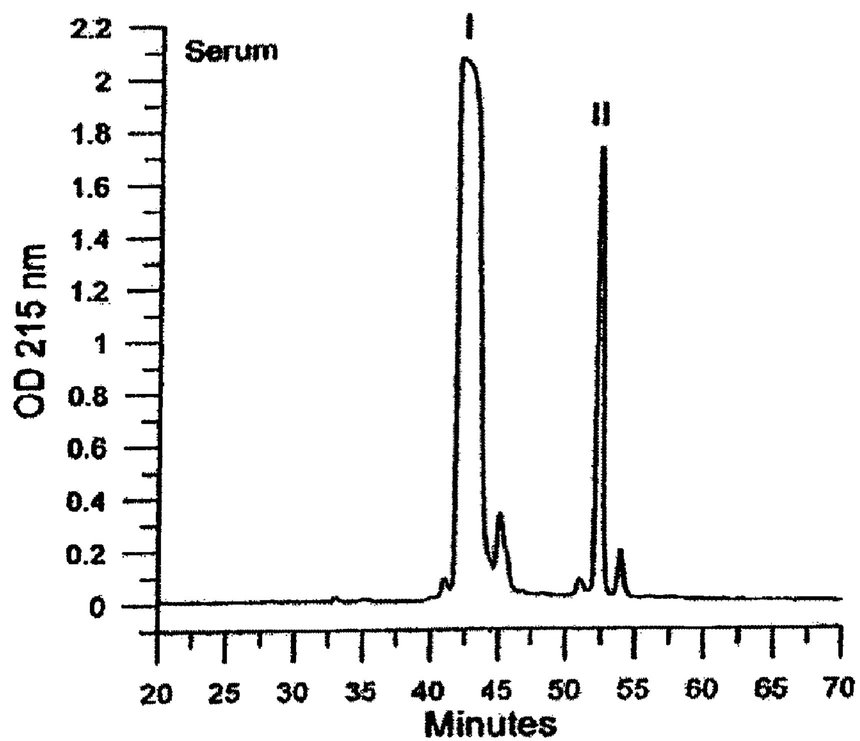
Figure 38:
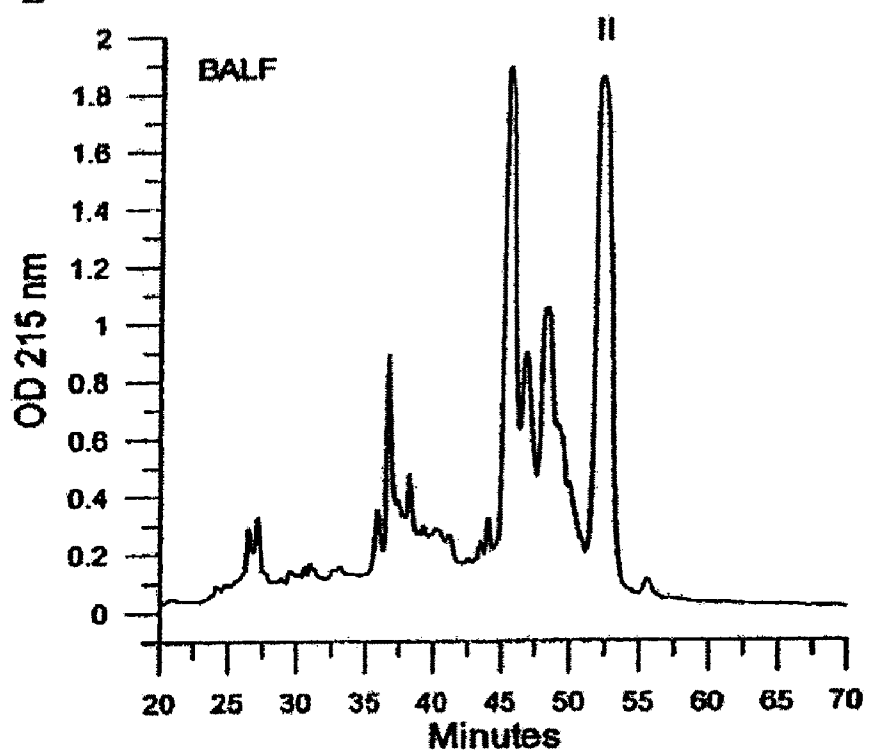

FIG. 38 shows HPLC reverse phase column chromatograms of serum protein and BALF protein. Both serum and BALF proteins were partially purified from MonoQ chromatography (FIGS. 35 and 36) and applied to the reverse phase HPLC. Protein I and Protein II represent the fractions that showed SFA activity and $PLA_2$-s activity, respectively.

Figure 39:
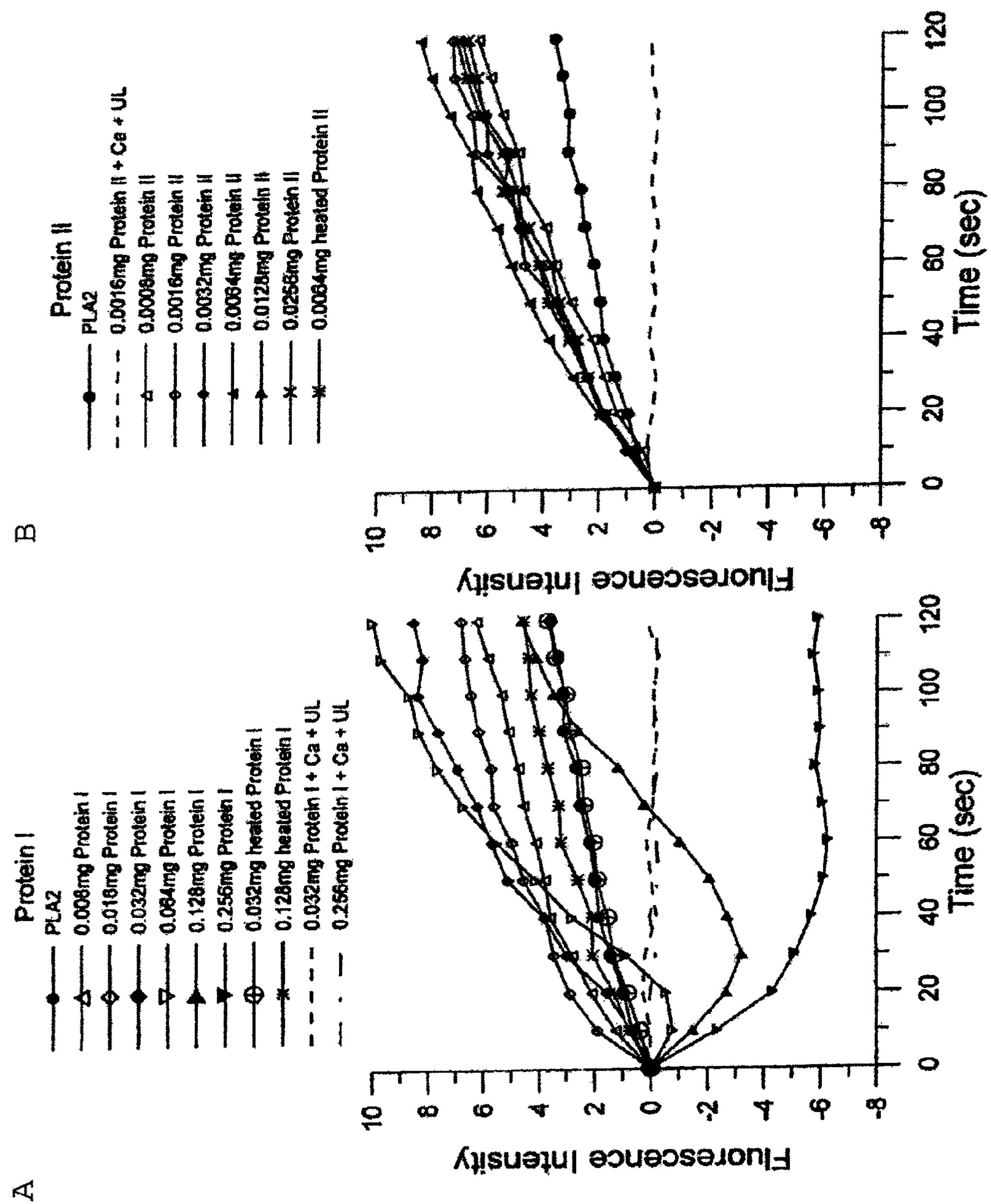

FIG. 39 shows effects of purified serum Protein I and Protein II on pancreatic $PLA_2$ activity using the fluorescent assay.

Figure 40:
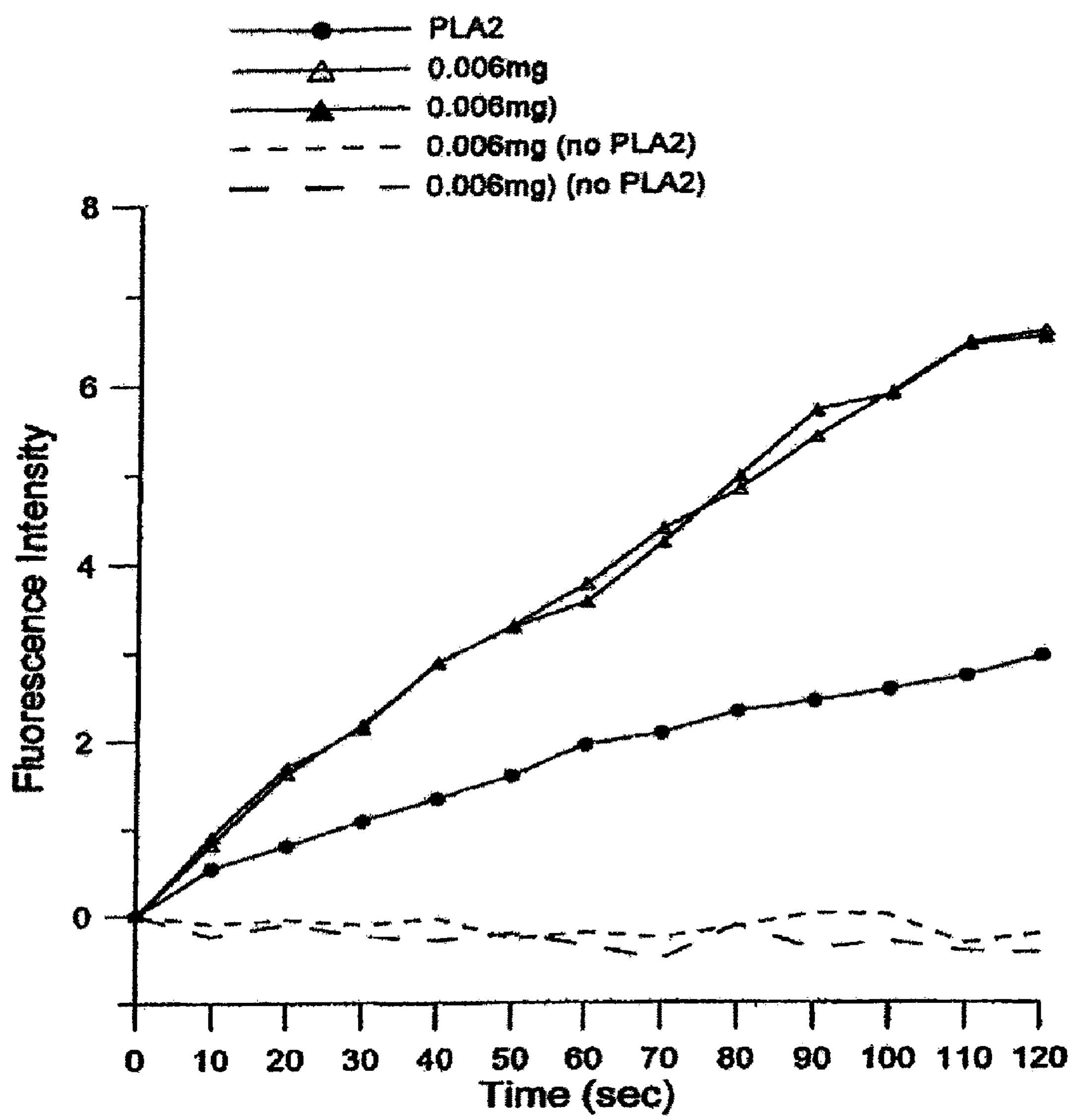

FIG. 40 shows effect of Protein II isolated from CF BALF using the fluorescent assay.

Figure 41:
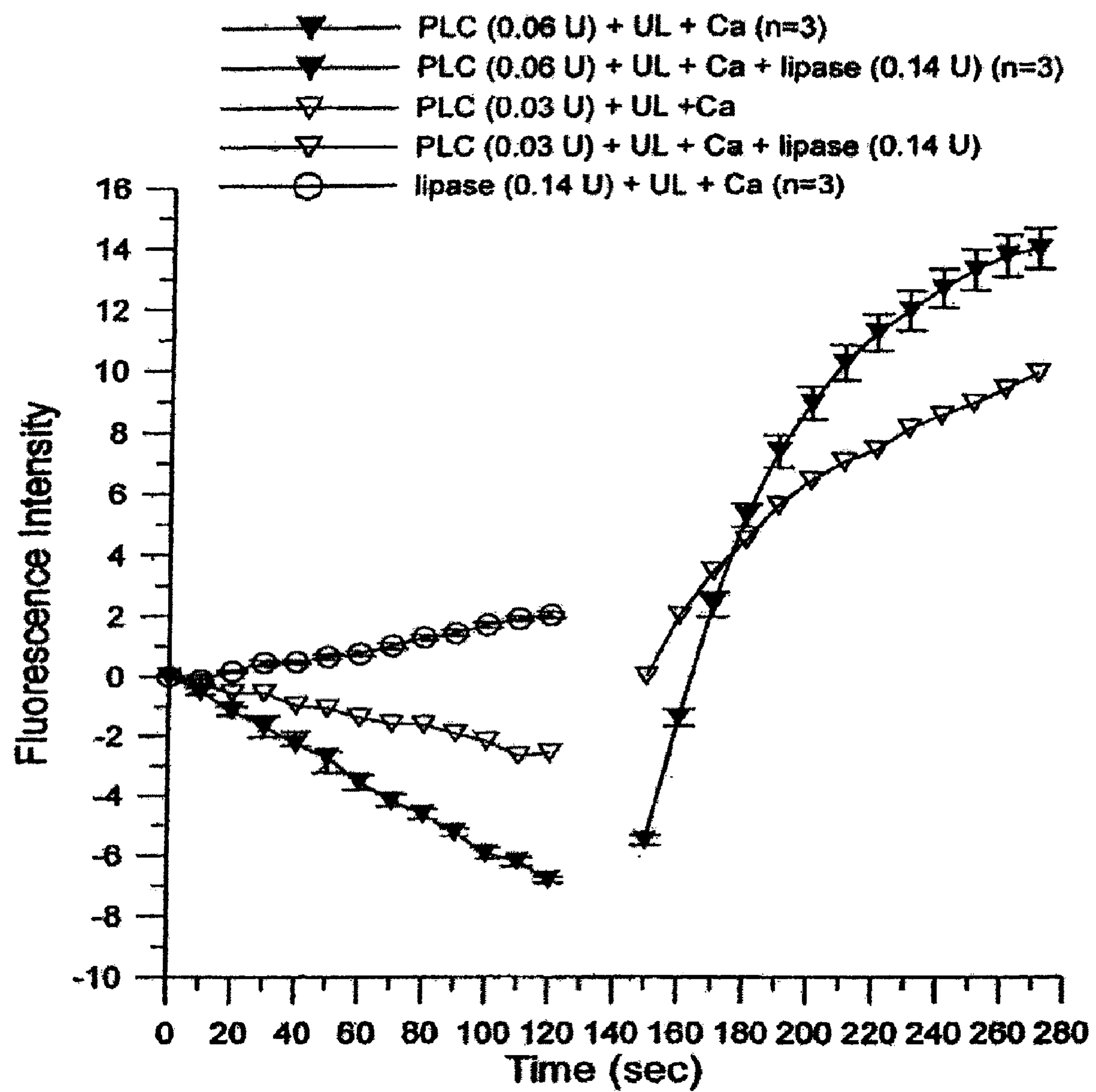

FIG. 41 shows results of a fluorescent assay of PLC and lipase. The PLC assay was the same as $PLA_2$ assay, except $PLA_2$ was replaced by PLC, and conducted at room temperature. PLC activity was determined for 2 min followed by adding an amount of lipase to the same reaction mixture and the fluorescent intensity was continuously determined for another 2 min.

Figure 42:
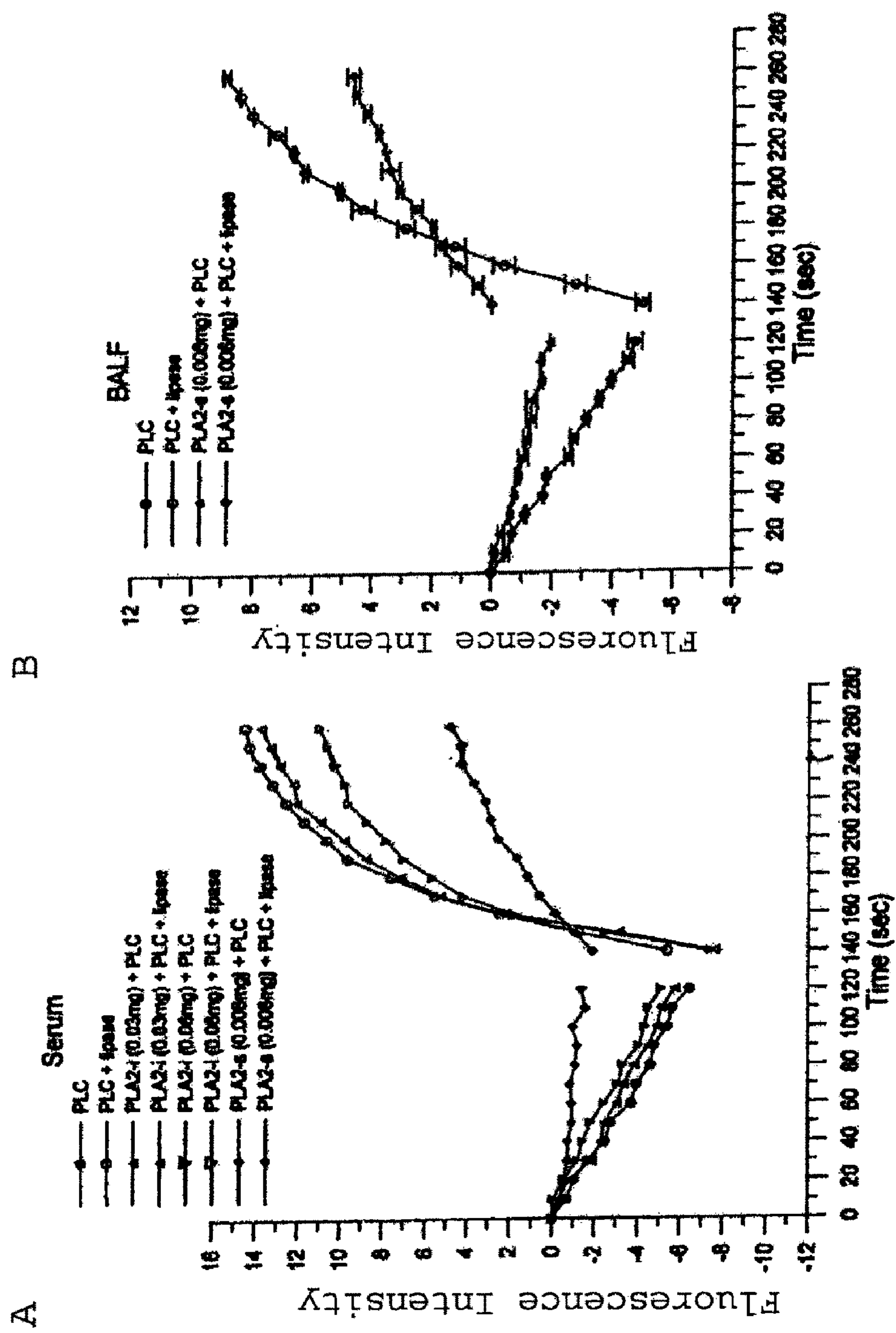

FIG. 42 shows effects of purified serum $PLA_2$-s and SFA and BALF $PLA_2$-s on PLC and lipase activities using the fluorescent assay.

Figure 43:
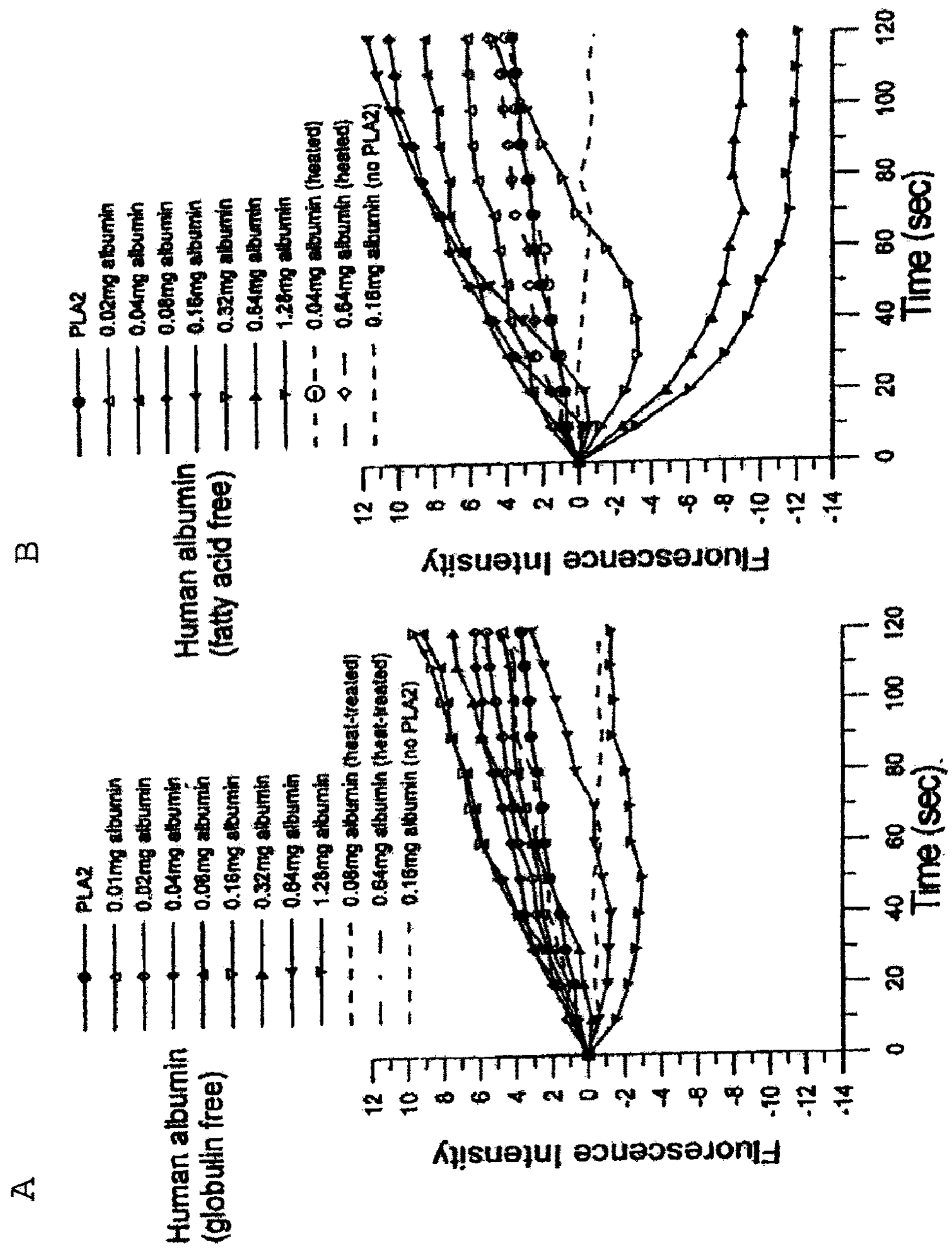

FIG. 43 shows results of a fluorescent assay using human serum albumin obtained from Sigma Chemical Co. Left: globulin-free albumin; Right: fatty acid-free albumin prepared from globulin-free product.

Figure 44:
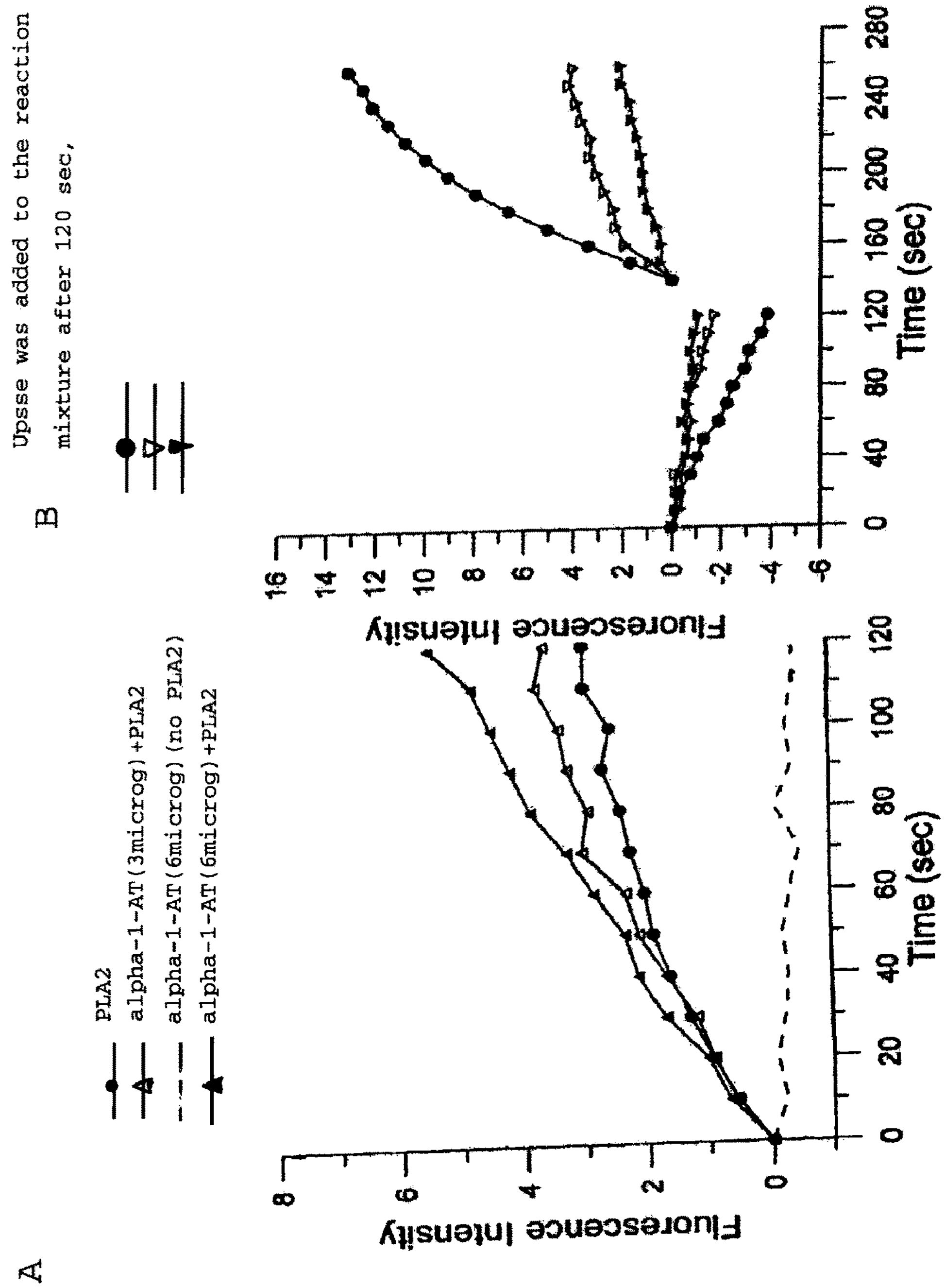

FIG. 44 shows effects of intact $\alpha$1-AT on pancreatic $PLA_2$ activity (A) and on PLC and lipase activities (B) using the fluorescent assay.

Figure 45:
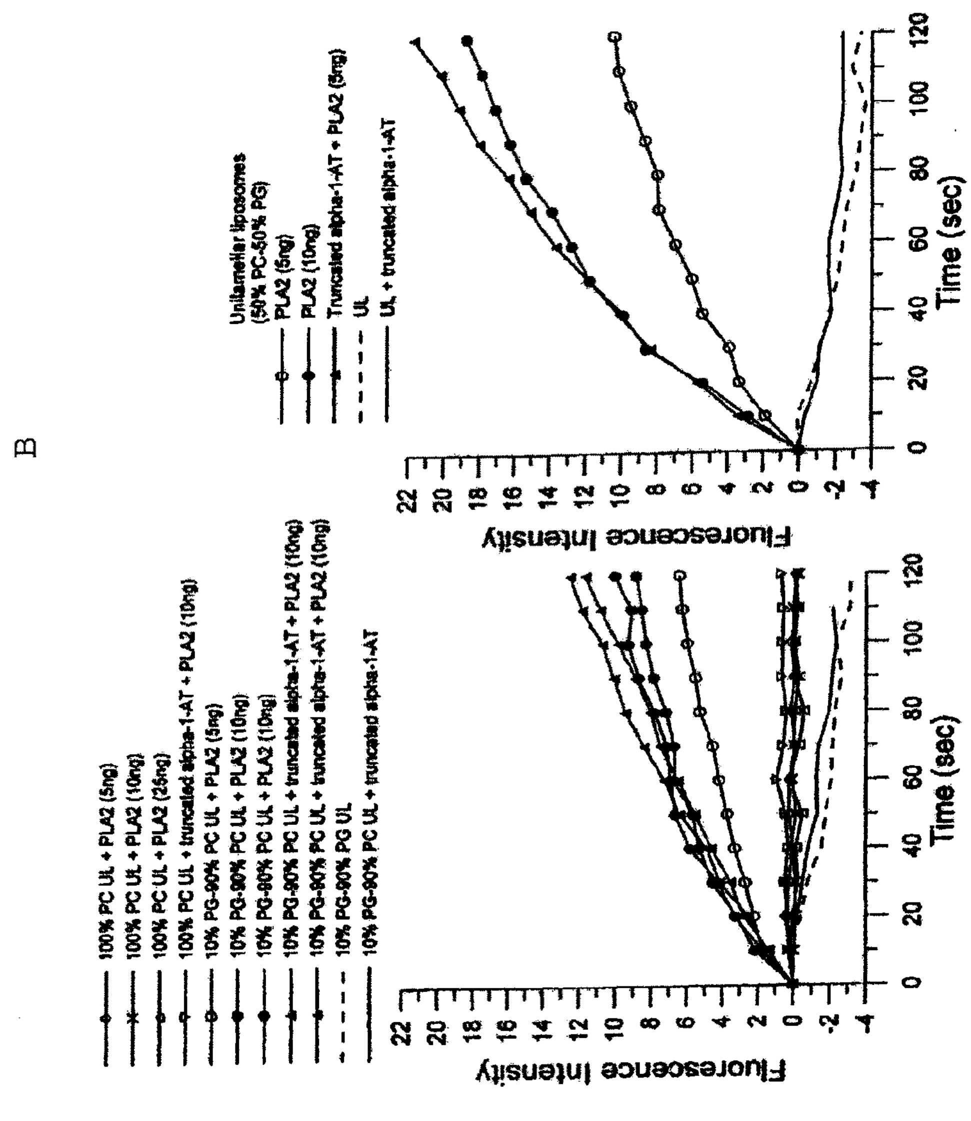

FIG. 45 shows effects of truncated $\alpha$1-AT on $PLA_2$ with different charged unilamellar liposomes (UL) using the fluorescent assay. The assay was conducted at 37° C. The amount of truncated $\alpha$1-AT was 6 μg.

Figure 46:
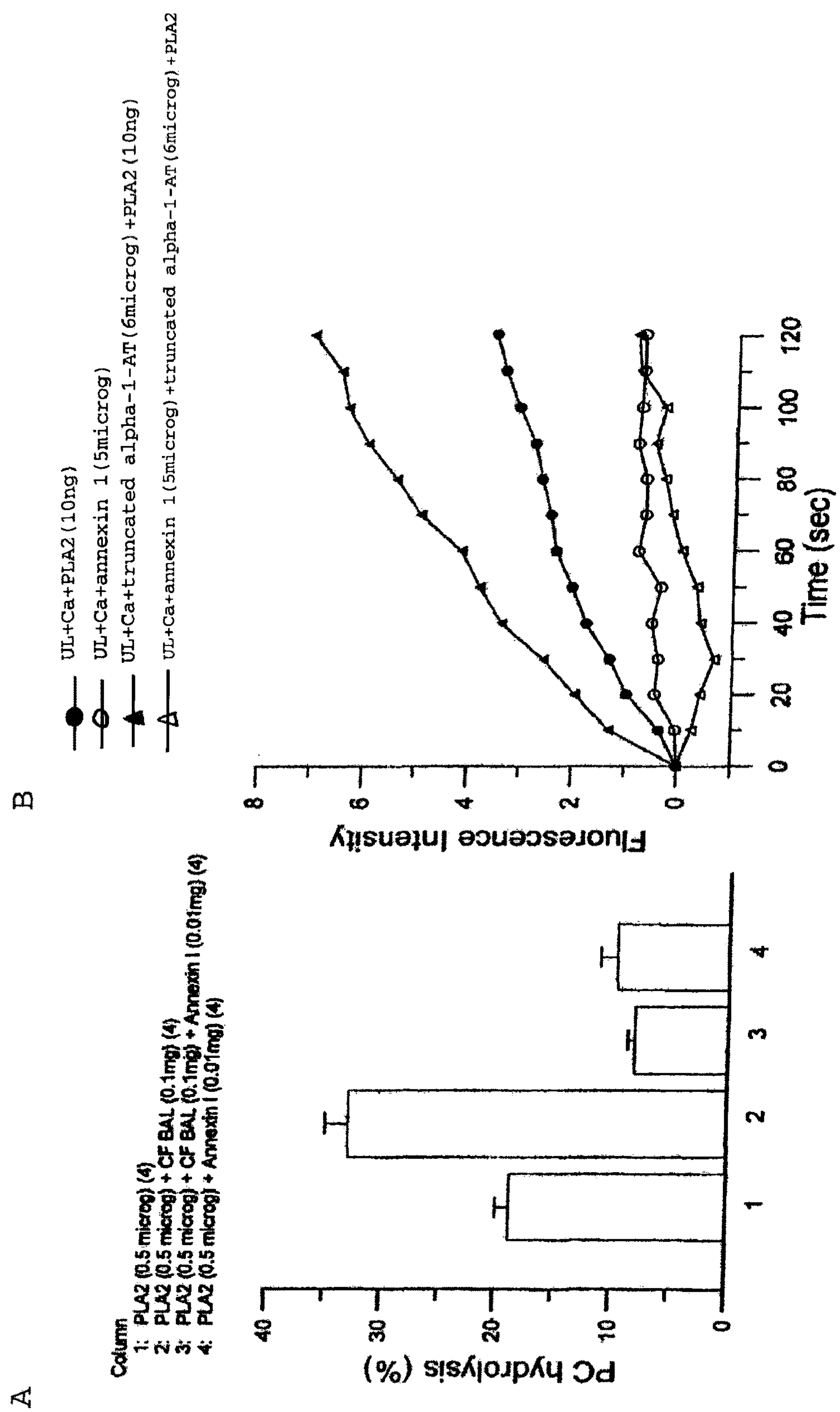

FIG. 46 shows effects of annexins on $PLA_2$ and BALF $PLA_2$-s activities. (A) Results of the effects of annexins on CF BALF $PLA_2$-s activity was determined by the radioactive method shown in U.S. Pat. No. 6,180,596. (B) Effect of annexin on $PLA_2$-s activity of truncated $\alpha$1-AT from CF BALF was determined by the fluorescent assay.

Figure 47:
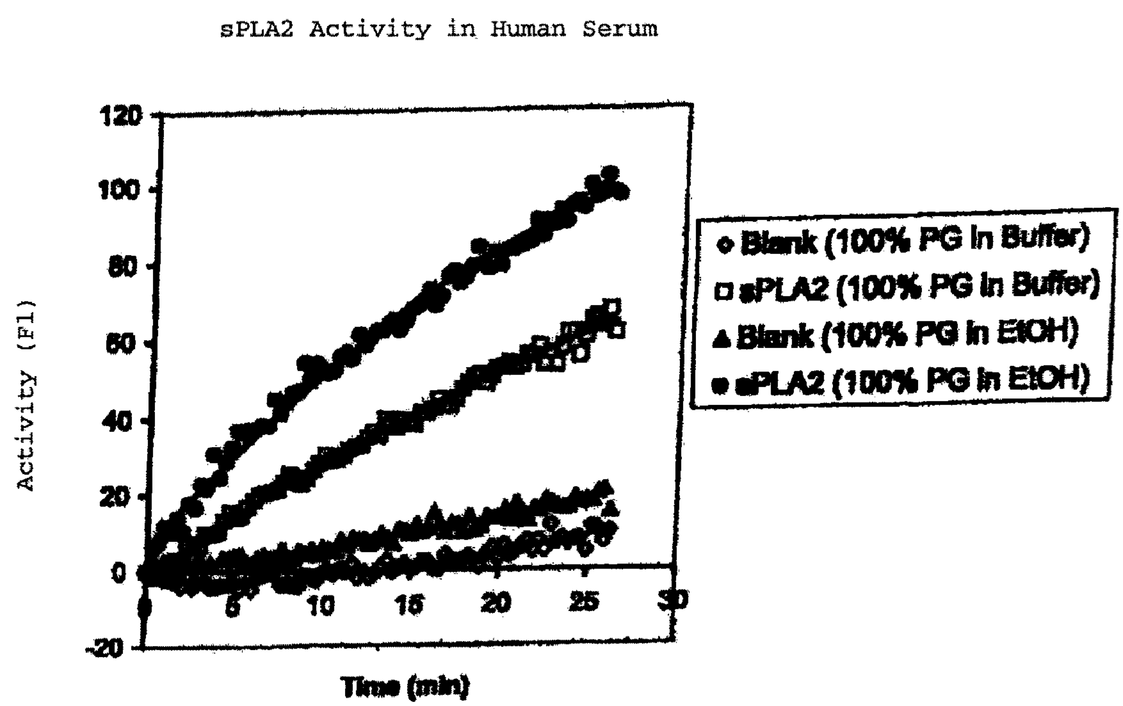

FIG. 47. Comparison of the sPLA2-IIA activity in human serum with using 100% PG-BODIPY-PC in ethanol (EtOH) and 100% PG-BODIPY-PC liposomes in buffer as substrates. The amount of sPLA2-IIA in serum was 0.5 ng/μl serum. The time course of the sPLA2 activity was determined by the microplate fluorescent method (Tsao F H C, et al. *Clin Chim Acta* 2007; 379:119-126.).

Figure 48:
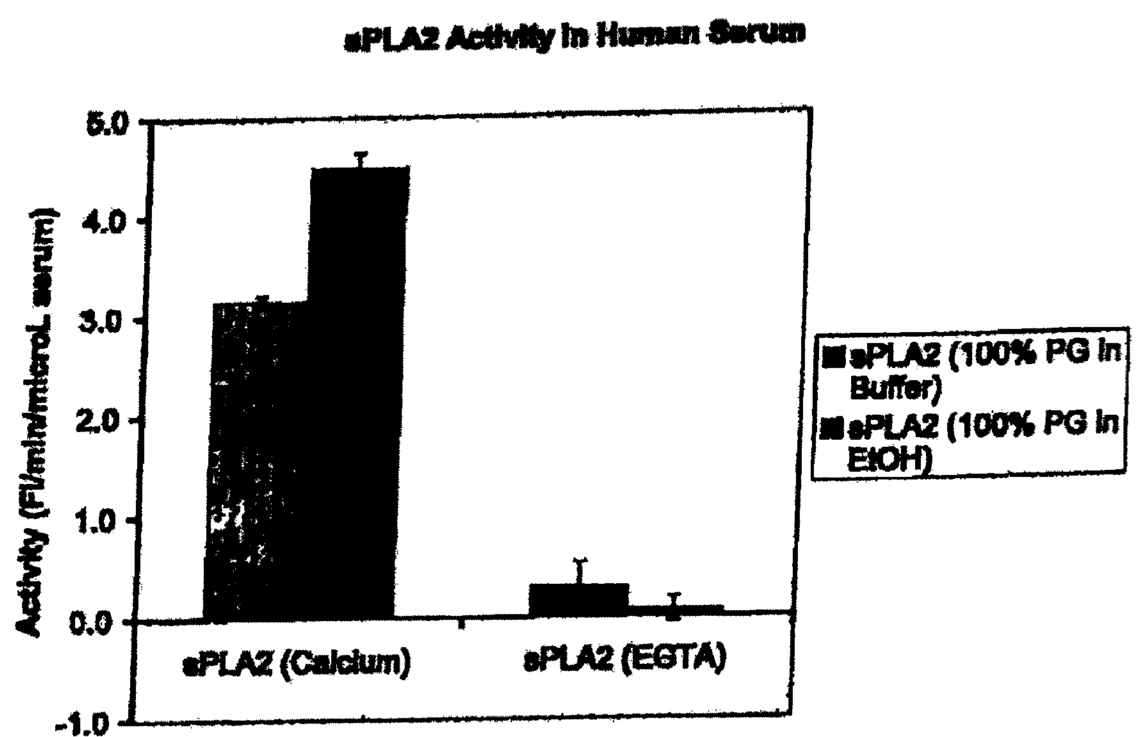

FIG. 48. Comparison of the $sPLA_2$-IIA activity in human serum with using 100% PG-BODIPY-PC in ethanol (EtOH) and 100% PG-BODIPY-PC liposomes in buffer as substrates. The $sPLA_2$ activity was determined from the initial rate of the FI vs. Time reaction curve of each assay as the example shown in FIG. 46. Each bar represents mean±SEM of triplicate assays.

Figure 49:
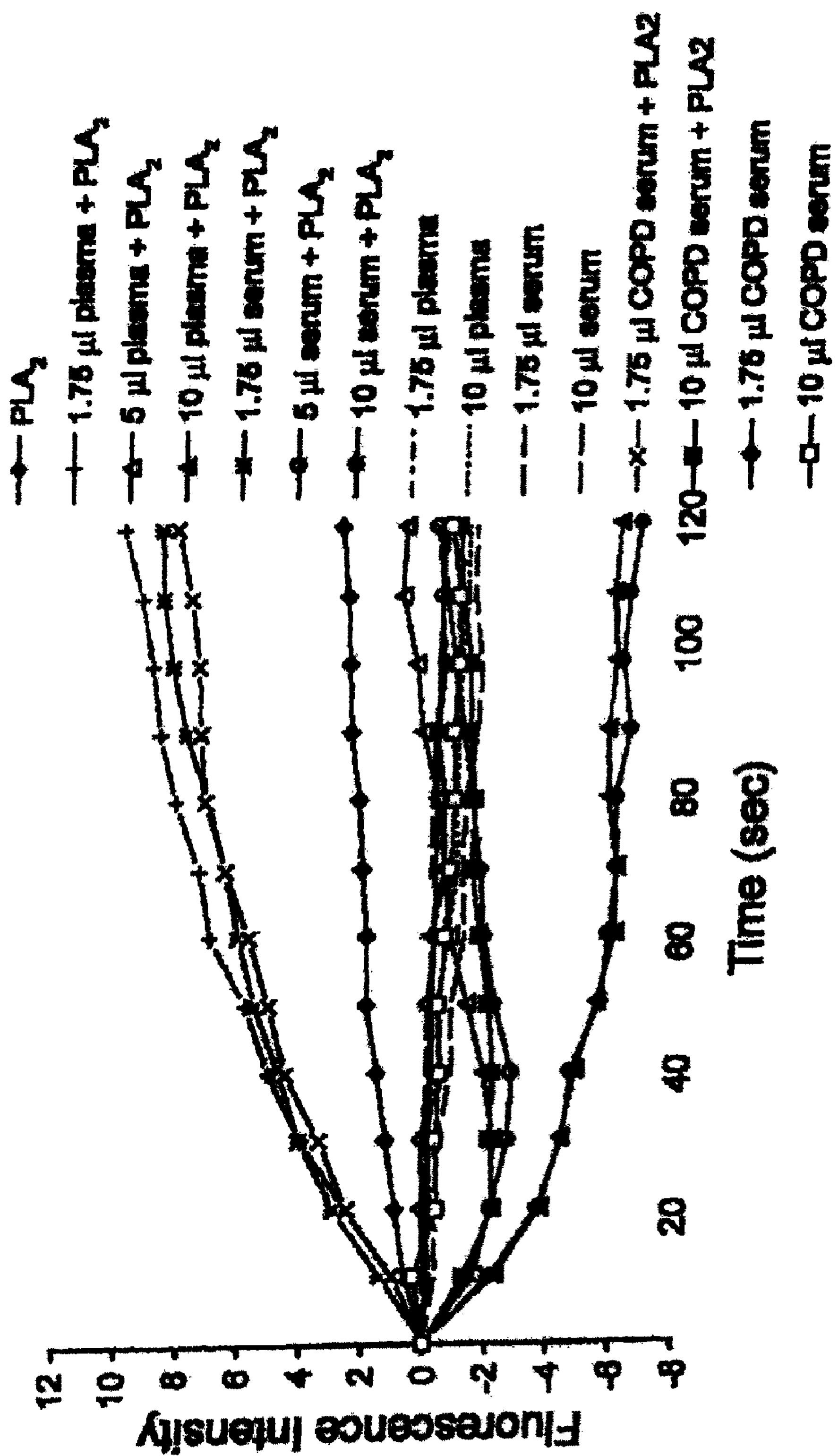

FIG. 49. Effects of plasma or serum on $PLA_2$ activity. $PLA_2$ activity was determined by the fluorescent assay in a 3 ml cuvette at room temperature for 2 min as described in the text. Porcine pancreatic $PLA_2$ was used as the enzyme source. Representative effects on $PLA_2$ activity are shown by the effect of 1.75, 5, and 10 μl of human plasma or serum in the assay mixture. The effects range from increasing FI (1.75 μl), moderately decreasing FI (5 μl), and markedly decreasing FI into negative values by 10 μl of plasma or serum. In the absence of $PLA_2$, plasma or serum had no significant effect on FI in the reaction mixture as compared to the blank.

Figure 50:
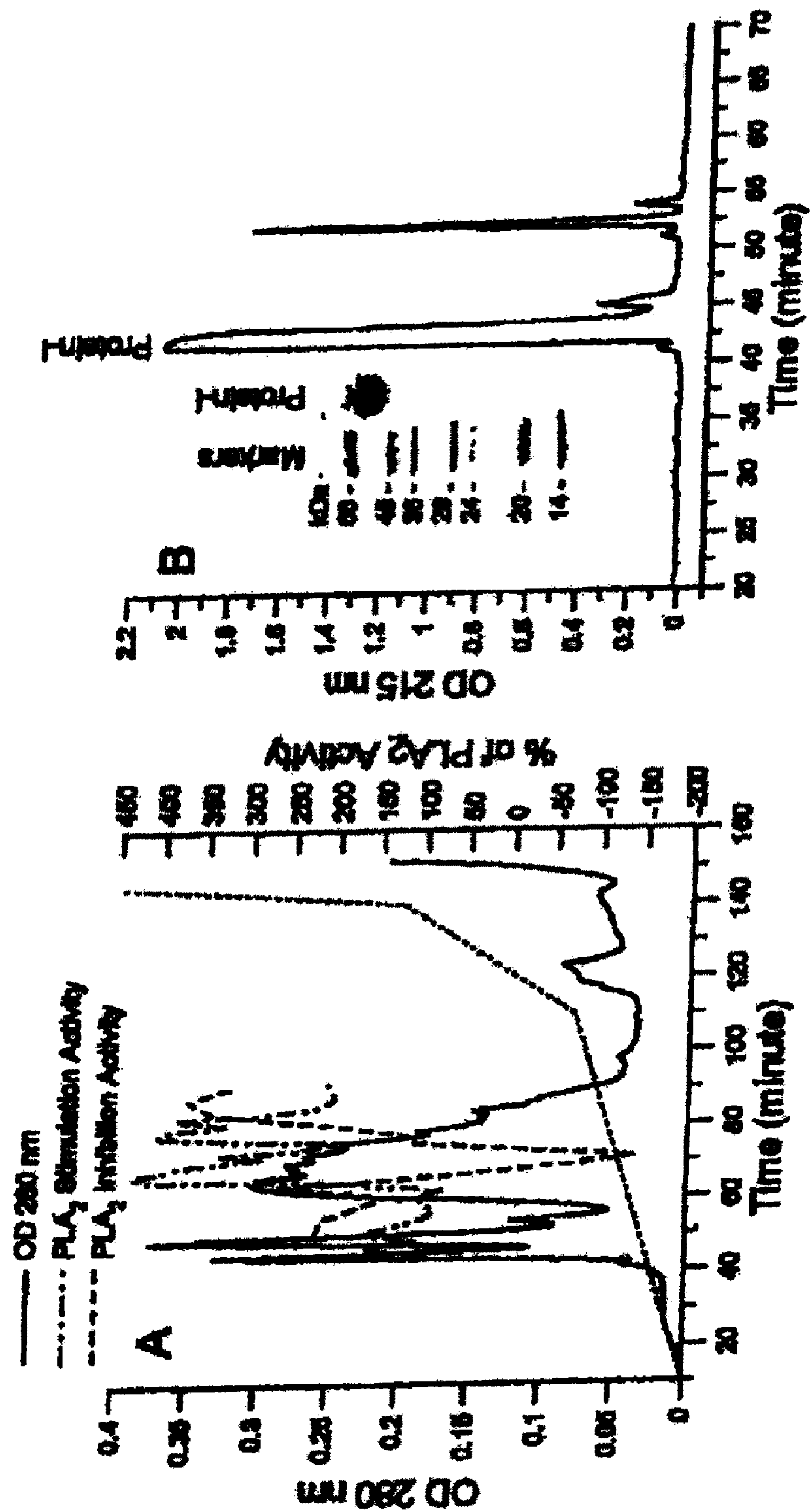

FIG. 50. Isolation of human serum proteins affecting $PLA_2$ activity by anionic exchange MonoQ column chromatography and reverse phase HPLC Vydac C4 column. The MonoQ chromatogram (A) was obtained from a pool of 10 and 70 kDa proteins obtained from Sephades G100 column chromatography. The MonoQ column was eluted with an ascending NaCl gradient as described in the text. The pool of fractions eluted from MonoQ column between 65 and 80 min (A) was used as the protein source for the reverse phase HPLC Vydac C4 column chromatography (B). The purity of Protein-I eluted between 42 and 45 min from Vydac C4 column was analyzed by SDS gel electrophoresis (FIG. 50B, insert).

Figure 51:
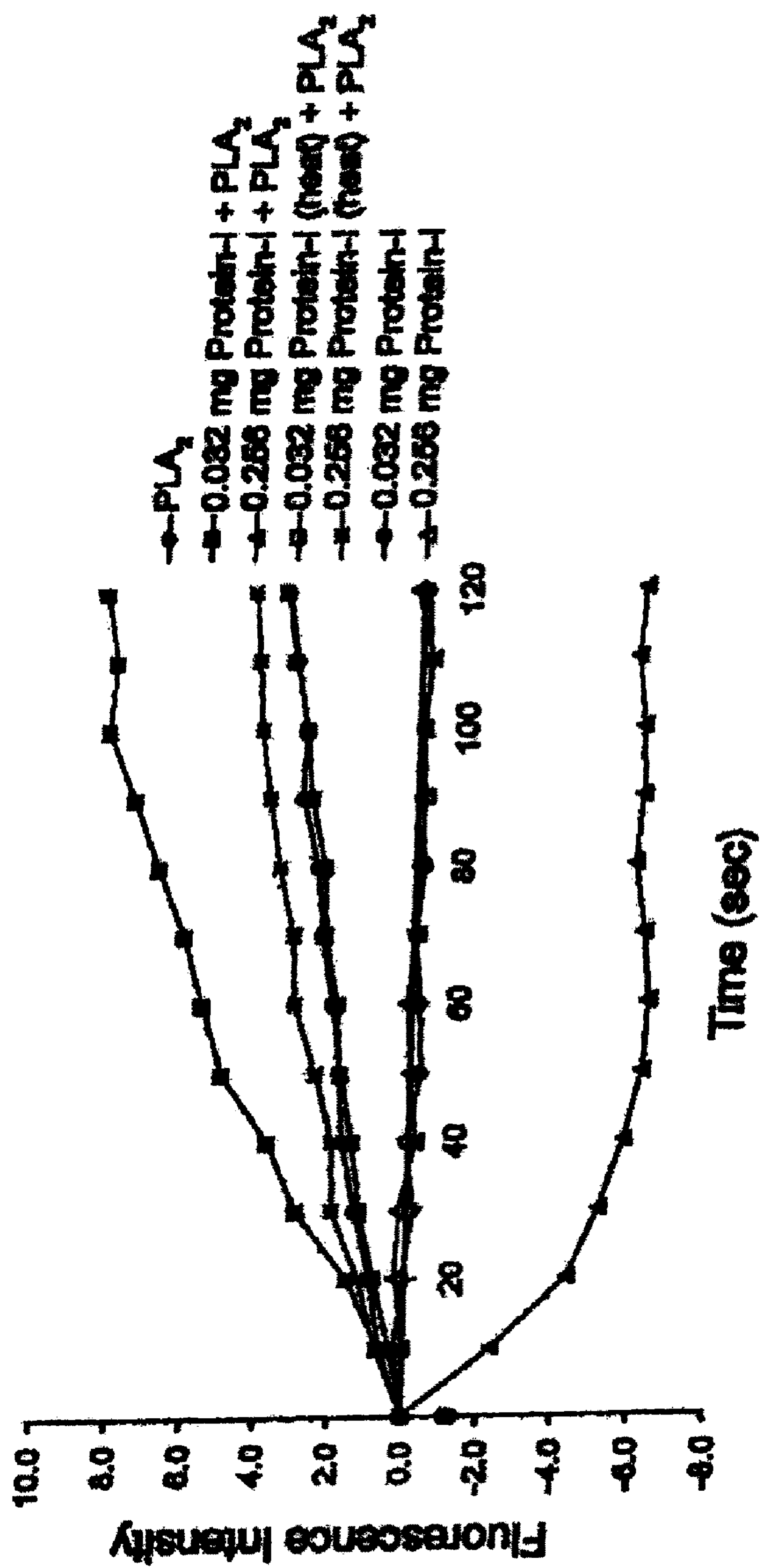

FIG. 51. Effects of Protein-I on $PLA_2$ activity. $PLA_2$ activity was determined by the fluorescent assay in a 3 ml cuvette at room temperature for 2 min in the absence or presence of Protein-I isolated from Vydac C4 column. In the absence of $PLA_2$, Protein-I had no significant effect on FI in the reaction mixture. Protein-I exhibited both $PLA_2$-s (low Protein-I concentration) and SFA (high Protein-I concentration) effects. Protein-I treated in boiling water diminished all the effects.

Figure 52:
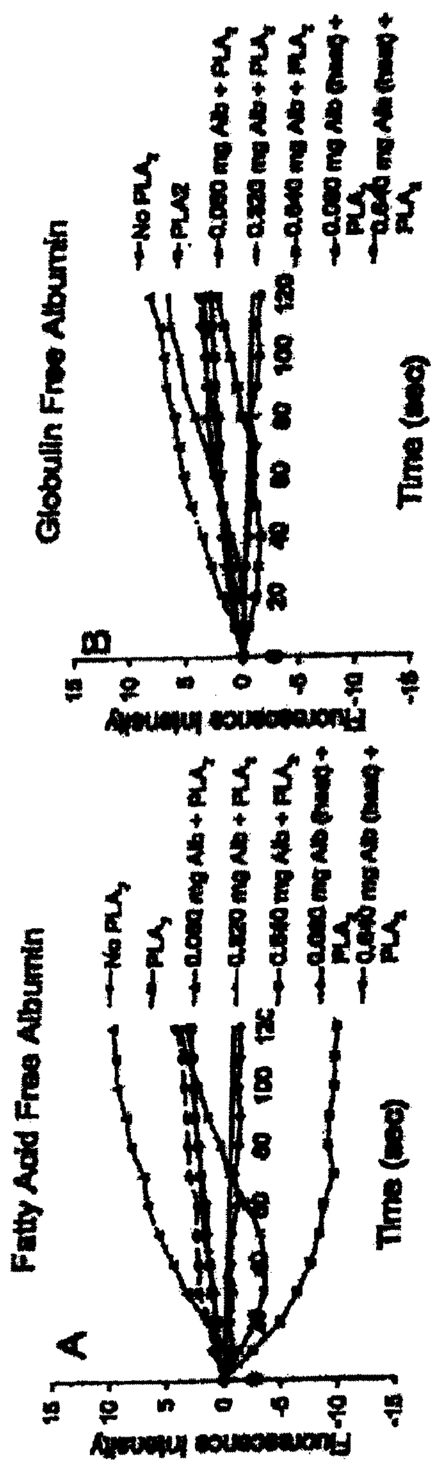
Figure 52:
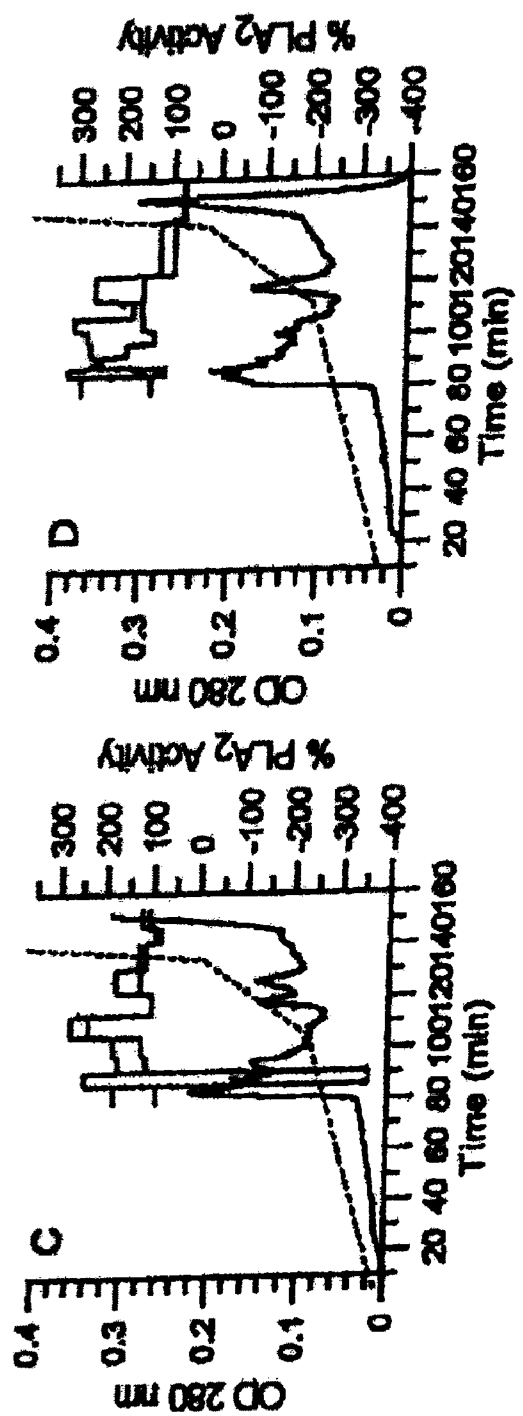

FIG. 52. Effects of fatty acid-free albumin and globulin-free albumin on $PLA_2$ activity. The effects of commercial fatty acid-free and globulin-free albumins on pancreatic $PLA_2$ activity were tested with using three albumin concentrations (0.08, 0.32, and 0.64 mg) in 3 ml assay mixture. Both fatty acid-free and globulin-free albumins stimulated $PLA_2$ activity similarly at low albumin concentrations, but only fatty acid-free albumin had similar $PLA_2$ inhibitory effects as serum, plasma, and Protein-I at high albumin concentrations (A and B). FIGS. 52C and D are MonoQ chromatograms of fatty acid-free albumin (10 mg/0.5 ml applied to the column) (C) and globulin-free albumin (10 mg/0.5 ml applied to the column) (D). The effects of the MonoQ fractions on PLA2 activity were determined with two concentrations, 0.08 mg (blue lines) and 0.64 mg (red lines) in 3 ml assay mixture.

Figure 53:
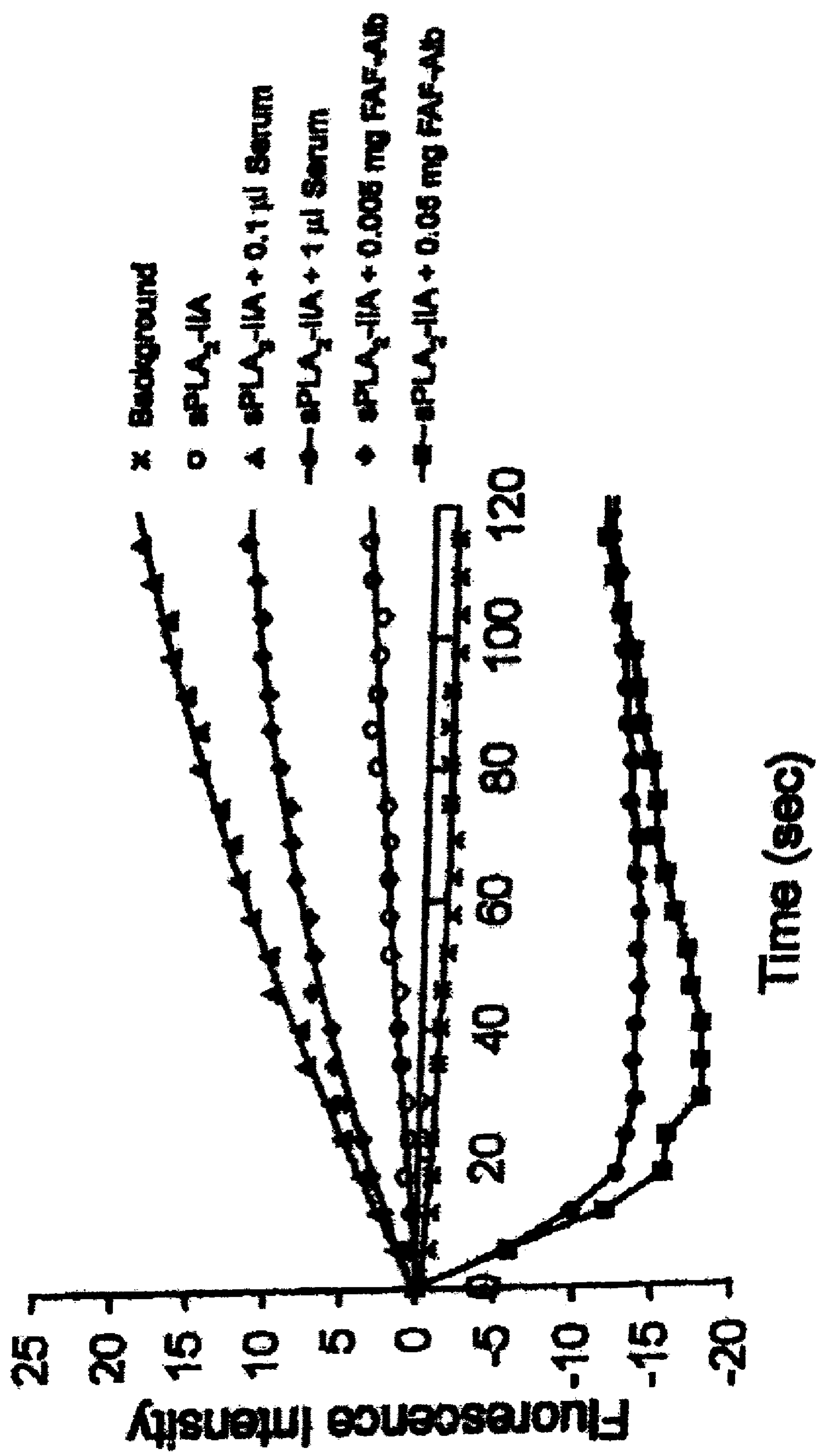

FIG. 53. Effects of serum and albumin on recombinant human sPLA$_2$-IIA activity in microplate assay. sPLA2-IIA assay was conducted in microplate well with a reaction volume of 0.3 ml containing BODIPY-PC labeled liposome substrate as previously described (26) in the absence or presence of serum or fatty acid-free (FAF) albumin. The amount of serum (0.1 or 1 μl) or albumin (0.005 or 0.05 mg) in the microplate assay was $1/10^{th}$ of that employed in the pancreatic PLA$_2$ 3 ml cuvette assay.

Figure 54:
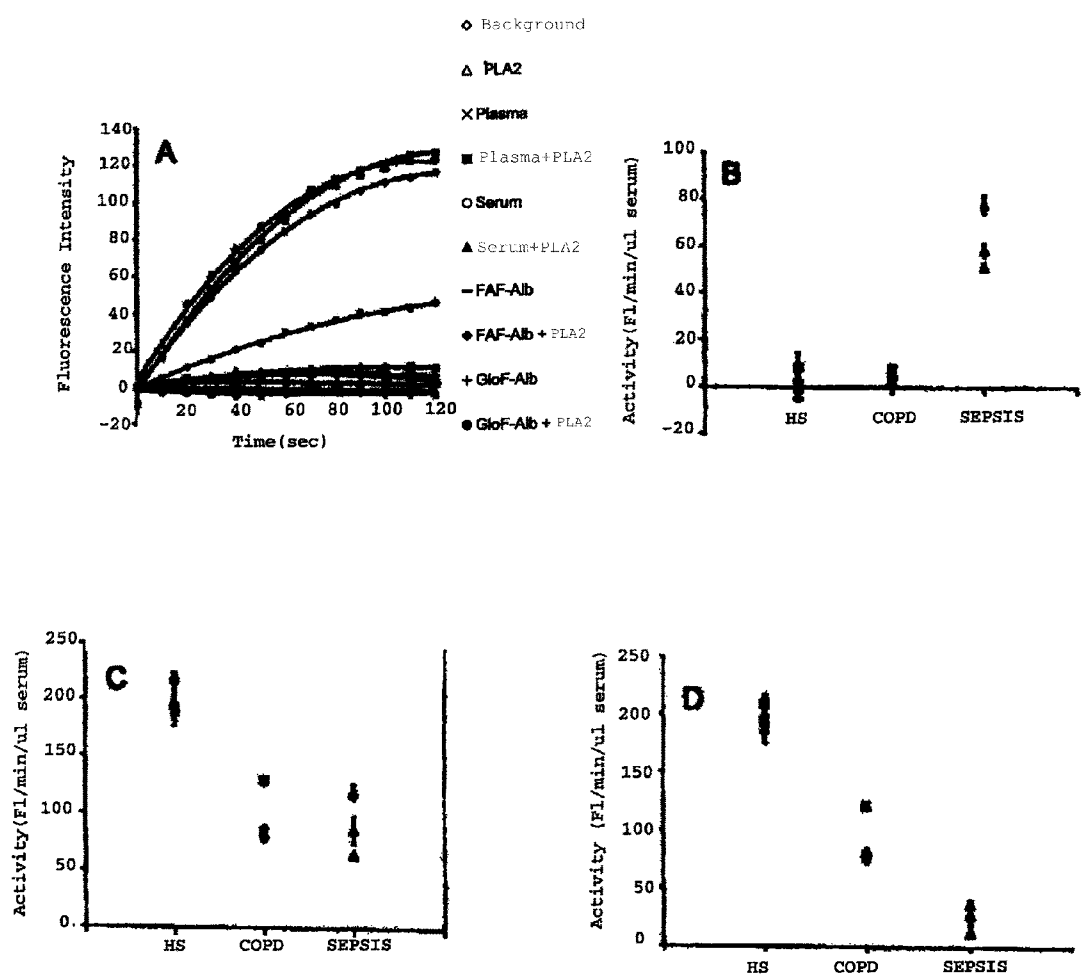

FIG. 54. Determination of the PLA$_2$ activity with using BODIPY-FA labeled liposome substrate and the effects of specific fraction of albumin in serum from healthy subjects and subjects with COPD and sepsis. The assay was conducted in microplate well with a reaction volume of 0.3 ml containing 10 mM $Ca^{2+}$ and BODIPY-FA-labeled liposome substrates, similar to the assay conditions described in FIG. 53. Pancreatic PLA$_2$, serum from healthy subject, or albumin alone in the reaction mixture had little effect on FI as compared to the blank. FI in the reaction mixture containing both PLA$_2$ and serum, or PLA$_2$ and fatty acid-free (FAF) albumin markedly increased during the 2 min of reaction that was much higher than the FI generated from the reaction containing PLA$_2$ and globulin-free albumin (A). FIG. 54B represents the initial rates obtained from the reactions containing BODIPY-FA-labeled liposomes and serum in the absence of PLA$_2$. FIG. 54C represents the initial rates obtained from the reactions containing BODIPY-FA-labeled liposomes, pancreatic PLA$_2$, and serum. FIG. 54D represents the difference between the initial rate (B) and initial rate (C) in each serum sample.

Figure 55:
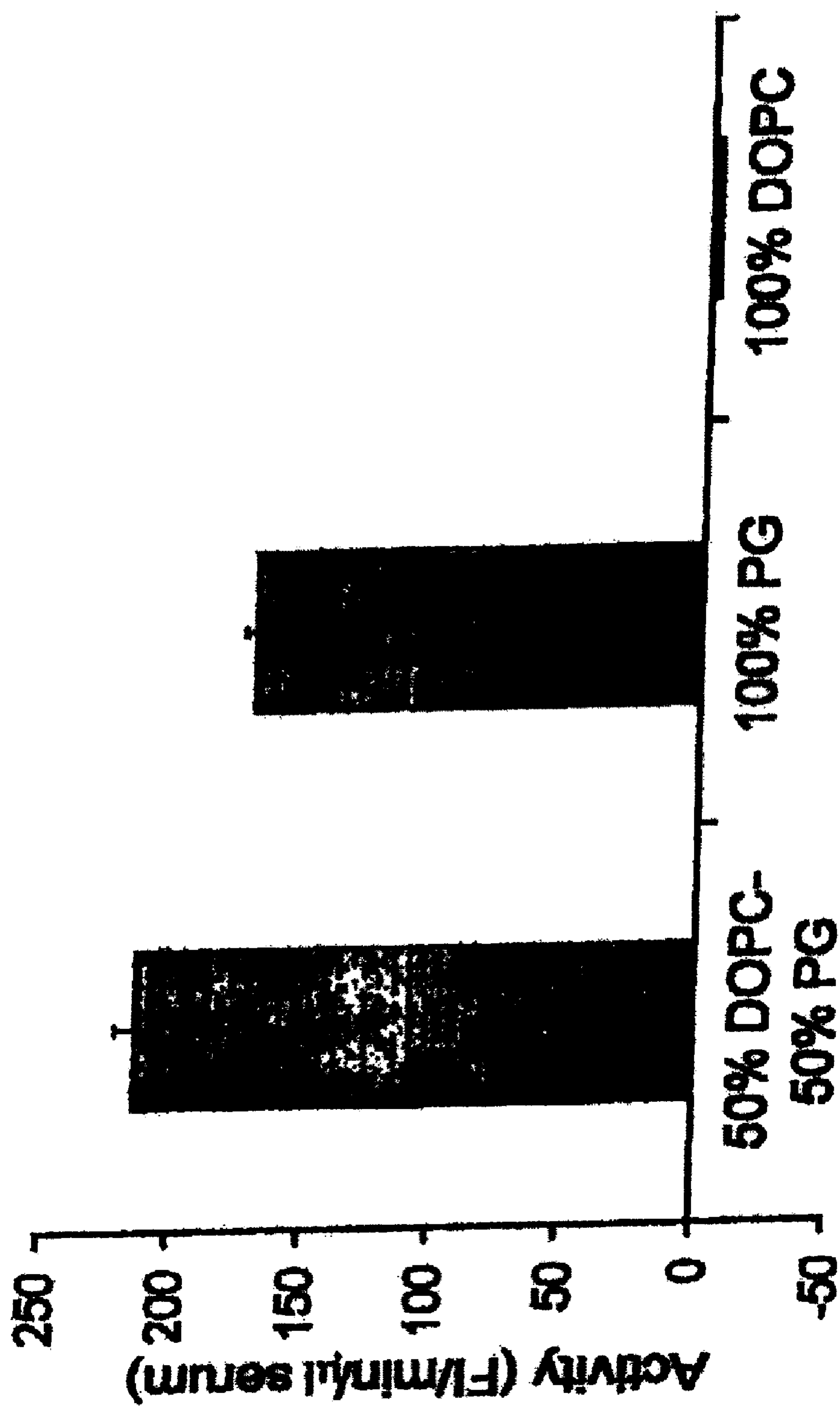

FIG. 55. Effect of substrate phospholipid compositions on SFA activity. Three groups of substrates with different phospholipid compositions were used for determining the SFA activity. Substrate composed of 50% DOPC and 50% PG provided the highest SFA activity, next was 100% PG substrate. SFA was completely inactive with using 100% DOPC as substrate.

DETAILED DESCRIPTION OF THE INVENTION

The present invention provides novel methods of detecting, monitoring and preventing PLA2-mediated inflammation.

I. In General

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

A. In one embodiment, the present invention provides a method of measuring the activity of a specific fraction of albumin (SFA) in a mammalian subject such as a human. The method comprises providing a liposome comprising a fluorescently-labeled carboxylic acid and a negatively-charged phospholipid; mixing the liposome with phospholipase A$_2$ and a biological test sample from the subject; measuring a change in fluorescence intensity at defined intervals over a specific period of time to determine the SFA activity in the test sample; and comparing the SFA activity in the test sample to SFA activity in a control sample. The liposome may further comprise phosphotidylcholine (PC), wherein the PC is dioleoyl PC (DOPC).

In a preferred embodiment, the subject is human, and the biological sample is selected from the group consisting of plasma, serum, bronchoalveolar lavage fluid, sputum, urine, synovial fluid, amniotic fluid, peritoneal fluid, white blood cells, alveolar macrophages, cerebrospinal fluid, pleural fluid, and pericardial fluid.

The negatively-charged phospholipid is preferably selected from phosphatidylglycerol (PG), phosphotidylcholine (PC), phosphatidylserine (PS), phosphatidylinositol (PI), phosphatidic acid (PA), a PG/PC mixture, and combinations thereof. A preferred example of the negatively-charged phospholipid is phosphatidylglycerol (PG), although a PG/PC mixture is also preferred.

In a preferred embodiment, the fluorescently-labeled carboxylic acid is a fatty acid having a hydrocarbon chain length from about 6 to 18 carbons, such as 4,4-difluoro-5-methyl-4-bora-3a,4a-diaza-s-indacene-3-dodecanoic acid (BODIPY-FA). For instance, in a preferred embodiment, the liposome comprises 4,4-difluoro-5-methyl-4-bora-3a,4a-diaza-s-indacene-3-dodecanoic acid (BODIPY-FA), phosphatidylglycerol (PG), and dioleoyl PC.

The inventors observed that when a serum sample from a mammalian subject is added to the assay system, the fluorescence intensity (FI) increases. However, the FI increases more with serum from healthy individuals and increases less with serum from individuals having an inflammatory reaction. Serum from individuals having severe inflammation showed a very small FI increase.

The inventors further observed that human serum fatty acid-free albumin caused a similar FI increase while globulin-free albumin caused a much lower FI increase. Albumin is the most abundant protein in plasma/serum and it is a heterogeneous, 66 k-Da single polypeptide comprising multiple sub-molecular species due to its association with various ligands and state of oxidation. Plasma or serum albumin has been implicated in inflammation through PLA$_2$-induced albumin-membrane interaction (see, for example, US patent application publication number 2003/0219849, incorporated herein by reference for all purposes). Without intending to be limited by theory, the inventors believe that the method of the present invention accurately detects PLA$_2$ activity in a sample because the FI increases when PLA$_2$ induces a subset of albumin in the sample to bind to the liposomal membrane and release the fluorescently-labeled fatty acid from the liposome.

In a preferred embodiment, the carboxylic acid employed to practice the present invention is a fatty acid. Fatty acid is a carboxylic acid with an either saturated or unsaturated hydrocarbon chain having a length of about 4 or more carbons. Typically, the hydrocarbon chain is unbranched, although branched hydrocarbons are also feasible.

In a preferred embodiment, the liposome comprises PG, PC, and C1-BODIPY-C12-FA. However, one of ordinary skill in the art can readily determine which other combinations of phospholipids(s) and carboxylic acid(s), to the extent not specifically disclosed herein, can be used to form a liposome for practicing the present invention. The liposome of the present invention is preferably but does not have to be unilamellar.

In the method of the present invention, the SFA activity in a sample can be determined based on fluorescence data collected at a single time point or recorded on a continuous basis. The latter provides more reliable results because potential bias due to idiosyncrasies of particular time points can be avoided. Continuous recordation allows the FI to be recorded more accurately. For instance, the initial rate of the reaction may be much higher than at a later point in the reaction. Accordingly, continuous recordation more accurately reflects SFA activity.

In another aspect, the present invention relates to a method for assessing whether a mammalian subject such as a human subject has or is at risk of developing inflammation (e.g., systemic inflammation) or an inflammation-related disorder (e.g., COPD, CF, bacterial or viral infection, sepsis, and trauma such as head trauma) by determining whether a subject has a decreasing or abnormally low SFA activity. In this regard, the SFA activity in a biological sample from the subject is measured according to the method of the present invention and then compared to (i) the SFA activity from the same subject measured at an earlier time; or (ii) a normal range of SFA activity obtained from healthy subjects of the same species.

For a particular type of biological sample, the normal SFA activity range can be determined by analyzing biological samples from a suitable number of healthy individuals. For example, at least 10, 20, 30, 50, or 100 healthy individuals are analyzed to determine the normal SFA activity range. In a typical example, a normal SFA activity range in a healthy individual is 198.73±4.05 (n=7) (FI/min/μl serum). In contrast, the SFA activity range in an individual suffering from COPD is 93.03±14.12 (n=3) (FI/min/μl serum). The SFA activity range in an individual suffering from sepsis is 25.56±12.47 (n=3) (FI/min/μl serum), while the SFA activity range in a smoker is 189.68±12.26 (n=4) (FI/min/μl serum).

In one embodiment, the SFA activity of the subject is compared to a normal range of SFA activity obtained from healthy subjects of the same species. A lower than normal SFA activity indicates that the subject has inflammation (e.g., systemic inflammation when plasma or serum is the biological sample). For instance, a SFA activity 1%-70% lower, preferably 5%-60% or 10%-50% lower than normal would indicate the subject has moderate to severe inflammation.

In another embodiment, the above method is used for determining whether a human subject who is a tobacco smoker has developed or is about to develop chronic obstructive pulmonary disease (COPD) by monitoring the SFA activity of the subject. A decrease in SFA activity over time indicates that the subject has developed or is about to develop COPD. The amount of decrease in SFA activity that is indicative of the onset of COPD varies, but will be understood by one of skill in the art. Smokers are at risk of developing COPD and monitoring SFA activity over time can provide early detection of COPD. In a typical example, a subject's SFA activity is measured at least once a month for at least one year. A continuous decline (regardless of the rate of decline) would indicate the development of COPD.

In another embodiment, the SFA activities of a mammalian subject such as a human subject who undergoes a surgical procedure are measured before and after the surgery, wherein a decrease in SFA activity after the surgery indicates that the subject has inflammation, such as that caused by an infection. In a typical example, a subject's SFA activity is measured at least every twelve hours. A continuous decline (regardless of the rate of decline) would indicate the development of sepsis or other inflammation disorder.

In another aspect, the present invention provides a kit for measuring SFA activity. The kit contains a fluorescently-labeled carboxylic acid such as an FA as described above, a negatively-charged phospholipid as described above, $PLA_2$, and an instruction manual on how to measure SFA activity in a biological sample from a mammalian subject according to the method disclosed herein. In one embodiment, the fluorescently-labeled carboxylic acid and the negatively-charged phospholipid are provided in the form of a liposome comprising the two.

Optionally, the kit can contain a control sample. The control sample is a sample that has a known level of SFA activity. Examples of control samples include but are not limited to biological samples from a mammalian subject as described herein that has a known level of SFA activity. The subject can be a healthy subject or a subject with an abnormal condition described herein.

The instruction manual can be provided in the form of a publication, a recording, a diagram, or any other medium of expression which is suitable for communicating to a user how to measure SFA activity in a biological sample from a mammalian subject according to the method disclosed herein. The instruction manual of the kit can, for example, be affixed to a container containing the components of the kit or be shipped together with or separately from the container.

B. In another embodiment, the present invention provides a new fluorescent assay for measuring the activity of a phospholipase enzyme. Using the assay of the present invention, the inventors successfully detected $PLA_2$ stimulating and inhibiting activities in a variety of biological samples collected from healthy individuals and individuals suffering from inflammation symptoms. The inventors further identified that the $PLA_2$ stimulating activity is from either albumin or α1-AT and the $PLA_2$ inhibiting activity is from a specific fraction of albumin (SFA). While it was known that albumin inhibits or stimulates $PLA_2$ activity, depending on the assay conditions (32), the inventors have now discovered that α1-AT acts as a new $PLA_2$ stimulator and only the specific fraction of albumin (SFA), but not other albumins, acts as a $PLA_2$ inhibitor.

SFA acts as a $PLA_2$ stimulator at low concentrations by relieving product inhibition. However, at high concentrations, the inventors have shown that SFA acts as a $PLA_2$ inhibitor. Without intending to be limited by theory, the inventors believe that SFA inhibits $PLA_2$ activity by blocking $PLA_2$'s action on cellular membranes; the inventors further provide evidence that α1-AT stimulates $PLA_2$ activity by binding to the head group of phospholipids (especially negatively charged phospholipids) so that the phospholipid molecules rearrange to a loose form to allow $PLA_2$ penetration and hydrolyzation of the fatty acyl groups.

As shown in the examples below, $PLA_2$ stimulator and inhibitor activities could be detected in the plasma and serum of both healthy individuals and CF or COPD patients with lung inflammation. While the $PLA_2$ stimulator activity for healthy and CF or COPD individuals are about the same, the SFA activity is lower in the CF and COPD patients. When BALF collected from CF and COPD patients were tested for $PLA_2$ stimulator and SFA activities, only stimulator but not SFA activity was detected. The α1-AT in the plasma and serum is the full length $\alpha$1-AT and the stimulator activity in the plasma and serum is a reflection of the total stimulator activity of albumin and $\alpha$1-AT. The stimulator activity in the BALF of the CF and COPD patients is that of a truncated $\alpha$1-AT as only the truncated $\alpha$1-AT was found in the BALF.

CF or COPD patients have higher plasma and serum $\alpha$1-AT levels than healthy individuals but their plasma and serum albumin levels are about the same as healthy individuals. Since albumin is much more abundant in plasma and serum than $\alpha$1-AT, the total $PLA_2$ stimulator activity, which includes that of both albumin and $\alpha$1-AT, are about the same in healthy and CF or COPD individuals. The inventors found that the $PLA_2$ stimulatory and SFA activities of albumin are heat sensitive and the $PLA_2$ stimulatory activity of $\alpha$1-AT is heat resistant. Thus, one can detect the difference in $\alpha$1-AT $PLA_2$ stimulatory activity between healthy individuals and CF or COPD patients by heat inactivating albumin in the plasma and serum.

The new fluorescent phospholipase assay and the identification $\alpha$-AT and SFA as a $PLA_2$ stimulator and inhibitor, respectively, provide new tools for diagnosis and treatment of disorders that are associated with an increase in $PLA_2$ activity in human and non-human animals.

In one aspect, the present invention provides a method of measuring the activity of a phospholipase by using a unique fluorescently-labeled liposome disclosed in the present invention, which contains a nonfluorescent phosphatidylcholine (PC), a nonfluorescent, negatively-charged molecule selected from a negatively-charged phospholipid or a negatively-charged organic compound, and a fluorescently-labeled molecule selected from a fluorescently-labeled PC or a fluorescently-labeled, negatively-charged phospholipid wherein hydrolization of the phospholipid components of the liposome by the phospholipase causes a fluorescence intensity change. The method involves contacting the phospholipase with the liposome and detecting the fluorescence intensity change due to the hydrolization of phospholipid components of the liposome to determine the activity of the phospholipase.

In one aspect, the present invention provides a method of measuring the activity of a phospholipase such as $PLA_2$, phospholipase $A_1$ ($PLA_1$), phospholipase C (PLC), and phospholipase D (PLD). A common feature of all these phospholipases is their ability to hydrolyze PC and negatively-charged phospholipids. For example, $PLA_2$ hydrolyzes the fatty acyl group at the sn-2 position of phosphatidylcholine (PC) and $PLA_1$ hydrolyzes the fatty acyl group at the sn-1 position of PC; PLC hydrolyzes PC to yield 1,2-diacylglycerol and choline phosphate and PLD releases choline from PC to produce phosphatidic acid.

To measure the activity of a phospholipase, the present invention provides a unique liposome that contains a nonfluorescent PC, at least one of a nonfluorescent/negatively charged phospholipid and a nonfluorescent/negatively charged organic compound, and at least one of a fluorescently-labeled PC and a fluorescently-labeled/negatively charged phospholipid, wherein hydrolization of the phospholipid components of the liposome by a phospholipase causes a fluorescence intensity change. The change can be an increase or decrease depending on the particular phospholipase and the specific group labeled in the PC or the phospholipid.

For example, when a liposome that contains dioleoyl phosphatidylcholine (DOPC), phosphatidylglycerol (PG) and fluorescently labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) is used, the action of a $PLA_2$ leads to an increase in fluorescence intensity by releasing the fluorescent group the fluorescence from which has initially been quenched in the liposome. On the other hand, the action of a PLC leads to a decrease in fluorescence intensity by liberating 1,2-diacylglycerols that are more hydrophobic and increase quenching of the fluorescence of the fatty acyl group.

To form a liposome of the present invention, any PC can be used. Examples of PCs that can be used include but are not limited to DOPC, dipalmitoyl PC and PCs with other fatty acyl groups. DOPC is a preferred PC for the purpose of the present invention. PCs obtained from egg yolk, soybean and other sources can all be used. The fluorescently-labeled PC and the non-labeled PC can be the same or different. The exact position at which a PC is labeled is not critical so long as fluorescence intensity changes upon hydrolization of the phospholipid components of the liposome by a phospholipase whose activity is being measured. Examples of fluorescently-labeled PCs that can be used in the present invention include but are not limited to Bis-BODIPY FL $C_{11}$-PC and 1,2-bis-(1-pyrenebutanoyl)-sn-glycero-3-phosphocholine.

Examples of negatively-charged phospholipids that can be used to form the liposome of the present invention include but are not limited to phosphatidylglycerol (PG), phosphatidylserine (PS), phosphatidylinositol (PI), and phosphatidic acid (PA). An example of negatively-charged organic compounds that can be used to form the liposome of the present invention is dicetyl phosphate.

Any fluorescently-labeled phospholipids (preferably negatively-charged), include, but are not limited to, fluorescently-labeled PG, PS, PI and PA, can be used to form the liposome of the present invention. The exact position at which a phospholipid is labeled is not critical so long as fluorescence intensity changes upon hydrolization of the phospholipid components of the liposome by a phospholipase whose activity is being measured. The liposome of the present invention is preferably, but does not have to be, unilamellar.

In the method of the present invention, the activity of a phospholipase can be determined based on fluorescence data collected at a single time point or recorded on a continuous basis. The latter provides more reliable results because potential bias due to idiosyncrasies of particular time points can be avoided. The defined intervals can be zero second or a longer time period. For instance, a recordation of fluorescence intensity once every 10 sec (defined interval) over a period of two minutes is considered a continuous recordation for the purpose of the present invention.

In another aspect, the present invention provides a kit for measuring the activity of a phospholipase. The kit contains the fluorescently-labeled liposome of the present invention and the phospholipase.

In one embodiment, the method of present invention is used to measure the activity of a $PLA_2$. Examples of $PLA_2$ whose activity can be measured include but are not limited to $PLA_2$-IIA, pancreatic $PLA_2$ and bee venom $PLA_2$. In use, a liposome of the present invention is mixed with a $PLA_2$ reaction buffer to form a pre-reaction mixture. The $PLA_2$ reaction buffer can support the reaction catalyzed by the $PLA_2$. The fluorescence intensity of the pre-reaction mixture is recorded after which the $PLA_2$ is added into the pre-reaction mixture to form a reaction mixture. The fluorescence intensity of the reaction mixture is then measured and the $PLA_2$ activity can be determined by comparing the fluorescence intensity of the reaction mixture and the fluorescence intensity of the pre-reaction mixture.

When the method of the present invention is used to measure the activity of $PLA_2$ in a complex composition such as a biological sample, certain factors (e.g., proteins) in the composition may cause a relatively substantial increase in fluorescence intensity to mask any increase caused by the $PLA_2$ contained therein. This problem may be solved by including a $PLA_2$ stimulator such as α1-AT in the reaction. Since the $PLA_2$ stimulator can only further increase the increase of fluorescence intensity caused by $PLA_2$ but not other factors, the difference between the fluorescence increase in the presence and absence of the stimulator correlates with the $PLA_2$ activity.

It should be noted that the suitable temperature at which the $PLA_2$ activity in a biological sample is measured may be different from that for measuring the $PLA_2$ activity in a substantially pure source. The suitable temperature can be readily determined by a skilled artisan. An example of measuring the $PLA_2$ activity in the plasma of CF and COPD patients and in the synovial fluid of arthritis patients are described in the Examples. Since BALF, rather than a substantially pure source of $PLA_2$ stimulator α1-AT, was used in the studies presented in the examples below, the BALF was boiled at 100° C. for 5 min in advance to inactivate the components that may interfere with the assay.

In another aspect, the present invention relates to a method for measuring the activity of a $PLA_2$ or SFA. The method involves running the assay described above with $PLA_2$ in the presence and absence of a stimulator or inhibitor. The difference in $PLA_2$ activity as measured in the presence and absence of the stimulator or inhibitor reflects the activity of the stimulator or inhibitor.

In one embodiment, the $PLA_2$ stimulator ("$PLA_2$-s") or SFA activity of a biological sample is measured. As shown in the examples below, the volume of a biological sample can dictate whether a stimulator or SFA activity is measured. When both stimulator and SFA activities are present in the sample, the volume suitable for measuring the SFA activity is typically larger than that suitable for measuring the stimulator activity. In addition, the amount of exogenous $PLA_2$ used in the assay also affects the appropriate volumes for measuring the stimulator or SFA activity. Specific assay conditions with regard to sample volume can be readily determined by a skilled artisan.

As shown in the examples below, the $PLA_2$-s activity in the CF BALF only stimulated the activity of monomeric $PLA_2$-s (e.g., $PLA_2$-IIA, pancreatic $PLA_2$ and bee venom $PLA_2$) but not that of a dimeric $PLA_2$ (e.g., snake venom $PLA_2$). This is consistent with the fact that most $PLA_2$-s, especially those involved in inflammation conditions, are monomers. The $PLA_2$-s activity in the BALF is that of a truncated α1-AT. Thus, when the assay is used to measure the $PLA_2$-s activity of a biological sample that contains α1-AT, a monomeric $PLA_2$ should be used.

In another aspect, the present invention provides a method for identifying an agent that can alter the activity of a phospholipase. The method involves measuring the phospholipase activity in the presence of a test agent using the method described above. A control group is run in parallel except that the test agent is not included. The phospholipase activity of the test agent group is then compared to that of the control group. A higher than control activity indicates that the agent is a stimulator of the phospholipase and a lower than control activity indicates that the agent is an inhibitor of the phospholipase. This method can be readily adapted to detect the activity of a $PLA_2$ modulator by employing $PLA_2$ as the phospholipase and substituting a $PLA_2$ stimulator for the test agent.

In another aspect, the present invention provides a method for determining whether a human or non-human animal subject has an abnormally high $PLA_2$ activity. The method comprises measuring the $PLA_2$ activity in the presence of a biological sample prepared from the subject for measuring a SFA or activity or a $PLA_2$ stimulator activity. The $PLA_2$ activity is then compared to that of a control that is measured in the absence of the biological sample to determine the SFA or stimulator activity in the biological sample. Optionally, both the SFA and stimulator activities in the biological sample are determined. Lastly, the SFA activity, the $PLA_2$ stimulator activity, or the relative activity of the SFA to the stimulator or the stimulator to the SFA of the biological sample is compared to a normal range obtained from healthy subjects of the same species. A lower than normal range of SFA activity or SFA to stimulator relative activity, or a higher than normal range stimulator activity or stimulator to SFA relative activity indicates that the subject has an abnormally high $PLA_2$ activity.

A biological sample obtained from a human or non-human subject may contain certain factors that can make the detection of $PLA_2$ activity contained therein difficult. Therefore, in one embodiment of the method, the $PLA_2$ activity in a biological sample from the human or non-human subject is measured in the presence of a $PLA_2$ stimulator and the activity is then compared to a normal range established by using the same method and the same type of biological sample obtained from healthy subjects of the same species. A higher than normal range value indicates that the subject has an abnormally high $PLA_2$ activity.

Another solution to the problem is to use the $PLA_2$ stimulator and/or inhibitor activities in a biological sample as indicators of the $PLA_2$ activity therein. In healthy human and non-human animals, $PLA_2$ stimulators and inhibitors work together to keep $PLA_2$ activity in check and hence the production of lipid mediators in balance. Under pathological conditions, a decrease in SFA activity and/or an increase in $PLA_2$-s activity will lead to an increase in $PLA_2$ activity, which stimulates the production of lipid mediators. Therefore, $PLA_2$ stimulator and/or inhibitor activities can be used as indicators for the $PLA_2$ activity. Thus, in another embodiment of the method for determining whether a human or non-human animal subject has an abnormally high $PLA_2$ activity, the $PLA_2$-s activity, the SFA activity or the relative activity of $PLA_2$-s and SFA (e.g., the SFA/$PLA_2$-s activity ratio and the $PLA_2$-s/SFA activity ratio) in a sample obtained from the subject is determined using the method described above.

The activity is then compared to a normal range established by using samples obtained from healthy subjects of the same species. If the particular subject has a lower than normal SFA activity or SFA to $PLA_2$-s relative activity, or a higher than normal $PLA_2$-s activity or $PLA_2$-s to SFA relative activity, the subject is determined to have an abnormally high $PLA_2$ activity. As shown in the examples below, a higher relative activity of $PLA_2$-s to SFA can mean a lower absolute value of a negative SFA/$PLA_2$-s activity ratio, a higher absolute value of a negative $PLA_2$-s/SFA activity ratio, or a positive SFA/$PLA_2$-s or $PLA_2$-s/SFA activity ratio.

An abnormally high $PLA_2$ activity is associated with many disorders such as bacterial infection, viral infection, inflammation, CF, allergy, arthritis, sepsis, brain injury, cancer and cardiovascular disorders. The method of the present invention can help in identify individuals with such disorders and in implementing appropriate treatment and symptom relief strategies.

While a plasma or serum sample is suitable in the method of the present invention to determine whether a human or non-human subject has a high $PLA_2$ activity in general, analysis of a more specific biological sample may be required depending on the particular disorder in question. For example, for lung inflammation, an analysis of the $PLA_2$-s and SFA activities in BALF is preferred. As another example, for rheumatic arthritis, an analysis of the synovial fluid may be necessary. A skilled artisan can readily determine which samples are suitable for a particular disorder of interest.

In another aspect, the present invention provides another method for determining whether a human or non-human animal subject has an abnormally high $PLA_2$ activity. The method involves measuring the endogenous $PLA_2$ activity of a biological sample prepared from the subject in the presence of a $PLA_2$ stimulator and comparing the $PLA_2$ activity to a normal range obtained from healthy subjects of the same species. A higher than normal range $PLA_2$ activity indicates that the subject may have a disorder associated with an abnormally high $PLA_2$ activity.

In another aspect, the present invention provides another method for determining whether a human or non-human animal subject has an abnormally high $PLA_2$ activity. The method involves determining the amount of SFA, the amount of α1-AT or both from an appropriate biological sample prepared from the subject and comparing the amount of SFA, the amount of α1-AT, or the relative amount of SFA to α1-AT or α1-AT to SFA to a normal range obtained from healthy subjects of the same species wherein a lower than normal level or relative level of SFA, or a higher than normal level or relative level of α1-AT indicates the subject has an abnormally high $PLA_2$ activity In another aspect, the present invention provides a method for treating a disorder associated with an abnormally high level of $PLA_2$ activity in a human or nonhuman animal subject by inhibiting the $PLA_2$ stimulatory activity of α1-AT in the subject. The inventors have identified the full length α1-AT and the truncated α1-AT from 16His to 357Pro (amino acids 16 to 357 of SEQ ID NO:1) as $PLA_2$ stimulators. It is expected that any truncated form of α1-AT that retains at least the part of 16His to 357Pro has $PLA_2$ stimulatory activity. The inventors have further identified SFA as a $PLA_2$ inhibitor when present at a sufficiently high level. The exact amount of SFA needed to display the inhibitory activity may vary depending on conditions of a specific application but can be readily determined by a skilled artisan.

α1-AT is only an effective stimulator for monomeric $PLA_2$-s (e.g., $PLA_2$-IIA, pancreatic $PLA_2$ or bee venom $PLA_2$) but not dimeric $PLA_2$-s (e.g., snake venom $PLA_2$). Although the identification of the $PLA_2$ stimulators and inhibitor were made with human samples and proteins, it is expected that human α1-AT (including truncated forms) and SFA homologues in other species (e.g., other animal species) also have $PLA_2$ stimulatory and inhibitory activities. It is noted that α1-AT amino acid sequences in other species may differ from the human sequence. A skilled artisan can use an alignment program to identify the amino acids in those sequences that correspond to the 16His and 357Pro of the human sequence. In addition, one skilled in the art of molecular biology would appreciate that minor deletions, additions and mutations may not change the attributes of a $PLA_2$ stimulator and inhibitor. To determine whether or not a modified sequence will retain the essential stimulatory or inhibitory functions, one only need to produce the modified sequence and test it using one of the assays described in the present invention.

The $PLA_2$ stimulatory activity of α1-AT is resistant to heat inactivation while the $PLA_2$ stimulatory activity of albumin and the $PLA_2$ inhibitory activity of SFA are sensitive to heat inactivation. For example, boiling at 100° C. for 5 min can destroy the stimulatory and inhibitory activities of albumin and SFA. However, the stimulatory activity of α1-AT remained intact under the same conditions. Although determining the $PLA_2$ stimulatory activity of α1-AT in a biological sample such as plasma and serum is desirable under many circumstances, it proved to be difficult with the fluorescent method because the stimulatory activity of α1-AT is masked by that of the more abundant albumin (e.g., the albumin concentration (4.0 g/dL) and is 20 times higher than the α1-AT concentration (0.2 g/dL) in human plasma). Heat inactivation of such a sample can destroy the activities from albumin and allow the activity of α1-AT to be successfully measured. Heat inactivation has the additional benefit of destroying other factors in a sample that may potentially interfere with the detection of the stimulatory activity of α1-AT. Therefore, even for a biological sample such as BALF that may or may not contain a significant amount of albumin, heat inactivation is still preferred. Boiling at 100° C. for 5 min is a suitable heat inactivation condition. Other suitable conditions can be readily determined by a skilled artisan.

In another aspect, the present invention provides a method for diagnosing lung inflammation in CF patients by determining the presence of a truncated α1-AT in bronchial tubes, BALF or sputum. In CF patients, neutrophil elastase (NE) is believed to play a major role in the damage of airway cells and supporting tissues, which lead to bronchiectasis and bronchial obstruction. α1-AT is the most potent endogenous inhibitor of NE. In CF patients, the amount of α1-AT in the serum is typically about two-times higher than the normal level and the protein was fully active against NE (50). However, α1-AT is largely broken down and useless for inhibiting NE in bronchial tubes of the inflamed CF lung. Treating CF patients with α1-AT via aerosol inhalation has not clearly provided any benefit. The finding disclosed here that α1-AT can stimulate the activity of $PLA_2$ may provide an explanation as to why the treatment is not effective and suggests a different treatment strategy for these patients, i.e., to inhibit the $PLA_2$ stimulatory activity of truncated α1-AT.

There are many ways that the $PLA_2$ stimulatory activity of α1-AT or the $PLA_2$ inhibitory activity of SFA can be inhibited and a skilled artisan is familiar with these ways. For example, antibodies against α1-AT or SFA can be made and used to inhibit their activities. Other agents that can inhibit the $PLA_2$ stimulatory activity of α1-AT or the $PLA_2$ inhibitory activity of SFA can be identified by the method below.

For instance, in one aspect, the present invention provides a method for increasing the activity of a monomeric $PLA_2$ by exposing $PLA_2$ to a polypeptide that contains α1-AT in an amount sufficient to increase the activity of $PLA_2$. In an alternate aspect, the present invention relates to a method for inhibiting the activity of $PLA_2$ by exposing $PLA_2$ to a polypeptide that contains SFA in an amount sufficient to inhibit the activity of $PLA_2$. In yet another alternate aspect, the present invention relates to a method of inhibiting the activity of a monomeric $PLA_2$ stimulated by α1-AT by inhibiting the $PLA_2$ stimulating activity of α1-AT sufficient to lower the stimulated $PLA_2$ activity. In still yet another aspect, the present invention relates to a method of increasing the activity of $PLA_2$ inhibited by SFA by inhibiting the $PLA_2$ inhibitory activity of SFA to increase the inhibited $PLA_2$ activity.

In another aspect, the present invention provides another method for treating a disorder associated with an abnormally high level of $PLA_2$ activity in a human or nonhuman animal subject by increasing the $PLA_2$ inhibitory activity of SFA in the subject.

In another embodiment, the present invention relates to a method of treating a disorder associated with an abnormally high level of $PLA_2$ in a human or non-human animal subject by inhibiting the $PLA_2$ stimulatory activity of α1-AT or increasing the $PLA_2$ inhibitory activity of SFA. A skilled artisan is familiar with the ways that the stimulatory activity of α1-AT can be inhibited and the inhibitory activity of SFA can be increased. For example, antibodies and other α1-AT blocking agents can be administered to the subject. Strategies directed at suppressing the expression of α1-AT (e.g., the anti-sense technology) can also be used. To increase the inhibitory activity of SFA, a polypeptide containing SFA can be administered into the subject directly or an expression vector encoding the polypeptide can be introduced into the subject and the expression thereof can then be induced. Alternatively, SFA levels in the subject can be increased by strategies such as enhancing endogenous albumin expression and inhibiting albumin oxidization. Agents that can increase the inhibitory activity of SFA can also be used.

In another aspect, the present invention provides a method for identifying an agent that can alter the $PLA_2$ stimulatory activity of α1-AT or the $PLA_2$ inhibitory activity of SFA. The method involves exposing a composition containing $PLA_2$ and α1-AT or SFA to a test agent, measuring the $PLA_2$ activity of the composition in the presence of the test agent, and comparing the $PLA_2$ activity to that of a control composition that is not exposed to the test agent. If a difference is observed, the test agent should be further tested to eliminate the possibility that it altered the $PLA_2$ activity directly. In the method, α1-AT and SFA can be provided in a biological sample. However, one needs to heat inactivate the biological sample when used in identifying agents for altering the stimulatory activity of α1-AT if the sample contains substantial amounts of albumin. In addition, a monomeric $PLA_2$ should be used in the method for identifying agents that can alter the stimulatory activity of α1-AT since α1-AT only inhibits the activity of monomeric $PLA_2$-s.

One source of agents that can be screened is various chemical libraries including peptide libraries. Examples of such libraries include those from ASINEX (i.e. the Combined Wisdom Library of 24,000 manually synthesized organic molecules) and from CHEMBRIDGE CORPORATION (i.e. the DIVERSet™ library of 50,000 manually synthesized chemical compounds; the SCREEN-Set™ library of 24,000 manually synthesized chemical compounds; the CNS-Set™ library of 11,000 compounds; the Chemy-Pick™ library of up to 300,000 compounds) and linear library, multimeric library and cyclic library (Tecnogen (Italy)). Once an agent with desired activity is identified, a library of derivatives of that agent can be screened for better agents.

As shown in the examples below, α1-AT can inhibit the activity of PLC. In one aspect, the present invention relates to a method of inhibiting the activity of PLC by exposing PLC to a polypeptide that contains α1-AT in an amount sufficient to inhibit PLC activity.

In another aspect, the present invention relates to a method of stimulating PLC activity by inhibiting the PLC inhibitory activity of α1-AT sufficiently to stimulate the inhibited PLC activity. There are many ways that the PLC inhibiting activity of α1-AT can be inhibited and these ways have been described in connection with inhibiting the $PLA_2$ inhibitory activity of α1-AT.

In another aspect, the present invention relates to a method for identifying an agent that can alter the PLC inhibitory activity of α1-AT. The method involves exposing a composition containing PLC and α1-AT to a test agent, measuring the PLC activity of the composition in the presence of the test agent, and comparing the PLC activity to that of a control composition that is not exposed to the test agent. If a difference is observed, the test agent should be further tested to eliminate the possibility that the test agent altered the PLC activity directly. Examples of sources of agents that can be screened are described in connection with a similar method for $PLA_2$ inhibitory activity of α1-AT.

In another aspect, the present invention provides a method of measuring the activity of a lipase. The method involves contacting PLC with a liposome of the present invention in which the fluorescently labeled molecule contains a fluorescently labeled fatty acid moiety. Diacylglycerol will form by the action of PLC. The lipase is then brought into contact with diacylglycerol leading to the release of fluorescent-labeled fatty acids and hence an increase in fluorescence intensity. The increase in fluorescence intensity is monitored for determination of the lipase activity.

C. In another embodiment, the invention provides a new method of determining $sPLA_2$ activity in a subject using a fluorescent assay substrate that is specific for $sPLA_2$ and more sensitive and stable than the substrates previously used. The method comprises providing a substrate comprising a fluorescently-labeled phospholipid and a negatively-charged phospholipid in an organic solvent such as ethanol; mixing the substrate with phospholipase $A_2$ in a biological test sample from the subject; measuring a change in fluorescence intensity at defined intervals over a specific period of time to determine the $sPLA_2$ activity in the test sample; and comparing the $sPLA_2$ activity in the test sample to the $sPLA_2$ activity in a control sample, wherein an increase in fluorescence intensity as compared to the control sample indicates the subject has developed or is about to develop inflammation.

The substrate may further comprise phosphatidylcholine (PC), wherein the PC is dioleoyl PC (DOPC). Other organic solvents such as methanol or propanol may also be useful in the method of the present invention.

In a preferred embodiment, the subject is human, and the biological sample is selected from the group consisting of plasma, serum, bronchoalveolar lavage fluid, sputum, urine, synovial fluid, amniotic fluid, peritoneal fluid, white blood cells, alveolar macrophages, cerebrospinal fluid, pleural fluid, and pericardial fluid.

The negatively-charged phospholipid is preferably selected from phosphatidylglycerol (PG), phosphatidylcholine (PC), phosphatidylserine (PS), phosphatidylinositol (PI), phosphatidic acid (PA), a PG/PC mixture, and combinations thereof. A preferred example of the negatively-charged phospholipid is phosphatidylglycerol (PG), although a PG/PC mixture is also preferred.

The inventors observed that when a serum sample from a mammalian subject is added to the assay system, the fluorescence intensity (FI) increases. Accordingly, a subject having inflammation will have an increased fluorescent intensity as compared to a healthy control. Without intending to be limited by theory, the inventors believe that the method of the present invention accurately detects $sPLA_2$ activity in a sample because an increase in $sPLA_2$ causes an increase in fluorescence intensity when $sPLA_2$ induces a subset of albumin in the sample to release the fluorescently-labeled fatty acid.

In a preferred embodiment, the substrate comprises 1,2-bis-(4,4-difluoro-5,7-dimethyl-4-bora-3a,4a-diaza-s-indacene-3-undecanoyl)-sn-glycero-3-phosphocholine (BODIPY-PC) and dioleoyl PC in ethanol. However, one of ordinary skill in the art can readily determine which other combinations of phospholipids(s) and organic solvents to the extent not specifically disclosed herein, can be used as the substrate for practicing the present invention.

In the method of the present invention, the $sPLA_2$ activity in a sample can be determined based on fluorescence data collected at a single time point or recorded on a continuous basis. The latter provides more reliable results because potential bias due to idiosyncrasies of particular time points can be avoided. Continuous recording of the fluorescent intensity increases the accuracy of the measurement. For instance, the initial rate of the reaction may be much higher than at a later point in the reaction. Accordingly, continuous recordation more accurately reflects $sPLA_2$ activity.

In another aspect, the present invention relates to a method for assessing whether a mammalian subject such as a human subject has or is at risk of developing inflammation (e.g., systemic inflammation) or an inflammation-related disorder (e.g., COPD, CF, bacterial or viral infection, sepsis, and trauma such as head trauma) by determining whether a subject has a increasing or abnormally high $sPLA_2$ activity. In this regard, the $sPLA_2$ activity in a biological sample from the subject is measured according to the method of the present invention and then compared to (i) the $sPLA_2$ activity from the same subject measured at an earlier time; or (ii) a normal range of $sPLA_2$ activity obtained from healthy subjects of the same species.

For a particular type of biological sample, the normal $sPLA_2$ activity range can be determined by analyzing biological samples from a suitable number of healthy individuals. For example, at least 10, 20, 30, 50, or 100 healthy individuals are analyzed to determine the normal $sPLA_2$ activity range.

In one embodiment, the $sPLA_2$ activity of the subject is compared to a normal range of $sPLA_2$ activity obtained from healthy subjects of the same species. An increase in $sPLA_2$ activity as compared to a positive control indicates that the subject has inflammation (e.g., systemic inflammation when plasma or serum is the biological sample). For instance, a $sPLA_2$ activity 1%-70% higher, preferably 5%-60% or 10%-50% higher than normal would indicate the subject has moderate to severe inflammation.

In another embodiment, the above method is used for determining whether a human subject who is a tobacco smoker has developed or is about to develop chronic obstructive pulmonary disease (COPD) by monitoring the $sPLA_2$ activity of the subject. An increase decrease in $sPLA_2$ activity over time indicates that the subject has developed or is about to develop COPD. The amount of increase in $sPLA_2$ activity that is indicative of the onset of COPD varies, but will be understood by one of skill in the art. Smokers are at risk of developing COPD and monitoring $sPLA_2$ activity over time can provide early detection of COPD. In a typical example, a subject's $sPLA_2$ activity is measured at least once a month for at least one year. A continuous increase (regardless of the rate of increase) would indicate the development of COPD.

In another embodiment, the invention provides a method of measuring $sPLA_2$ activity of a human subject who undergoes a surgical procedure are measured before and after the surgery, wherein an increase in $sPLA_2$ activity after the surgery indicates that the subject has inflammation, such as that caused by an infection. In a typical example, a subject's $sPLA_2$ activity is measured at least every twelve hours. A continuous increase (regardless of the rate of increase) in $sPLA_2$ activity would indicate the development of sepsis or other inflammation disorder.

In another aspect, the present invention provides a kit for measuring $sPLA_2$ activity. The kit contains a fluorescently-labeled phospholipid as described above, a negatively-charged phospholipid as described above, an organic solvent such as ethanol, $sPLA_2$, and an instruction manual on how to measure $sPLA_2$ activity in a biological sample from a mammalian subject according to the method disclosed herein.

Optionally, the kit can contain a control sample. The control sample is a sample that has a known level of $sPLA_2$ activity. Examples of control samples include but are not limited to biological samples from a mammalian subject as described herein that has a known level of $sPLA_2$ activity. The subject can be a healthy subject or a subject with an abnormal condition described herein.

The instruction manual can be provided in the form of a publication, a recording, a diagram, or any other medium of expression which is suitable for communicating to a user how to measure $sPLA_2$ activity in a biological sample from a mammalian subject according to the method disclosed herein. The instruction manual of the kit can, for example, be affixed to a container containing the components of the kit or be shipped together with or separately from the container.

D. In another embodiment, the present invention provides a continuous $PLA_2$ fluorescent assay (33) to determine the effects of plasma or serum on $sPLA_2$ activity in real time, analyze the serum protein components that may affect the $sPLA_2$ activity, and determine the effects of $sPLA_2$ activity in a disease state.

Secretory phospholipase $A_2$ ($sPLA_2$) in circulation is an acute-phase inflammatory response protein. It may play a role as a bactericide in the case of sepsis and/or regulate the synthesis of bioactive lipid mediators in a wide range of inflammatory diseases. However, unregulated $sPLA_2$ activity in circulation may have detrimental effect on peripheral tissues. In the present invention, the inventors used a continuous $sPLA_2$ fluorescent assay to determine the factors in human plasma or serum that might have significant affect on $sPLA_2$ activity. Serum albumin was the predominant protein that either stimulated $sPLA_2$ activity in presence of small amounts of albumin, or inhibited $sPLA_2$ activity in presence of large amounts of albumin in the $sPLA_2$ assay mixture. Both stimulatory and inhibitory effects of albumin were triggered by $sPLA_2$ that promoted an albumin-liposome interaction.

Among the heterogeneous forms of albumin, a fatty-acid free specific fraction of albumin (SFA) that was about 5% of total albumin mass was mainly responsible for the albumin inhibitory effect on $sPLA_2$ activity. Using fluorescently-labeled fatty acid probes incorporated into liposomes as substrates, the $sPLA_2$-induced SFA activity in the serum from healthy individuals was $198.73 \pm 4.05$ (n=7) (fluorescence intensity or FI/min/μl serum), from subjects with chronic obstructive pulmonary disease was $93.03 \pm 14.12$ (n=3), and from patients with sepsis was $26.47 \pm 7.26$ (n=3). The results of this study suggest that in circulation $sPLA_2$ can induce albumin to interact with phospholipid membranes that can have a significant effect on $sPLA_2$ activity. Serum SFA activity could be used as a new indicator for assessing systemic inflammation.

III. Definitions

By "SFA" we mean the specific fraction of albumin (typically about five percent of the total albumin present in a biological sample) that stimulates or inhibits $PLA_2$. SFA (NCBI Accession No. CAA00606 or AAA98797) acts as a $PLA_2$ stimulator at low concentrations by relieving product inhibition. However, the inventors have shown that SFA also acts as a $PLA_2$ inhibitor under certain conditions. Without intending to be limited by theory, the inventors believe that SFA inhibits $PLA_2$ activity by blocking $PLA_2$'s action on cellular membranes.

By "biological sample" we mean a tissue or fluid sample from a mammalian subject, a sample from cultured cells or culture medium, or a preparation derived from any of the foregoing. In one embodiment, the biological sample is a fluid sample such as a blood, plasma, serum, white blood cells, alveolar macrophages, bronchoalveolar lavage fluid (BALF), synovial fluid, sputum, urine, amniotic fluid, peritoneal fluid, cerebrospinal fluid, pleural fluid, or pericardial fluid sample or a preparation derived therefrom. In a preferred embodiment, the sample is a plasma or serum sample or a preparation derived therefrom. While a blood, plasma, or serum sample is a suitable sample in general for various applications of the methods of the present invention, other biological samples may also be suitable depending on the particular disorder that the method of the present invention is applied to detect. One of ordinary skill in the art can readily determine which samples are suitable for a particular disorder of interest.

By "subject," we mean any member of the class Mammalia including, but not limited to, humans, non-human primates such as chimpanzees and other apes and monkey species, farm animals such as cattle, horses, sheep, goats, and swine, domestic animals such as rabbits, dogs, and cats, and laboratory animals such as rodents (e.g. rats, mice, and guinea pigs). The term "subject" does not denote a particular age or sex. Preferably, the subject is human.

By "$PLA_2$" we mean a phospholipase enzyme including secretory $PLA_2$ ($sPLA_2$) such as human $PLA_2$-IIA (e.g., recombinant human $PLA_2$-IIA, NCBI Accession No. NP_000291) or pancreatic $PLA_2$ (e.g., porcine pancreatic $PLA_2$-1B), as well as $PLA_2$ from bee venom and $PLA_2$ from snake venom.

By "negatively-charged phospholipid," we mean the class of lipid compounds containing a phosphate group, a glycerol moiety, and 1 to 2 fatty acid groups and having a net negative charge wherein one carbon of the glycerol moiety is joined by the phosphate group and one or both of the other two carbons of the glycerol moiety is joined by a fatty acid group. Examples of negatively charged phospholipids that can be used to form the liposome of the present invention include, but are not limited to, phosphatidylglycerol (PG), phosphatidylcholine (PC), phosphatidylserine (PS), phosphatidylinositol (PI), phosphatidic acid (PA) apc/PG mix or any combination thereof. In one embodiment, PG is used to form the liposome used in the present invention. In another embodiment, the liposome contains two phospholipids such as PG and PC. Examples of PCs that can be used include, but are not limited to, DOPC, dipalmitoyl PC and PCs with other fatty acyl groups. DOPC is a preferred PC for the purpose of the present invention.

By "carboxylic acid," we mean a compound defined by the formula R—COOH wherein R is a hydrocarbon chain having a length of about 4 to 24 carbons, preferably 6 to 18 or 6 to 14 carbons, and more preferably 6 to 13 carbons. The hydrocarbon chain can be saturated, unsaturated, linear, branched, cyclic, or polycyclic and can have substituted groups including those with heteroatoms (atoms other than carbon and hydrogen). Examples of heteroatoms include but are not limited to N, S, O and Cl. In one embodiment, the hydrocarbon chain either does not have heteroatoms or only has one or more oxygen heteroatoms. In another embodiment, R is an alkyl, alkenyl, or alkynyl group. In a preferred embodiment, R is an alkyl or alkenyl group. Examples of carboxylic acids that can be used in the present invention include, but are not limited to, hexanoic acid, heptanoic acid, octanoic acid, nonanoic acid, decanoic acid, methyldecanoic acid, dodecanoic acid, tridecanoic acid, and tetradecanoic acid. The exact position at which a carboxylic acid is labeled is not critical so long as fluorescence intensity changes upon removal from the liposome by SFA.

By "continuous recordation" or "continuous measurement" we mean measuring the fluorescent intensity of the substrate- or liposome-sample mixture at a defined interval or intervals over a specific time period. The defined intervals can be zero seconds or a longer time period. For instance, recording fluorescent intensity once every ten seconds (defined interval) over a period of two minutes is considered a "continuous recordation" for the purpose of the present invention.

By "$PLA_2$ modulator" we mean $PLA_2$ stimulators and $PLA_2$ inhibitors.

By "α1-AT" we mean the full length α1-AT, a truncated form of α1-AT or both. A truncated form of α1-AT is an α1-AT that is shorter than the full length α1-AT but at minimum contains the amino acid sequence of 16His to 357Pro of SEQ ID NO:1 or its equivalent in other α1-AT sequences.

By "substantially pure" we mean preparations of $PLA_2$ or $PLA_2$ stimulators or inhibitors that are purified to a degree so that any impurities contained therein do not interfere with any of the assays of the present invention to an unacceptable level.

By "buffer systems" we mean those buffers known to a skilled artisan that can support the reactions catalyzed by a phospholipase such as a $PLA_2$. Examples of buffer systems that can be used include but are not limited to Tris-HCl, phosphate, acetate, citrate and glycine. The pH value of a buffer system can range from about 2 to about 10, preferably from about 6 to about 10, and most preferably about 7.4. In the case of the Tris-HCl system, the Tris-HCl concentration can range from about 0.001 M to about 1.0 M, preferably from about 0.005 M to about 0.2 M, and most preferably about 0.01 M. When the activity of a calcium-dependent $PLA_2$ is measured, a calcium source is also added into the buffer system. Examples of calcium sources that are useful in the present invention include but are not limited to $CaCl_2$, calcium fluoride and calcium carbonate. The $Ca^{2+}$ concentration in the buffer system can be from 0 to about 1.0 M, preferably from about 0.0001 M to about 0.1 M, and most preferably about 0.01 M. It is noted that other metals such as magnesium can replace calcium for the purpose of measuring the $PLA_2$ activity.

By "control sample", we mean a biological sample from (i) the same subject measured at any earlier time; or (ii) a normal range of SFA activity obtained from a healthy subject of the same species.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on an internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

IV. EXAMPLES

Example 1

Measuring SFA

Preparing $PLA_2$. Porcine pancreatic $sPLA_2$ (EC3.1.1.4) was purchased from Sigma Chemical (St. Louis, Mo.). The working solution of $sPLA_2$ was freshly prepared by diluting about 10 units of $PLA_2$ to 1 ml with 0.01 M Tris-HCl, pH 7.4 and kept at 4° C. prior to use.

SFA activity assay. Unless otherwise specified, the assay described in this example was used to conduct the experiments presented in this example. Liposome substrates were prepared by mixing C1-BODIPY C12 FA with 50% DOPC and 50% PG in a ratio of 0.016 mg: 1 mg: 1 mg (for 1 ml liposomes) in chloroform (C1-BODIPY C12 FA: 4,4-difluoro-5-methyl-4-bora-3a,4a-diaza-s-indacene-3-dodecanoic acid; DOPC: dioleoyl phosphotidylcholine; and PG: phosphatidylglycerol). After chloroform was evaporated to dryness under a stream of nitrogen, lipids were suspended in 1.5 ml sucrose/Tris buffer (0.25 M sucrose, 50 mM Tris-HCl, 0.02% sodium azide), pH 7.4. The suspension was stirred occasionally with vortex within 30 min. Then, the lipid suspension was sonicated 6 times (30 s at a time with 1-minute intervals between sonications) on ice using a Virsonic cell disrupter (VirSonic, Gardiner, N.Y.). The liposomes were stored at 4° C. before use.

In single cuvette assay, the 3 ml reaction mixture contained 0.01 M Tris-HCl, 10 mM calcium, 60 μg liposomes labeled with C1-BODIPY C12 FA (described above), $PLA_2$ (10-20 ng) and/or serum (1-10 μl) sample. The assay was conducted at room temperature for 2-4 minutes and FI was recorded every 5-10 seconds using a Perkin-Elmer Luminescence Spectrometer LS50B equipped with FL WinLab™ software (Perkin-Elmer Instruments, Norwalk, Conn.) at 488 nm excitation (slit 2.5) and 530 nm emission (slit 5.0).

In microplate assay, the volume of the reaction mixture and the amounts of reagents were reduced to one tenth of that used in single cuvette assay or otherwise as specified. The assay was also conducted at room temperature for 2-4 minutes; FI was recorded every five seconds. 96-well microplates were used for the microplate assay.

Microplate SFA activity assay using DOPC-PG/BODIPY-FA substrate prepared in ethanol. Substrate was prepared by mixing 1 mg DOPC, 1 mg PG, and 0.016 mg C1-BODIPY C12 FA in 0.5 ml ethanol. An aliquot of buffer (10 mM Tris-HCl, 10 mM $Ca^{2+}$, pH 7.4) was added into a well. The volume of the buffer was adjusted to have a final volume of 0.3 ml after subtraction of the volumes of the components to be added into the reaction mixture. Then, an amount of 6 μg substrate phospholipids in ethanol (1.5 μl) was added into the buffer, followed by addition of 1 μl of serum in the presence or absence of 1 μl (5 ng) of $sPLA_2$ solution. The solution in the well was rapidly mixed after addition of each component. Fluorescence intensity (FI) was recorded every 5 seconds at room temperature for 3 min. The activity was determined from the initial rate of the reaction curve from the data of the first 2 min of reaction and expressed as change in FI/min/microL serum.

Endotoxin effect (lipopolysaccharide) (LPS) on SFA activity in rat serum. Sprague Dawley rats were obtained from Charles River Laboratories and kept in the animal house facility at the University Clinical Science Center. All rats were fed with normal diet for a week and appeared to be healthy. Before a rat was injected with lipopolysaccharide (LPS or endotoxin) (*E. coli* 055:B5) (Sigma-Aldrich), the rat was anesthetized and blood was sampled. Then, the rat was injected intra peritoneal with LPS (3 mg/kg body weight). Three hours later after LPS injection, blood was taken again. Serum was isolated from each blood sample and stored at −70° C. before use.

SFA activity in the rat serum was determined using the BODIPY-FA liposome-microplate method described above. The assay in a microplate well contained 6 μg liposome phospholipids in buffer, 10 mM $Ca^{2+}$, and 1 μl serum in a final volume of 0.3 ml of 10 mM Tris-HCl, pH 7.4. The assay was conducted in the absence and presence of 5 ng porcine pancreatic $sPLA_2$ (Sigma-Aldrich) in the reaction mixture at room temperature for 2-4 minutes. FI was recorded every 5 seconds. The activity was determined from the initial rate of the reaction curve (see FIG. 2) and expressed as change in FI/min/microL serum.

Figure 1:
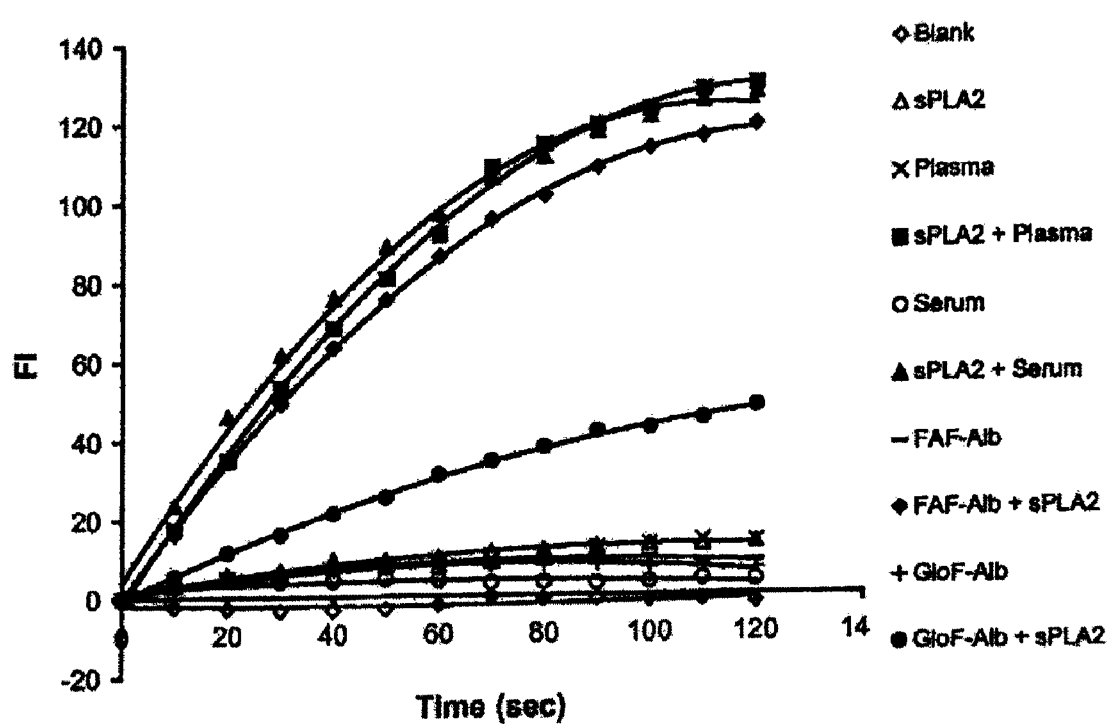
FIG. 1 is an example of single cuvette assay for determining exogenous $sPLA_2$-induced serum or plasma SFA activity. The single cuvette assay contained 3 ml of 0.01 M Tris-HCl, pH 7.4, 10 mM $Ca^{2+}$, and 60 μg liposomes (DOPC-PG liposomes labeled with fluorescent BODIPY-FA), in the presence or absence of proteins as specified. Serum (plasma) (10 μl) or pancreatic $sPLA_2$ (10 ng) alone in the reaction mixture did not generate significant fluorescence intensity (FI) change as compared to the blank (BODIPY-FA liposomes and calcium). However, when serum (or plasma) and $sPLA_2$ were present in the reaction mixture, FI increased in a time-dependent manner. Similarly, the presence of albumin (Alb) and $sPLA_2$ in the reaction mixture also produced substantial FI increase. Fatty acid-free (FAF) albumin had much higher activity than globulin-free (GloF)-albumin. DOPC: dioleoyl phosphotidylcholine; PG: phosphatidylglycerol; BODIPY-FA: 4,4-difluoro-5-methyl-4-bora-3a,4a-diaza-s-indacene-3-dodecanoic acid. In the following figures, $sPLA_2$ refers to pancreatic $PLA_2$ ($PLA_2$-1B) or is otherwise specified.

Single cuvette SFA activity assay. The plot of FI against reaction time was normalized by subtracting the initial FI reading from subsequent readings. The presence of $sPLA_2$ (porcine pancreas, Sigma P6534) in the reaction mixture did not significantly change the FI, i.e., $sPLA_2$ activity was not detectable in this reaction (FIG. 1). The presence of serum or plasma in the reaction mixture also did not yield any significant change in FI. However, in the presence of serum (or plasma) and $sPLA_2$, FI increased in a time-dependent manner. The SFA activities of serum and plasma were the same. Similarly, the presence of human serum fatty acid-free albumin (FAF-Alb) and $sPLA_2$ caused FI increase, but the SFA activity of globulin-free albumin (GloF-Alb) was much lower than that of FA-free albumin (FIG. 1).

Microplate SFA activity assay shows that exogenous $sPLA_2$ induced SFA activity in human serum. SFA activity in serum was also determined in 96-well microplates. The assay in each microplate well was determined individually because of the rapid SFA reaction that should be recorded within 2-4 minutes and the current PerkinElmer LS50B plate reader is not capable of recording multiple samples at that short time.

Figure 2:
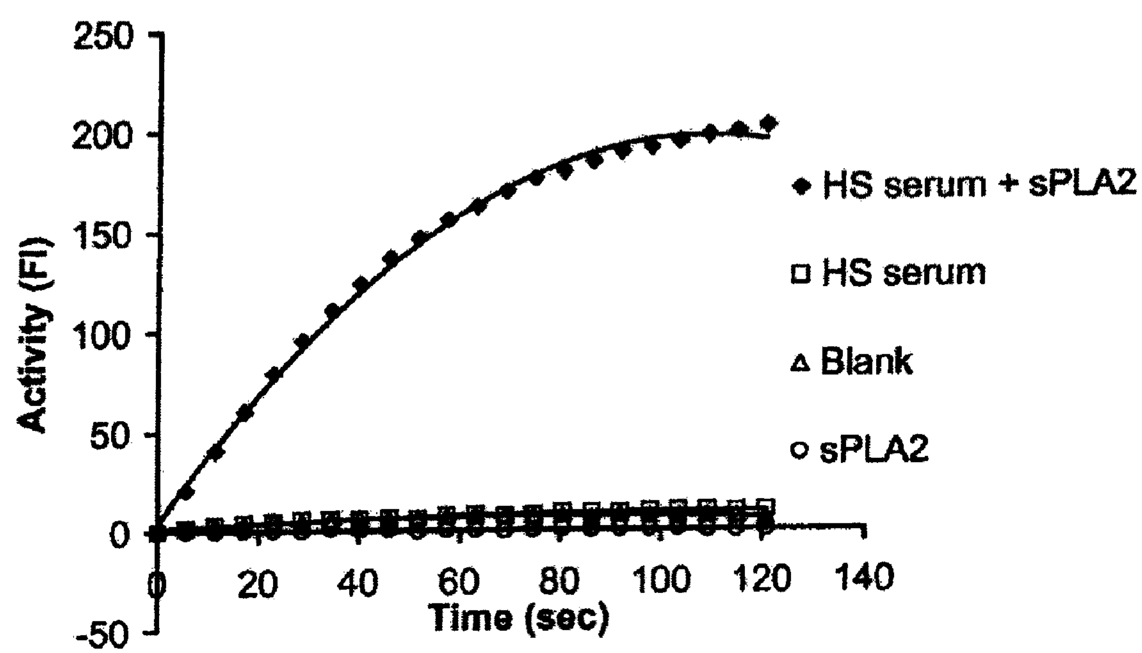
FIG. 2 is an example of microplate assay for determining exogenous $sPLA_2$-induced serum SFA activity. The reaction mixture contained the same components as described above in the single cuvette assay, except all components and reaction volume were reduced 10-fold or as otherwise specified. Reactions containing HS (healthy subject, normal volunteer) serum (1 μl) or $sPLA_2$ (5 ng) alone had similar FI as the blank (BODIPY-FA liposomes and calcium). Reaction containing both exogenous $sPLA_2$ (5 ng) and serum (1 μl) yielded a time-dependent increase in FI.

In the microplate assay, an amount of 1 ng of exogenous porcine pancreatic $sPLA_2$ was added to the reaction mixture in a microplate well followed by addition of 1 μl of serum, mixing well after each addition. An example of serum SFA activity is shown in FIG. 2. The reaction curve was fitted to a second-order polynomial equation and the first-degree coefficient was taken to be the initial rate of reaction ($V_0$) and expressed as change in F/min. The baseline FI change was determined for the reaction in the absence of the sample or protein.

The SFA activity was determined in sera from healthy subjects (HS), cigarette-smoking but otherwise healthy individuals (CS), patients with chronic obstructive pulmonary disease (COPD), and patients with acute respiratory decompensation requiring intensive care admission for treatment of pneumonia or sepsis at a life trauma support center (TLC). Obtaining serum samples from human subjects was approved by the Institutional Review Board of the University of Wisconsin School of Medicine and Public Health. Informed consent was obtained from all subjects or their authorized representatives for the collection of the samples.

Striking differences in serum SFA activity among the assayed groups (HS, CS, COPD, and SEPSIS) are observed (FIG. 3). The activities (FI/min) of SFA of sera from HS were 2-times higher than that from COPD and SEPSIS. Although three out of four CS serum samples had similar SFA activity as HS, one CS had lower SFA than normal.

Microplate SFA assay shows that endogenous $sPLA_2$ induced SFA activity in human serum. In these assays, no exogenous $sPLA_2$ was added to the reaction mixture. In the absence of exogenous $sPLA_2$, sera from HS, CS, and COPD did not have significant SFA activity (FIG. 4). However, sera from septic patients had significant increase in SFA activity (FIG. 4). This is believed to be due to the presence of endogenous $sPLA_2$ in the serum from septic patients (33).

Use of SFA Activity as a Biomarker. Subtracting endogenous $sPLA_2$-induced SFA activity from exogenous $sPLA_2$-induced SFA activity ([serum+exogenous $sPLA_2$] assay)

yields an even more striking pattern of the SFA activity among HS, CS, COPD, and SEPSIS individuals (FIG. 5). The average activity units (FI/min) of SFA in the sera from HS, CS, COPD, and SEPSIS are 198.7±4.1 (n=7), 190.6±9.5 (n=4), 93.0±14.1 (n=3), and 26.5±7.3 (n=3), respectively (number in parenthesis represents number of subjects; each sample was assayed in triplicate).

Determining SFA activity using liposomes with different phospholipid compositions. SFA activity could not be determined using the substrate composed of 100% PC containing BODIPY-FA (FIG. 6). The SFA activity was observed using 100% PG substrate, but the highest SFA activity was obtained using 50% PC and 50% PG substrate (FIG. 6).

Use of DOPC-PG and BODIPY-FA in ethanol as substrate. An example of the time course-activity graph generated from the assay using the substrate of BODIPY-FA labeled 50% DOPC-50% PG in ethanol solution is shown in FIG. 7. Two different isoforms of $sPLA_2$, $PLA_2$-1B (porcine pancreatic protein) and $PLA_2$-IIA (recombinant human protein) were tested in this assay. The results show that there is no significant increase in FI in the reaction solution containing either $sPLA_2$ ($PLA_2$-1B or $PLA_2$-IIA) or serum during the period of assay, as compared to the background. However, FI rapidly increased with time in the reaction mixture containing both $sPLA_2$ ($PLA_2$-1B or $PLA_2$-IIA) and serum (FIG. 7A). These results are similar to that observed with using liposome substrate prepared in buffer as shown in FIG. 2.

This study shows that the assay can use the phospholipid substrate either prepared as liposomes in buffer or dissolved in ethanol; $PLA_2$-1B and $PLA_2$-IIA yielded similar results. In this study the inventors also observed that the SFA activity could not be detected when BODIPY-FA alone was dissolved in ethanol, indicating that the detection of the SFA activity requires a substrate of mixture of fatty acid with negatively charged phospholipids (FIG. 7A).

In addition, substrates of PC-PG containing BODIPY-PC (2-(4,4-difluoro-5,7-dimethyl-4-bora-3a,4a-diaza-5-indacene-3-pentanoyl)-1-hexadecanoyl-sn-glycero-3-phosphocholine) can also be prepared in ethanol and used in the sPLA2 assay of the present invention. A comparison of the activity of sPLA2-IIA in human serum using 100% PG-BODIPY-PC liposomes in ethanol and 100% PG-BODIPY-PC liposomes in buffer as substrates is shown in FIG. 7B. Using phospholipid substrates in ethanol offers many unexpected advantages, such as, for example, the substrates are easy to prepare, they are stable at −20° C., and they represent better yield higher activity substrates for PLA2 (FIG. 7B).

Figure 8B:
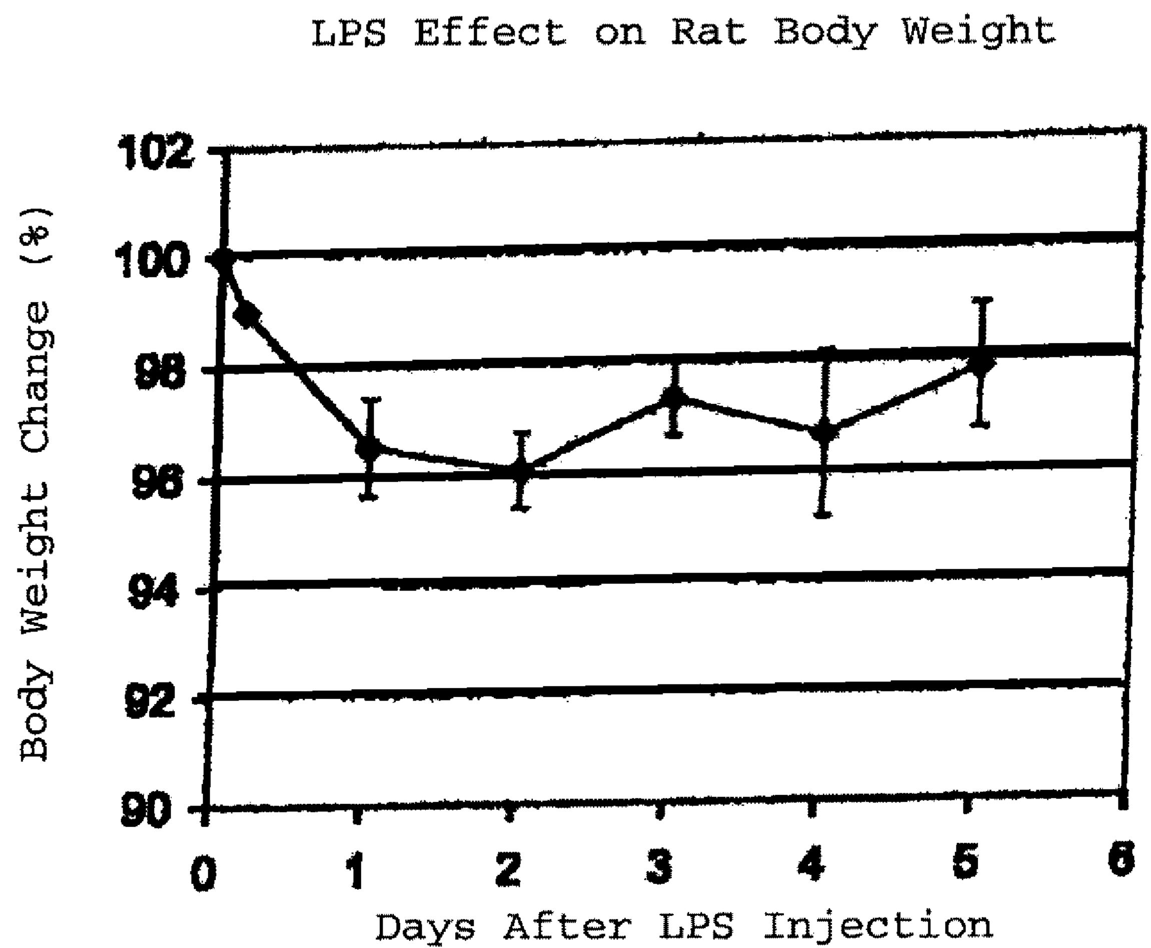

The inventors have also determined the sPLA2 and SFA activities in the serum from LPS-sPLA2 rat model using 100% PG-BODIPY-PC ethanol substrate and 50% DOPC-50% PG-BODIPY-FA ethanol substrate, respectively. Specifically, the inventors have recently developed an endotoxin (lipopolysaccharide) (LPS)-induced inflammation rat model to determine $sPLA_2$ activity in serum using 100% PG-BODIPY-PC in ethanol as substrate. An amount of 100 μl of blood was collected from pedal vein before (Day 0), 4 hours, 1, 2, 3, 4, and 5 days from the same rat following LPS injection (3 mg/kg body weight). Serum $sPLA_2$ activity increased and peaked on day 1 and started to decrease on day 2, and further decreased to the baseline level on days 4 and 5 following LPS injection (FIG. 8A). The $sPLA_2$ activity time course profile correlated well with some of the observations of the rats, such as body weight loss and lack of mobility. The rats had significant body weight loss 4 hours after LPS injection, further body weight loss on days 1-2, and started to show body weight gain from days 3-5 (FIG. 8B). Also, from 4 hours to 1-2 days following LPS injection, rats showed lack of body mobility, but started to be more active on day 3 and appeared to be healthy on days 4 and 5. The results suggest that serum $sPLA_2$ activity is closely correlated with pathogenesis of LPS-induced inflammation.

The activity time course profiles of serum $sPLA_2$ and SFA correlate well with the recovery of the rats following LPS injection, as shown in FIG. 9. SFA activity peaked on day 2, the day the rats started to show recovery from LPS-induced illness. These results suggest that both serum $sPLA_2$ activity and SFA activity can be used as specific markers for assessing acute-phase response of inflammation and recovery.

Specifically, these results show that a substrate of 100% PG-BODIPY-PC prepared in ethanol is better than that prepared in buffer as liposomes for $sPLA_2$ assay. The results also show that a substrate of 50% DOPC-50% PG-BODIPY-FA prepared in ethanol is better than that prepared in buffer as liposomes for SFA assay. Finally, the results indicate that serum $sPLA_2$ activity and SFA activity correlate well with pathogenesis of infection and can be used as inflammation specific markers.

Most studies of the context of infections rely heavily on the determination of circulating levels of cytokines as indicators of ongoing inflammation. Serum cytokines are primarily involved in the initial phase of inflammation and thus spike within 1-2 hours following the induction of inflammation. Cytokine levels often return to baseline levels within a few hours (34-37). Therefore, the determination of cytokines levels may not provide an accurate, consistent and complete evaluation of inflammation, but rather provide a small glimpse into the inflammatory response, which often lasts several days or weeks with significant pathology occurring over this extended period. Although C-reactive protein (CRP), an acute-phase response protein, has been shown to increase in the serum in response to infections (38, 39), it is considered to be a non-specific marker of inflammation (40). The results suggest that sPLA2 and SFA are specific markers for inflammation.

The effect of LPS on SFA activity in rat serum. As observed in normal human serum, healthy rat serum did not stimulate FI in the BODIPY-FA liposome assay in the absence of exogenous $sPLA_2$ (FIG. 10). However, serum from the rats which received LPS markedly increased FI in the absence of exogenous $sPLA_2$. In the presence of exogenous $sPLA_2$, serum collected before and after LPS injection showed a striking increase in FI (FIG. 10). There was no significant difference in the exogenous $sPLA_2$-induced FI increase in the serum collected before and after LPS injection. Subtraction of the FI of (Serum−Exogenous $PLA_2$) from the FI of (Serum+Exogenous $sPLA_2$) shows a nearly 80% decrease in the SFA activity in the serum from the rats administered LPS ($p=1\times10^{-6}$, duplicate assay from 5 rats) (FIG. 11). These results are similar to those observed in human serum comparing normal, healthy subjects (HS) with those with sepsis (see FIG. 5). The results show that the BODIPY-FA liposome assay is a highly sensitive and rapid method to determine systemic inflammation in response to infection (e.g., sepsis). Similar results as those shown in FIGS. 10 and 11 were observed using the substrate of BODIPY-FA-labeled 50% DOPC-50% PG in ethanol (data not shown).

Example 2

Measuring Phospholipase Activity

Bronchoalveolar lavage fluid. Samples of bronchoalveolar lavage fluid (BALF) were obtained from normal volunteers and patients with CF as described previously (41). The fluid was filtered through two layers of a sterile gauze into a 50 ml tube, then centrifuged at 1,200 rpm for 10 min at 4° C. using a Beckman Model TJ-6 centrifuge. The cell-free BALF was stored at −70° C. before use. The cell pellets were washed with about 35 ml incomplete Hanks balanced salt solution (HBSS) and spun at 1,000 rpm at 4° C. for 10 min. The pellets were suspended in 1-2 ml HBSS. Total and viable cells were counted by mixing an aliquot of cell suspension and trypan blue solution using a hemacytometer. An amount of 15,000 to 20,000 cells was taken for each cytospin slide preparation for morphological analyses using Diff-Quik Stain Set (Dade Behring AG, Dudingen, Switzerland). The rest of the cell suspension was spun at 1,000 rpm and the supernatant was discarded. The pellets were suspended in HBSS buffer; approximately $5\times10^6$ cells were homogenized in 100 μl buffer containing 2 mM phenylmethylsulfonyl fluoride (PMSF) and 1 mM EDTA and sonicated for 30 sec two times on ice using a Virsonic cell disrupter. The cell homogenate was centrifuged at 10,000 rpm for 1 min; the supernatant was saved and stored at −70° C. before use and the pellet was discarded.

A portion of the cell free BALF was concentrated 50-fold to less than 0.2 ml using an Amicon microconcentrator-10 (membrane cut-off molecular weight 10,000) as described previously (41). The condensed BALF was stored at −70° C. before use. The protein content in each sample was determined by the method of Lowry modified for 96-well plate analysis.

Sputum. Sputum is induced by inhalation of a 3% saline mist generated from an ultrasonic nebulizer. Wearing noseclips, subjects inhale the saline mist with tidal breaths and with an inspiration of total lung capacity once every minute. Every 4 min subjects are instructed to blow their noses and rinse their mouth with water before expectoration to minimize nasal contamination of the sample. This procedure continues for 12-24 min until an adequate volume of sputum is produced. Sputum is stored in a sterile container on ice and processed immediately (within 1 hour).

Sputum is transferred to a 50 ml conical polypropylene tube and its weight is determined. The sputum sample is mixed with 10% Sputolysin (Calbiochem, Biosciences, Inc., Lo Jolla, Calif.) and the mixture is incubated at 37° C. in a shaking incubator for 15 min. The solution is centrifuged at 2,000 rpm at 20° C. for 5 min. The supernatant and cells in the pellet are separated for further analysis.

Isolating neutrophils, mononuclear leukocytes and plasma from peripheral blood. Blood was collected into a heparinized tube from a normal healthy subject or from subjects with CF or COPD. Neutrophils, mononuclear leukocytes and plasma were isolated using the neutrophil isolation media (NIM, Cardinal Associates, Santa Fe, N. Mex.) as described by the manufacturer's protocol. Cell differentiation and purity were analyzed by cytospin and morphological analysis using Diff-Quik Stain Set (Dade Behring AG, Dudingen, Switzerland). Cells were suspended in HBSS buffer containing 2 mM PMSF and 1 mM EDTA and sonicated for 30 sec two times on ice using a Virsonic cell disrupter. Approximately $5\times10^6$ cells were homogenized in 100 μl buffer. The cell homogenate was centrifuged at 10,000 rpm for 1 min; the supernatant was saved and stored at −70° C. before use and the pellet was discarded. The plasma was stored at −20° C. before use.

Preparing PLA2 and fluorescently-labeled liposomes. Porcine pancreatic $PLA_2$ (EC3.1.1.4), $PLA_2$ from bee venom (*Apis mellifera*) and $PLA_2$ from snake venom (*Crotalus durissus terrificus*) were purchased from Sigma Chemical (St. Louis, Mo.). The working solution of $PLA_2$ was freshly prepared by diluting about 10 units of $PLA_2$ to 1 ml with 0.01 M Tris-HCl, pH 7.4 and kept at 4° C. prior to use. Dioleoyl phosphatidylcholine (DOPC) and phosphatidylglycerol (PG) were purchased from Sigma Chemical. Fluorescently-labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) was obtained from Molecular Probes (Eugene, Oreg.).

Fluorescently-labeled unilamellar liposomes (UL) were used as substrates for in vitro measuring of $PLA_2$ activity, similar to that described previously for rapid screening of a $Ca^{2+}$-independent $PLA_2$ isolated from rat lung (13). Fluorescent liposomes were prepared as previously described (42) by mixing 2.04 μmol DOPC, 2.04 μmol PG, and 0.018 μmol Bis-BODIPY FL $C_{11}$-PC in a molar ratio 10:10:0.14 in chloroform. After chloroform was evaporated to dryness under a stream of nitrogen, lipids were suspended in 1.5 ml sucrose/Tris buffer (0.25 M sucrose, 50 mM Tris-HCl, 0.02% sodium azide), pH 7.4. The suspension was stirred occasionally with vortex within 30 min. Then, the lipid suspension was sonicated 3 min on ice using a Virsonic cell disrupter (VirSonic, Gardiner, N.Y.). The liposomes were stored at 4° C. before use. Radioactively labeled liposomes were made of 2.04 μmol DOPC and 2.04 μmol PG in the presence of 1 μCi of L-α-[1-$^{14}$C]dioleoyl PC (NEN Du Pont, Wilmington, Del.) in 1.5 ml sucrose/Tris buffer as described (43).

Fluorescent assay of $PLA_2$. The $PLA_2$ assay was conducted in a cuvette in which 2.95 ml 0.01M Tris-HCl, pH 7.4, 30 μl of 1 M $CaCl_2$, and 10 μl of liposomes (27.3 nmol phospholipids) were each added. The solution was mixed well after the addition of each component. The fluorescence intensity of the solution was measured at room temperature using a Perkin-Elmer Luminescence Spectrometer LS50B equipped with FL WinLab software (Perkin-Elmer Instruments, Norwalk, Conn.) at 488 nm excitation (slit 2.5) and 530 nm emission (slit 5.0) to obtain the background reading. Then, an aliquot of $PLA_2$ (0.01-0.5 μg) working solution was added to the reaction mixture followed by rapid inversion of the cuvette three times (the final volume of the reaction mixture was 3 ml). Fluorescence intensity readings were immediately recorded every 10 sec for 2 min. In some tests, the fluorescence intensity of the reaction solution without the presence of $PLA_2$ was recorded for up to 2 min. To test $PLA_2$ activity in biological samples, an aliquot of sample solution was introduced to the reaction mixture prior to the addition of $PLA_2$ and the fluorescence intensity was determined for up to 2 min. Then, $PLA_2$ was added and fluorescence intensity was recorded as described above. Porcine pancreatic $PLA_2$ was routinely used in this and following studies unless otherwise specified.

Radioactive assay of $PLA_2$. In a 5 ml glass test tube, the $PLA_2$ reaction mixture contained 0.1 ml of 0.01 M Tris-HCl buffer (pH 7.4), 10 mM $CaCl_2$, 5 nmol $^{14}$C-labeled liposomes and 0.5 μg of pancreatic $PLA_2$. In some tests, 25-100 μg of CF BALF proteins, or 10 μg of rabbit lung annexin I or annexin VIII or both were added to the reaction mixture as specified. The reaction was carried out at room temperature for 30 sec and stopped by adding 2 ml of chloroform:methanol (1:2 vol) followed by addition of 0.4 ml water, and 10 μl of egg PC and lysoPC (20 nmol) which was used as carrier. The test tube was stirred using a Vortex. Lipids were extracted by adding additional 0.6 ml water and 0.6 ml chloroform. After agitating on a vortex, the mixture was centrifuged at 2,000 rpm for 10 min. The chloroform layer was withdrawn and transferred to a new test tube using a Pasteur pipette. Chloroform was evaporated to dryness under a flow of nitrogen. PC and lysoPC were isolated by the methods of silica gel thin-layer chromatography (TLC) using a developing solvent system of chloroform/methanol/water in a ratio of 65/45/5 as described previously (41). Lipids on the TLC plate were visualized by exposure of the TLC plate in an iodine tank. The PC, lysoPC and FA spots on the plate were scraped into a scintillation vial and a cocktail of scintillation fluid was added to the vial. Radioactivity in the vial was determined by using a beta scintillation counter. $PLA_2$ activity was expressed as either decrease in PC radioactivity or increase in fatty acid or lysoPC radioactivity as described previously (41).

Heat treatment of BALF and plasma. A portion of BALF or plasma was incubated in boiling water for 5 min followed by centrifugation at 10,000 rpm for 5 min. The supernatant was removed from the pellet. The pellet was suspended in the same volume of the supernatant and sonicated for 30 sec on ice. The protein content in both supernatant and pellet fractions were determined as described above. An aliquot of the supernatant or pellet was added to the $PLA_2$ reaction mixture as specified.

Presence of $PLA_2$-s and SFA activities in human plasma. In the fluorescent assay an initial reading was recorded at zero time and then readings were recorded every 10 sec for 2 min. To present $PLA_2$ activity, the initial reading was subtracted from the subsequent readings and $PLA_2$ activity was expressed as fluorescence intensity vs. time (sec). The fluorescence intensity of the reaction mixture containing buffer, $CaCl_2$ and fluorescently-labeled liposomes remained relatively unchanged for up to 2 min (FIG. 12). Introduction of 0.1 μg of porcine pancreatic $PLA_2$ into the reaction mixture caused a linear increase in fluorescence intensity for up to 2 min. The presence of plasma collected from a normal, healthy subject (N1) (plasma 061301) increased the $PLA_2$ activity in a dose-dependent manner up to 4-6 μl of plasma (FIG. 12). Above 4-6 μl, the plasma exhibited an inhibitory property against $PLA_2$ activity and the $PLA_2$-stimulating activity, also in a dose dependent manner (FIG. 12). The plasma at 15 μl not only completely inhibited $PLA_2$ activity and the $PLA_2$-stimulating activity, it also reduced the fluorescence intensity of liposomes below the baseline values (FIG. 12). At 20:1 or larger volume, the plasma further reduced the fluorescence intensity to the lowest values. The intensity that was lower than the initial reading was in the negative range.

These results show that plasma from a healthy person had $PLA_2$-stimulating activity (namely $PLA_2$ stimulator or $PLA_2$-s) and $PLA_2$ inhibitory activity (known throughout this application as the specific fraction of albumin causing the inhibitory activity, SFA). Whether $PLA_2$ activity is stimulated or inhibited by plasma in the in vitro reaction depends on the amounts of plasma present in the reaction mixture. In the absence of $PLA_2$ in the reaction mixture, plasma itself (e.g., 4 μl and 30 μl) had little effect on liposome fluorescence intensity (FIG. 12). Similarly, plasma stimulated and inhibited $PLA_2$ from bee venom (*Apis mellifera*) and to a lesser extent $PLA_2$ from snake venom (*Crotalus durissus terrificus*) (FIG. 13). It is noted that the volumes of plasma needed to show the optimal stimulating and inhibitory effects of $PLA_2$ from venom were less than that used in the pancreatic $PLA_2$ studies. This is because the sensitivity of the $PLA_2$ assay varies from batch to batch of the commercial products of $PLA_2$ and phospholipids. In the following studies, a plasma dose-dependent effect on $PLA_2$ was routinely performed for each batch of $PLA_2$ and liposomes to determine the volumes of plasma required to show optimal $PLA_2$-stimulating and -inhibitory activity.

$PLA_2$-s and SFA activities in plasma from healthy lungs vs. inflamed lungs. Interestingly, two different plasma samples from subject N1, one collected when the subject had allergic rhinitis (plasma 092800) and the other one collected when the subject had a viral respiratory infection (plasma 122900), had distinct SFA activity as compared to that shown in FIG. 12. At 5 t these plasma samples exhibited similar $PLA_2$-s activity (FIG. 14) as that shown in FIG. 12. However, at 20 μl these two plasma samples diminished $PLA_2$ and $PLA_2$-s activities only to the baseline values of liposomes (FIG. 14). Later, a plasma sample was collected when the subject was healthy (plasma 022801), and SFA activity was back to the level similar to that shown in FIG. 12 (FIG. 14).

A ratio of the $PLA_2$-s activity (5 μl plasma) over the SFA activity (20 μl plasma) was calculated from each total activity within 2 min period of reaction and named as "$sPLA_2$/SFA ratio." The $PLA_2$-s/SFA ratios of the four plasma samples of N1 subject were determined and each of the samples was assayed two to three times on different days. The ratios are summarized in FIG. 15. The absolute value of the negative ratio was less than 1.5 when blood was withdrawn when subject N1 was healthy (plasma 02/08/01 and plasma Jun. 13, 2001). However, the absolute value of the negative ratio was greater than four when blood was withdrawn when the subject had either allergy (plasma Sep. 28, 2000) or a viral respiratory infection (plasma Dec. 29, 2000). Negative ratio was obtained because of the negative value of total SFA activity. The higher the SFA activity, the lower the absolute value of the negative ratio. Several more plasma samples were obtained from four normal healthy subjects and the effects of these plasma samples on $PLA_2$-s activity were tested; multiple plasma samples were obtained from one subject at different days.

These plasma samples all exhibited $PLA_2$-s (5 μl plasma) and SFA (20 μl plasma) with a $PLA_2$-s/SFA ratio between −1.0 and −1.6 (FIG. 16). In contrast, plasmas collected from three subjects with CF and three subjects with COPD all showed $sPLA_2$ activity, but these plasma samples all had deficient SFA (FIG. 17). The $PLA_2$-s/SFA ratios of these samples ranged from −3.8 to −159 (the greater the absolute value of the negative ratio, the less SFA in the negative fluorescence intensity range). One COPD plasma sample had a ratio of +9.5, which means at 20:1 this sample had a total SFA in the positive range (i.e., greater SFA deficiency). The $PLA_2$-s/SFA ratios of plasma from healthy subjects, subjects with inflammation symptoms, and a smoker are summarized in FIG. 18. The cut-off point of the absolute values of the negative ratio for healthy subjects appears to be less than 2.0 (FIG. 18, light gray area). A negative ratio whose absolute value is greater than 2.0 or a positive ratio is likely associated with inflammation. It is interesting to note that a cigarette smoker, who appeared to be healthy, except for a chronic, intermittently productive cough, had a $PLA_2$-s/SFA ratio value of −2.6.

Distributing $PLA_2$ and SFA in blood and tissues. The patterns of $PLA_2$-s and SFA activities in the sera were similar to that observed in plasma. For example, the $PLA_2$-s/SFA ratios of the sera from two healthy subjects were −1.2 and −0.6, whereas the ratios of the sera from two COPD subjects were −9.6 and −4.0. $PLA_2$-s and SFA activities were found in neutrophils, mononuclear leukocytes, and alveolar macrophages. An example of $PLA_2$-s and SFA activities in neutrophils from a healthy subject and a COPD subject is shown in FIG. 19. SFA deficiency was observed in neutrophils from a subject with COPD. In the presence of 0.1 mg neutrophil proteins from a healthy subject, $PLA_2$ and $PLA_2$-s activities were totally inhibited, whereas even in the presence of 0.4 mg proteins from a COPD subject's neutrophils, no SFA inhibitory activity was observed (FIG. 19). Similarly, SFA was deficient in mononuclear leukocytes and macrophages from subjects with inflamed lungs.

$PLA_2$-s and SFA activities in BALF. BALF from a CF subject stimulated $PLA_2$ activity in a dose-dependent manner and the stimulation reached its optimum at 0.1 mg of BALF protein, indicating the presence of $PLA_2$-s in the fluid (FIG. 20). No SFA activity was detected in the BALF even up to 0.6 mg protein. Similar to the plasma, in the absence of $PLA_2$, BALF itself had no effect on liposome fluorescence intensity. BALFs from normal healthy individuals had little $PLA_2$-s activity under the same assay conditions (FIG. 21A). BALFs from subjects with allergic asthma stimulated $PLA_2$ activity by more than 2-fold (FIG. 21B).

Characterizing $PLA_2$-s and SFA. Incubating plasma in boiling water for 5-10 min considerably diminished SFA activity, but had little effect on $PLA_2$-s activity (FIG. 22). This indicates that SFA and $PLA_2$-s are two different moieties. The molecular weights of $PLA_2$-s and SFA were estimated to be larger than 10 k because both factors were retained in the concentrator with membrane of 10 k molecular weight cut off after BALF or serum was concentrated in the device. Liposomes containing radioactively labeled [1-$^{14}$C]dioleoyl PC were used as $PLA_2$ substrate to determine that the enzymatic products observed in the fluorescently-labeled liposomes were derived from PC hydrolysis. After $PLA_2$ reaction, the amounts of radioactivity were found increasing in fractions of free fatty acids and lysoPC and decreasing in PC, indicating PC hydrolysis. BALFs from CF subjects increased $PLA_2$ activity by nearly 2-fold, whereas the CF BALF itself had no $PLA_2$ activity (FIG. 23). Again, BALFs from normal volunteers had no effect on $PLA_2$ activity (FIG. 23). Heat treatment of CF BALF in boiling water for 5 min also did not diminish PLA2-s activity (FIG. 24). Interestingly, the native lung annexin I and annexin VIII proteins significantly inhibited $PLA_2$ and $PLA_2$-s activities (FIG. 25).

Example 3

Effects of BALF on Pancreatic $PLA_2$ Activity

Continuous Fluorescent Assay. The present invention provides a simple and sensitive continuous fluorescent assay of $PLA_2$ activity using fluorescently labeled unilamellar liposomes as substrate. The unilamellar liposomes were made of dioleoyl phosphatidylcholine (DOPC), phosphatidylglycerol (PG) and fluorescently labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) (Molecular Probes, Eugene, Oreg.) in a molar ratio of 10:10:0.14 as described previously (42). The $PLA_2$ assay was conducted in a single quartz cuvette in which it contained 0.01 M Tris-HCl buffer, pH 7.4, 10 mM $CaCl_2$, 27.3 nmol liposomes phospholipids, and 10 ng porcine pancreatic $PLA_2$. The fluorescence intensity was recorded every 10 sec for 2 min at 21° C. The fluorescence intensity was measured using a Perkin-Elmer Luminescence Spectrometer LS50B equipped with FL WinLab™ software (Perkin-Elmer Instruments, Norwalk, Conn.) at 488 nm excitatopm (slit 2.5) and 530 nm emission (slit 5.0). To test factors that might affect $PLA_2$ activity in the BALF, an aliquot of the specimen was introduced to the reaction mixture prior to the addition of $PLA_2$.

There was no significant fluorescence intensity change in the reaction mixture containing liposomes and calcium without $PLA_2$, or mixture containing liposomes and $PLA_2$ but no calcium (FIG. 26). However, the fluorescence intensity of the mixture containing all three components increased in a time-dependent fashion within 2 min that was $PLA_2$-dose dependent between 5-80 ng and liposome phospholipid-dose dependent between 3-100 nmol (FIG. 26). The florescence intensity increase was due to the release of fluorescently labeled fatty acid and lysoPC from the quenched membrane environment. In the following studies the fluorescence intensity increase of the control $PLA_2$ reaction was maintained at linear range within 2 min (approximately 3-4 units increase at 2 min in the presence of 10 ng $PLA_2$ and 30 nmol liposome phospholipids).

The specimens of BALF from CF patients were obtained and prepared as previously described (41). Adding an aliquot of CF BALF to the $PLA_2$ reaction mixture markedly stimulated the $PLA_2$ activity in a BALF dose-dependent manner (FIG. 27A). The stimulation reached to the optimal level at 100 μg BALF protein. The average percentage of the stimulation by BALF from 4 individuals with CF (100 μg protein per test sample) was 287.46±57.01%. BALF from normal volunteers (NV) had little effect on the $PLA_2$ activity (FIG. 27B). BALF itself had no effect on the fluorescence intensity, indicating that there was no detectable endogenous $PLA_2$ activity in the BALF under the assay conditions. Heat treatment of BALF from subjects with CF in boiling water for 5 min had no significant effect on the $PLA_2$-stimulating activity.

Example 4

Effect of CF BALF on Bee Venom and Rattlesnake Venom $PLA_2$ Activity

The CF BALF that stimulated pancreatic $PLA_2$ also induced bee venom $PLA_2$ but had no effect on the snake venom $PLA_2$ activity (FIG. 28). Although all the secretory $PLA_2$ have similar molecular weights around 14 kDa, the rattlesnake venom $PLA_2$ is distinct from pancreatic and bee venom $PLA_2$ in that it is dimeric in structure and active in the dimeric state (44). These results suggest that the CF BALF stimulation was more specific for pancreatic- and non-pancreatic $PLA_2$ that includes the human $PLA_2$-IB and $PLA_2$-IIA.

Example 5

Isolating and Identifying $PLA_2$-s in the CF BALF

Protein isolation. A pool of BALF from two CF subjects (160 ml) were treated in boiling water for 7 min and the denatured proteins were discarded by centrifugation. The supernatant was concentrated and the concentrate was employed for protein isolation by the methods of gel filtration, anionic exchange, and reverse phase high performance liquid chromatography (HPLC). The $PLA_2$-s activity was traced by using the fluorescent assay. One single protein possessing $PLA_2$-s activity (named $PLA_2$-s) was isolated. The $PLA_2$-s isolated by the reverse phase HPLC showed a single band with an apparent molecular weight of 48 kDa on sodium dodecyl sulfate polyacrylamide (SDS) gel (FIG. 29A). The purified $PLA_2$-s also exhibited $PLA_2$-stimulating activity (FIG. 29B).

Protein structure determination and identification. The protein band of $PLA_2$-s on the SDS gel was excised and digested with trypsin. The trypsin-digested peptides were used for mass and peptide sequence determination by the methods of "matrix-assisted laser desorption ionization" (MALDI) and tandem mass spectrometry (MS/MS) conducted at the Biotechnology Center (UWBC) on the University of Wisconsin campus. The $PLA_2$-s peptide sequences, after searching in the GenBank database, matched human $\alpha$1-AT. The matched peptide sequences are shown in Table 1. SDS gel electrophoresis showed that the apparent molecular weight of the truncated α1-AT was indeed less than the intact human serum α1-AT which is a 52 kDa protein.

TABLE 1

Peptide mass and sequence of $PLA_2$ stimulator isolated from BALF.

| Peptides | Amino acid sequences | | Amino acid residue location at human α1-AT |
|---|---|---|---|
| 1 | IVDLVK | (SEQ ID NO: 2) | 169-174 |
| 2 | LSSWVLLMK | (SEQ ID NO: 3) | 235-243 |
| 3 | LSITGTYDLK | (SEQ ID NO: 4) | 291-300 |
| 4 | GTEAAGAMFLEAIP | (SEQ ID NO: 5) | 344-357 |
| 5 | ITPNLAEFAFSLYR | (SEQ ID NO: 6) | 26-39 |
| 6 | VFSNGADLSGVTEE | (SEQ ID NO: 7) | 311-324 |
| 7 | TLNQPDSQLQLTTG | (SEQ ID NO: 8) | 102-115 |

The native human α1-AT molecular weight is 52 kDa. Apparently, the purified 48 kDa α1-AT from CF BALF was the truncated α1-AT. This finding is consistent with previous report that α1-AT in the BALF from CF patients with inflamed lungs was a 48 kDa proteolytic product. It is known that the truncated α1-AT has no activity against neutrophil elastase (45).

Example 6

Continuous Fluorescent Assay of $PLA_2$

Liposomes were prepared by the method as previously described (40). In this method phospholipids of 2.04 μmol dioleoyl phosphatidylcholine (DOPC), 2.04 μmol phosphatidylglycerol (PG) and 0.02 μmol fluorescenctly labeled 1,2-bis-(4,4-difluoro-5,7-dimethyl-4-bora-3a,4a-diaza-s-indacene-3-undecanoyl)-sn-glycero-3-phosphocholine (Bis-BODIPY FL $C_{11}$-PC) (Molecular Probes, Eugene, Oreg.) were dissolved in about 1 ml chloroform. The chloroform was then evaporated to dryness under a stream of nitrogen. The dried phospholipid residues were suspended in 1.5 ml sucrose/Tris buffer (0.25 M sucrose, 50 mM Tris-HCl, 0.02% sodium azide, pH 7.4). The suspension was stirred occasionally with vortex within 30 min. Then, the phospholipid suspension was sonicated for 30 sec on ice and repeated 6 times using a Virsonic cell disrupter (VirSonic, Gardiner, N.Y.). The 50% PC-50% PG liposomes were stored at 4° C. before use.

The $PLA_2$ assay of the present invention was conducted in a 3 ml quartz cuvette in which 2.96 ml 0.01 M Tris-HCl containing 0.02% sodium azide, pH 7.4, was first added, followed by adding 30 μl of 1 M $CaCl_2$ and 10 μl of liposomes (27.3 mmol phospholipids). The solution was mixed well by three times inversion of the cuvette covered with a piece of parafilm. Then, an aliquot of $PLA_2$ working solution (0.01 μg in 2-3 μl) was added to the reaction mixture followed by rapid inversion of the cuvette three times. Fluorescence intensity was immediately recorded every 10 sec for 2 min at 21° C. (room temperature). The fluorescence intensity was measured using a Perkin-Elmer Luminescence Spectrometer LS50B equipped with FL WinLab™ software (Perkin-Elmer Instruments, Norwalk, Conn.) at 488 nm excitation (slit 2.5) and 530 nm emission (slit 5.0). To test factors that might affect $PLA_2$ activity in the plasma, serum or BALF, an aliquot of the specimen was introduced to the reaction mixture prior to the addition of $PLA_2$ in a final volume of 3 ml. Then, $PLA_2$ was added and fluorescence intensity was recorded. In some tests, the fluorescence intensity of the reaction solution without the presence of $PLA_2$ was recorded for up to 2 min to obtain the background reading.

Determining endogenous $PLA_2$ activity in plasma and synovial fluid by fluorescent assay. To determine the endogenous $PLA_2$ activity in specimens, the assay of the present invention was conducted at 37° C., instead of at room temperature. The reaction components were the same as that described above; 3 ml Tris buffer containing Bis-BODIPY FL $C_{11}$-PC-labeled liposomes (27.3 nmol) and 10 mM $CaCl_2$ in the presence or absence of specimens specified. The cuvette holder of the luminescence spectrometer was connected to a water bath with circulating water that kept the cuvette holder at 37° C. and the buffer was maintained at 37° C. in the water bath. Prior to determining the $PLA_2$ activity in the specimen, the cuvette that contained pre-warmed buffer, liposome and calcium (in the absence or presence of CF BALF) was kept in the cuvette holder to allow the temperature to be equilibrated at 37° C. for 4 min. Then, the specimen to be tested was added to the reaction mixture and the reaction was carried out at 37° C. The fluorescence intensity was recorded every 10 sec for 2 min.

Isolating and characterizing SFA and $PLA_2$-s from human serum—Gel filtration. A total of 14 ml of human sera from healthy volunteers was employed to isolate SFA and $PLA_2$-s. One half of the serum was applied to a Sephadex G100 (Pharmacia, Piscataway, N.J.) column (2.6×55 cm) equilibrated with Tris-EDTA-NaCl buffer (0.01 M Tris-HCl, 5 mM 2-mercaptoethanol, 1 mM EDTA and 0.15 M NaCl, pH 7.4). The proteins were eluted with the Tris-EDTA-NaCl buffer at a flow rate of 12 ml per hour and collected in 2 ml per tube. Protein in each fraction was detected by absorbance at 280 nm and the activities of SFA and $PLA_2$-s were determined by the fluorescent assay. The $PLA_2$-s activity was determined using 40 μl of the fraction and SFA was determined using 150 μl of the fraction. Fractions that contained SFA and $PLA_2$-s activities were pooled, equilibrated with 0.01 M Tris-HCl, pH 7.4, and concentrated to about 1 ml for the next step of isolation. Similarly, the second half of the sera was run through the G100 column by the same manner.

To isolate $PLA_2$-s from BALF, a total of 160 ml BALF collected from two subjects with CF were heated in boiling water for 5 min. The denatured proteins were removed by centrifugation at 10,000 rpm. The supernatant was concentrated to 25 ml. An aliquot of 8 ml of the concentrated supernatant was applied to the Sephadex G100 column as described above. Three runs were performed. Fractions containing $PLA_2$-s activity from all three runs were pooled and concentrated to about 1 ml for next step isolation.

Isolating and characterizing SFA and $PLA_2$-s from human serum: Anionic exchange column chromatography. One half of the SFA/$PLA_2$-s solution (from serum) or $PLA_2$-s solution (from BALF) from Sephadex G100 column was applied to a high performance liquid chromatography (HPLC) anionic exchange MonoQ column (5×50 mm) (Pharmacia) equilibrated with 0.01 M Tris-HCl buffer, pH 7.4. The column was eluted with 0.01 M Tris buffer with an ascending gradient of 1 M NaCl in Tris buffer. The column was first eluted for 10 min with 0.01 M Tris buffer, then with 25% of 1 M NaCl for 100 min, 50% of 1 M NaCl for 30 min, and finally with 100% of 1 M NaCl for 10 min. The flow rate was 1 ml/min and the collected fraction volume was 1 ml per fraction tube. Protein in each fraction was determined by absorbance at 280 nm and the SFA and $PLA_2$-s activities were determined by the fluorescent method.

Isolating and characterizing SFA and $PLA_2$-s from human serum—Reverse phase column chromatography. The SFA/$PLA_2$-s or $PLA_2$-s fractions obtained from HPLC MonoQ column chromatography were pooled, concentrated and applied to a reverse phase HPLC Vydac C4 column (4.6×250 mm, Separations Groups, Hesperia, Calif.). The column was eluted with a gradient of solvent A of 0.1% trifluoroacetic acid (TFA) and solvent B of 0.086% TFA in 80% acetonitrile at a flow rate of 1 ml/min. The proteins were eluted with the following gradient program: 10% B for an initial 2 min, then a gradient of 10-70% B in 60 min. Protein in each fraction was determined by absorbance at 215 nm and 280 nm and the SFA and $PLA_2$-s activities were determined by the fluorescent method.

Isolating and characterizing SFA and $PLA_2$-s from human serum. Sodium dodecyl sulfate polyacrylamide gel electrophoresis (SDS-PAGE). The amounts of proteins were determined by the methods of Lowry et al. (41) with modifications suitable for microtiter plate assay. A specified amount of protein (1-10 μg) was employed for protein separation using a Bio-Rad Mini-PROTEAN 3 Cell Assembly Unit with the use of a 10% SDS Ready gel (Bio-Rad, Hercules, Calif.) under denaturing conditions. Proteins separated on the gel were stained with Coomassie brilliant blue solution followed by destaining.

Structure determination and identification of SFA and $PLA_2$-s. The protein band on the SDS gel was excised and placed into a 0.5 ml microcentrifuge tube. The gel was treated in 100 μl 25 mM $NH_4HCO_3$/50% acetonitrile to remove the Coomassie blue stain. The de-colored gel was dried in a vacuum centrifuge. The protein was reduced in 100 mM dithiothreitol followed by modification with 55 mM iodoacetamide. Then the protein was digested with trypsin (Sequencing Grade Modified, Promega) solution (20 μl of 0.006 mg/ml) at 37° C. for 24 hours. The peptides were collected by washing the gel with water followed by washing with 5% trifluoroacetic acid/50% acetonitrile. The washes were combined and dried in a vacuum centrifuge. The dried peptides were used for mass and peptide sequence determination using the methods of "matrix-assisted laser desorption ionization" (MALDI) and tandem mass spectrometry conducted at University of Wisconsin—Madison Biotechnology Center (UWBC, Madison, Wis.) on campus. The peptides of trypsin-digested protein in SDS gel were also used to determine the amino acid sequences by the tandem mass spectrometry (MS/MS) method using the TOF instruments at UWBC.

Fluorescent assay of phospholipase C (PLC) and lipase. The fluorescent assay of PLC (*Clostridium perfringens*, Sigma) was the same as the fluorescent assay of $PLA_2$, except $PLA_2$ was replaced with a specified amount of PLC (0.01 to 0.05 unit) in the reaction mixture. The fluorescence intensity was recorded every 10 sec for 2 min after PLC was introduced into the reaction mixture. In some studies, an amount of 0.14 unit of porcine pancreatic lipase (Sigma) was added to the reaction mixture after 2 min of PLC reaction. Then, the fluorescence intensity was continuously recorded every 10 sec for another 2 min.

Radioactive labeling of neutrophils (PMN) with $^3$H-arachidonic acid and study of the effects of $PLA_2$, BALF and plasma on $^3$H-PMN. Neutrophils were isolated from peripheral blood from a normal volunteer using the neutrophil isolation media (Polymorphprep™, Axis-Shield PoC AS, Oslo, Norway). A total of $38.6\times10^6$ PMN were obtained from 20 ml peripheral blood. An amount of $5.5\times10^6$ PMN was added to 1 ml RPMI culture medium containing 5% fetal calf serum, 2 mM glutamine, 10 mM HEPES, penicillin (200 U/ml), streptomycin (200 U/ml), amphotericin (500 ng/ml), and 5 μCi $^3$H(N)-AA (Sigma) in a well of a 6-well dish. Neutrophils were cultured at 37° C. in a 5% $CO_2$ incubator for 20 hours. After incubation all radioactively labeled cells were harvested and combined. The medium was removed by centrifugation and cells were washed with 10 ml ice-cold incomplete Hanks balanced salt solution (HBSS) two times. The cells were suspended in 2 ml HBSS and used for $PLA_2$ studies. A small amount of PMN was cultured in non-radioactive medium under the same conditions as that of radioactive labeling of PMN and was used for cell viability and morphology analyses.

$PLA_2$ reaction was conducted in 1 ml HBSS containing 1 mM $CaCl_2$ and $2\times10^6$ $^3$H-labeled PMN in the presence or absence of pancreatic $PLA_2$, BALF, or plasma as specified in a 10-ml culture tube. The reaction tube was incubated at 37° C. for 10 min with frequent shaking. The reaction was stopped on ice followed by centrifugation at 2,000 rpm for 10 min to precipitate the cells. The supernatant was removed; the cells were washed with 10 ml ice-cold HBSS twice and washes discarded. The cells were suspended in 0.1 ml lysis buffer (0.01 M Tris-HCl, 1 mM EDTA, 5 mM 2-mercaptoethanol, 1% Igepal CA-630 nonionic detergent, and 2 mM PMSF, pH 7.4) and sonicated on ice for 30 sec. Lipids in cell homogenate were extracted with chloroform/methanol by the method of Bligh and Dyer (46). Phospholipids, lysophospholipids, neutral lipids and fatty acids were separated by thin-layer chromatography (TLC) and their radioactivity was determined as previously described (43).

Effects of plasma, serum and BALF on $PLA_2$ Activity. The effects of plasma from healthy subjects on $PLA_2$ activity varied depending on the amount of plasma in the assay. In the presence of less than 2.5 μl plasma in the assay mixture, the $PLA_2$ activity expressed as fluorescence intensity increase was stimulated, and the stimulation was plasma dose-dependent (FIG. 30). However, when the volume of plasma in the assay increased, not only $PLA_2$ activity was inhibited, the fluorescence intensity also dropped below the baseline. For example, with the presence of 5 μl of plasma, the fluorescence intensity decreased in the first 30 sec, and then gradually increased afterward. When the plasma volume increased to 10 μl, the fluorescence intensity was reduced to the minimal levels far below the baseline. Further increasing the amount of plasma to 20 μl had nearly the same effect as 10 μl plasma.

Similar results were obtained from plasma samples obtained from several healthy individuals. The inventors observed that 1.75 μl plasma from a number of healthy subjects provided maximal $PLA_2$ stimulating effect and 10 μl plasma was the minimal volume that yielded optimal $PLA_2$ inhibitory effect. In the absence of $PLA_2$, the amounts of plasma ranging from 1.75 μl to 20 μl had no effect on the fluorescence intensity under the assay conditions at room temperature (21° C.) (FIG. 30).

The presence of 1.75 μL of plasma from subjects with CF or COPD also stimulated $sPLA_2$ activity similar to that stimulated by the plasma from healthy subjects. Representative examples are shown in FIG. 31. However, the effects of 10 μl plasma from subjects with CF or COPD had less $sPLA_2$ and fluorescent intensity inhibitory effects than that from healthy subjects. Again, in the absence of $sPLA_2$, the plasma had little effect on the fluorescence intensity under the assay conditions at room temperature (FIG. 31).

The inventors also quantified the total $PLA_2$ activity by adding up each fluorescence intensity change at 10 sec interval within 2 min reaction time. The total fluorescence intensity (TFI) is more reliable than a single reading of the initial rate. Also, because of both stimulating and inhibiting effects of plasma on $sPLA_2$ activity and fluorescence intensity, TFI appears to be more representative of the effects of the plasma.

The TFI of SFA (10 μl plasma) and $PLA_2$-s (1.75 μl plasma) were also determined by the same manner. The average TFI value of 29 different assays of $PLA_2$ was 23.37±4.77. The TFI values of SFA were in the negative range because of fluorescence quenching. Thus, higher negative value of TFI represents higher SFA activity. Among the tested specimens, the TFI values of 10 μl plasma from NV were about 40-50% higher than that from subjects with CF or COPD or from a cigarette smoker (Table 2). However, the $PLA_2$-s activities of all groups were insignificantly different. The plasma albumin levels of CF and COPD subjects were about 5% and 25% lower than that of the normal subjects, respectively (Table 2).

had no significant change after plasma was set on ice for more than 5 hours or stored at −70° C. for more than three days. As described above, CF BALF also contained a $PLA_2$-s (FIG. 33). Much of the experiments and results of BALF $PLA_2$-s isolation and identification are described above.

Determining endogenous $PLA_2$ activity in plasma and synovial fluid. When the fluorescent assay of the present invention was carried out at room temperature, the plasma, either from NV or CF, did not produce any increase in fluorescence intensity (FIGS. 30 and 31), i.e., no endogenous $PLA_2$ activity in the plasma could be determined. However, when the assay temperature increased to 37° C., plasma in the reaction mixture caused a time-dependent increase in fluorescence intensity without adding porcine pancreatic $PLA_2$. The total fluorescent intensity generated by the plasma increased with increasing amounts of plasma (from 1 to 2.5 μl) in the reaction mixture (Table 3). The increase in fluorescence intensity was probably due to factors other than $PLA_2$ in the plasma. This is probably why there was no apparent difference in the total fluorescent intensity between NV and CF plasma.

However, the presence of heat-treated CF BALF in the reaction mixture increased the fluorescence intensity of the CF plasma, but the stimulation diminished with plasma volume greater than 2.5 μl. In contrast, CF BALF had little effect on the fluorescence intensity of NV plasma among the tested samples ranging from 1 to 2.5 μl plasma (Table 3). The reaction mixture contained 27.3 nmol PC-PG (50%-50%) UL labeled with Bis-BODIPY FL $C_{11}$-PC, 10 mM $CaCl_2$ in 3 ml 0.01 M Tris-HCl, pH 7.4 under conditions described in the Table. The assay was conducted at 37° C. for 2 min. Therefore, it is likely that the increase in fluorescence intensity in the CF plasma caused by CF BALF was due to the stimulation of the endogenous $PLA_2$ activity in the CF plasma by CF BALF.

TABLE 2

Total fluorescence intensity (TFI) of SFA and PLA2-s and amount of albumin in plasma.

| | SFA (TFI) | | $PLA_2$-s (TFI) | | | Albumin | |
|---|---|---|---|---|---|---|---|
| Sample | Mean ± SD | % | Mean ± SD | % | s/I Ratio | Mean ± SD | % |
| Normal | −61.89 ± 5.61 (16) | 100 | 70.96 ± 18.95 (16) | 100 | −1.14 ± 0.26 | 3.9 ± 0.2 (8) | 100 |
| (Range) | (−53.10 to −74.11) | | (67.65 to 113.39) | | (−0.84 to −1.72) | | |
| CF | −37.22 ± 10.51 (7)* | 60.1 | 79.69 ± 20.04 (7) | 112.3 | −2.40 ± 1.20 | 3.7 ± 0.3 (5) | 94.9 |
| (Range) | (−18.02 to −50.61) | | (52.83 to 114.14) | | (−1.20 to −4.61) | | |
| COPD | −27.59 ± 14.56 (4)* | 44.6 | 56.65 ± 14.13 (4) | 79.8 | −2.59 ± 1.55 | 2.9 ± 0.4 (3) | 74.4 |
| (Range) | (−14.27 to −43.64) | | (37.69 to 64.52) | | (−1.16 to −4.62) | | |
| Smoker | −34.49 | 55.7 | 64.89 | 91.4 | −2.62 | | |

Numbers of samples are shown in parenthesis.

*p < 0.05 (t-test) compared to NV.

The value of TFI of the control $PLA_2$ was 23.37 ± 4.77 of 29 assays.

The activities of $PLA_2$-s or SFA were also present in the serum (FIG. 32). Heat treatment of serum in boiling water for 5 min had markedly different effects on the SFA and $PLA_2$-s activities. With 1.75 μl heat-treated serum, the stimulating activity was nearly totally diminished. With 10 μl plasma, the inhibitory activity was completely abolished; instead, it showed stimulating activity. Increasing plasma to 20 μl or 40 μl still had no inhibitory activity; there was only stimulating activity. The stimulating activity reached the maximal level with 10 μl of serum. These results suggest that there are probably two separate factors, a heat-liable inhibitor (SFA) and a heat-stable stimulator ($PLA_2$-s) in the serum or plasma that affect the $PLA_2$ activity.

Plasma was isolated within 60 min after blood was drawn. Both $PLA_2$-s and SFA activities in the freshly isolated plasma

TABLE 3

Fluorescent assay of endogenous $PLA_2$ activity in plasma and the effect of CF BALF.

| Condition | Plasma volume (μl) | $PLA_2$ activity (TFI) | % control |
|---|---|---|---|
| Experiment 1 | | | |
| CF1 Plasma (control) | 1 | 6.23 | |
| CF1 Plasma + CF BALF* | 1 | 16.00 | 256.9 |
| CF1 Plasma (control) | 1.25 | 16.27 | |
| CF1 Plasma + CF BALF* | 1.25 | 25.17 | 154.7 |
| CF1 Plasma (control) | 2.5 | 38.28 | |
| CF1 Plasma + CF BALF* | 2.5 | 39.66 | 103.6 |

TABLE 3-continued

Fluorescent assay of endogenous $PLA_2$ activity in plasma and the effect of CF BALF.

| Condition | Plasma volume (μl) | $PLA_2$ activity (TFI) | % control |
|---|---|---|---|
| Experiment 2 | | | |
| CF2 Plasma (control) | 1 | 5.16 | |
| CF2 Plasma + CF BALF* | 1 | 11.16 | 216.3 |
| CF1 Plasma (control) | 1.5 | 7.86 | |
| CF1 Plasma + CF BALF* | 1.5 | 11.88 | 151.1 |
| CF1 Plasma (control) | 1.5 | 9.10 | |
| CF1 Plasma + CF BALF* | 1.5 | 12.88 | 141.5 |
| CF3 Plasma (control) | 1.5 | 8.39 | |
| CF3 Plasma + CF BALF* | 1.5 | 12.0 | 143.0 |
| NV plasma | | | |
| Plasma (control) | 1 | 6.68 | |
| Plasma + CF BALF* | 1 | 7.52 | 112.6 |
| Plasma (control) | 1.5 | 15.34 | |
| Plasma + CF BALF* | 1.5 | 14.31 | 93.3 |
| Plasma (control) | 2.5 | 44.22 | |
| Plasma + CF BALF* | 2.5 | 45.90 | 125.3 |

*Heat-treated CF BALF with 100 μg protein.

The $PLA_2$-s in the CF plasma stimulated by CF BALF was probably the secretory $PLA_2$-IIA, a subform of $PLA_2$ whose level increases in the circulating blood of patients with inflammatory diseases. Because $sPLA_2$-IIA is enriched in rheumatoid arthritis synovial fluid (12, 13), the inventors further tested the effect of CF BALF on synovial fluid $PLA_2$ activity using the fluorescent assay method of the present invention. When the fluorescent assay was carried out at 37° C., synovial fluid also increased total fluorescent intensity in a dose-dependent manner (Table 4). Similar to that observed with plasma, CF BALF stimulated synovial fluid $PLA_2$ activity and the stimulation decreased with increasing synovial fluid volume (Table 4). The reaction mixture contained 27.3 nmol PC-PG (50%-50%) UL labeled with Bis-BODIPY FL $C_{11}$-PC, 10 mM $CaCl_2$ in 3 ml 0.01 M Tris-HCl, pH 7.4 under conditions described in the Table. The assay was conducted at 37° C. for 2 min.

TABLE 4

Fluorescent assay of endogenous $PLA_2$ activity in synovial fluid and effect of CF BALF.

| Conditions | SF quantity | $PLA_2$ activity (TFI) | % Of control |
|---|---|---|---|
| Synovial fluid (control) | 12.5 μl | 18.62 | |
| | 12.5 μl | 18.05 | |
| | 12.5 μl | 17.41 | |
| Synovial fluid + BALF[b] | 12.5 μl | 30.22 | 167.6 |
| | 12.5 μl | 22.80 | 126.5 |
| | 12.5 μl | 28.38 | 157.4 |
| Synovial fluid (control) | 25 μl | 21.76 | |
| Synovial fluid + BALF[b] | 25 μl | 34.32 | 157.8 |
| Synovial fluid (control) | 50 μl | 36.64 | |
| Synovial fluid + BALF[b] | 50 μl | 44.71 | 122.0 |

[a]The reaction mixture temperature was equilibrated to 37° C. prior to addition of synovial fluid or $PLA_2$
[b]Heat-treated CF BALF with 100 μg protein.

Because the catalytic activities of all secreted $PLA_2$ enzymes in vitro are alike, apparently the CF BALF stimulated the secretory $PLA_2$ activity including the pancreatic $PLA_2$ ($PLA_2$-IB) and $PLA_2$-IIA. For convenience, the inventors used the commercially-available porcine pancreatic $PLA_2$ as the enzyme source in this study.

Radioactively labeled PMN assay. To investigate whether the effects of CF BALF and plasma on $PLA_2$ are biologically significant, the inventors conducted experiments using $^3$H-phospholipid labeled PMN as substrate, instead of liposomes, to test the effects of CF BALF and plasma on $PLA_2$ activity. The inventors observed that after overnight incubation of PMN with $^3$H-AA in the culture medium, over 80% of total radioactivity ($2.17\times10^4$ CPM) in the lipid fraction was associated with PC. The inventors determined CPM of lysoPC representing hydrolysis of PC catalyzed by $PLA_2$. The results showed that $PLA_2$ alone did not significantly hydrolyze PMN phospholipids (Table 5). Neutrophils isolated from normal volunteer peripheral blood were cultured in medium containing $^3$H-AA for 22 hours.

However, in the presence of CF BALF, $PLA_2$ hydrolyzed PMN PC. The inventors also observed that in the presence of NV plasma, $PLA_2$ did not hydrolyze PMN PC, but CF plasma significantly induced PC hydrolysis catalyzed by $PLA_2$. These results suggest the biological importance of the stimulation of $PLA_2$ by CF BALF and plasma. Isolation and identification of the factors in the CF BALF and plasma were attempted.

TABLE 5

Effects of BALF and plasma on neutrophil phospholipid degradation hydrolyzed by pancreatic $PLA_2$.

| Experimental conditions | Lyso phospholipids (cpm) |
|---|---|
| PMN control | 2335.05 |
| PMN control | 1793.48 |
| PMN + CF BALF | 2242.45 |
| PMN + CF BALF | 3172.00 |
| PMN + $PLA_2$ | 1787.47 |
| PMN + $PLA_2$ | 1925.24 |
| PMN + CF BALF + $PLA_2$ | 4555.00 |
| PMN + CF BALF + $PLA_2$ | 3766.77 |
| PMN + NV plasma | 1682.84 |
| PMN + CF plasma | 1639.24 |
| PMN + NV plasma + $PLA_2$ | 1754.34 |
| PMN + CF plasma + $PLA_2$ | 3447.64 |

Isolating, characterizing and identifying SFA and $PLA_{2-s}$ from human serum and $PLA_2$-s from human BALF. Some of the results of isolation and identification of $PLA_2$-s in CF BALF that were presented above are repeated in this example so that the properties of BALF $PLA_2$-s can be compared with that of serum $PLA_2$-s.

Gel filtration. After serum was applied to the Sephadex G100 column, most SFA and $PLA_2$-s activities were in fractions containing proteins in the range of molecular weights between 10 k-70 k (FIG. 33, Fractions #70-90). A small amount of SFA and $PLA_2$-s activities was found in fractions containing high molecular weight proteins (Fractions #54-67). The high molecular weight SFA and $PLA_2$-s was probably a product of protein aggregation. In this study the inventors focused on the isolation of SFA and $PLA_2$-s in the low molecular weight fractions between #70 and #90.

After BALF proteins were eluted from Sephadex G100 column, the $PLA_2$-s activity was determined in the same number fractions as that of serum proteins (FIG. 35). No SFA activity was determined in all fractions.

Anionic exchange HPLC. After the serum protein fractions collected from Sephadex G100 column were applied to the anionic exchange MonoQ column, most SFA and $PLA_2$-s activities were found in the fractions eluted between 0.07 M and 0.17 M NaCl gradient (between 60 to 90 min elution time) (FIG. 36). The protein profile in these fractions had broad multiple protein peaks that overlapped one another. The SFA activity was more narrowly concentrated in fractions between 65 and 75 min elution time than $PLA_2$-s. Up till this step, SFA and $PLA_2$-s were not separable by the methods of column chromatography described. The next step the inventors employed used the reverse phase HPLC Vydac C4 column to isolate SFA and $PLA_2$-s. The fractions eluted between 60 and 90 min from MonoQ column were divided into four groups with each group having the same number of fractions in consecutive order. The fractions of each group were pooled, concentrated, and equilibrated in 0.01 M Tris-HCl buffer (pH 7.4) for applying to the reverse phase HPLC.

The protein profile of BALF eluted from MonoQ column was different from the serum proteins (FIG. 37). Fractions between 42 and 87 min elution time were divided into four groups. Fractions of each group in successive order were pooled and concentrated as described above for reverse phase HPLC.

Reverse phase HPLC. Two major protein peaks, namely protein-I and protein-II, were obtained from the reverse phase HPLC chromatograms of the serum samples (FIG. 38A). The amount of serum Protein-II was about 3% of protein-I. Because the organic solvents used for the reverse phase HPLC interfered with the $PLA_2$ fluorescent assay, all protein fractions were re-equilibrated with 0.01 M Tris-HCl buffer, pH 7.4, and concentrated. Most BALF proteins were eluted from the column within the same time range of the serum proteins (FIG. 39B).

Characterizing purified SFA and $PLA_2$-s. Both serum proteins I and II and BALF protein-II were highly purified as each of these proteins exhibited a single band on the SDS gel. The serum protein-I and protein-II had the same molecular weight around 52 kDa, whereas the BALF protein-II had an apparent molecular weight around 48 kDa.

The fluorescent assay demonstrates that protein-I has both $PLA_2$-inhibiting and $PLA_2$-stimulating activities (FIG. 39). At low protein levels (e.g., less than 30 μg), protein-I stimulated $PLA_2$. However, when the amount of protein increased to 60 to 100 μg, protein-I showed $PLA_2$ inhibitory activity in the beginning of the reaction and then showed $PLA_2$ stimulating activity. At high protein levels (e.g., 256 μg), protein-I totally inhibited $PLA_2$ activity and reduced the fluorescence intensity far below the baseline (FIG. 39A). Contrarily, protein-II at a wide range of protein concentrations exhibited only $PLA_2$-stimulating activity (FIG. 38B).

After treating the protein in boiling water for 5 min, protein-II lost less than 20% of its activity, whereas protein-I lost all of its stimulating and inhibiting activities. The activity properties of protein-I and protein-II were consistent with that observed with the plasma or serum as described above. Although protein-II isolated from BALF had lower molecular weight than the protein-II isolated from serum, it also exhibited $PLA_2$-s activity and was heat stable (FIG. 40). The purified serum $PLA_2$-s and BALF $PLA_2$-s had similar levels of the $PLA_2$-stimulating activity at 61 g protein in the assay. Thus, the inventors concluded that protein-I was SFA and protein-II was $PLA_2$-s.

Structure determination and identification of SFA and $PLA_2$-s. The peptide amino acid sequences of trypsin-digested serum SFA and $PLA_2$-s and BALF $PLA_2$-s determined by mass spectrometry are shown in Table 6. Database search revealed that all determined serum SFA peptides matched human albumin and all determined serum $PLA_2$-s and BALF $PLA_2$-s peptides matched human α1-AT. This confirms that serum SFA was albumin and serum $PLA_2$-s was α1-AT. Because serum α1-AT had a molecular weight of 52 kDa and BALF $PLA_2$-s had a mass of 48 kDa, this suggests that BALF $PLA_2$-s was a truncated α1-AT. The cleavage site of α1-AT to form the truncated α1-AT in CF respiratory secretion had not been previously determined. In this invention the inventors determined that the N-terminal sequence of the truncated α1-AT was HDQDHPTFNKIT, indicating that α1-AT was cleaved between His15 and His 16 bond in CF respiratory secretions. Because the truncated α1-AT molecular weight was 4 kDa less than α1-AT, this suggests that cleavage at the C-terminus must also occur, such as at the Pro357-Met358 bond (47-49).

TABLE 6

Results of tandem mass spectrometry (MS/MS) of trypsin in-gel digested SFA and $PLA_2$-s.

| Peptides | Observed m/z | Expected m/z | Calculated m/z | | |
|---|---|---|---|---|---|
| | SFA from serum | | | Human albumin peptides | |
| 1 | 302.18 | 301.18 | 303.15 | ER | |
| 2 | 508.24 | 507.23 | 507.24 | FGER | (SEQ ID NO: 9) |
| 3 | 927.49 | 926.49 | 926.49 | YLYEIAR | (SEQ ID NO: 10) |
| 4 | 100.61 | 999.61 | 999.60 | QTALVELVK | (SEQ ID NO: 11) |
| 5 | 1149.63 | 1148.62 | 1148.61 | LVNEVTEFAK | (SEQ ID NO: 12) |
| 6 | 671.82 | 1341.62 | 1341.63 | AVMDDFAAFVEK | (SEQ ID NO: 13) |
| 7 | 820.47 | 1638.92 | 1638.93 | KVPQVSTPTLVEVS | (SEQ ID NO: 14) |
| 8 | 955.97 | 1909.93 | 1909.92 | RPCFSALEVDETYV | (SEQ ID NO: 15) |
| 9 | 682.36 | 2044.07 | 2044.09 | VFDEFKPLVEEPQN | (SEQ ID NO: 16) |
| | $PLA_2$-s from serum | | | Human alpha 1-antitrypsin | |
| 1 | 474.26 | 473.26 | 473.28 | LVDK | (SEQ ID NO: 17) |
| 2 | 532.24 | 531.23 | 531.27 | ELDR | (SEQ ID NO: 18) |
| 3 | 605.27 | 604.28 | 604.31 | VPMMK | (SEQ ID NO: 19) |

TABLE 6-continued

Results of tandem mass spectrometry (MS/MS) of trypsin in-gel digested SFA and $PLA_2$-s.

| Peptides | Observed m/z | Expected m/z | Calculated m/z | | |
|---|---|---|---|---|---|
| 4 | 390.17 | 778.32 | 778.40 | SPLFMGK | (SEQ ID NO: 20) |
| 5 | 504.7 | 1007.39 | 1007.49 | QINDYVEK | (SEQ ID NO: 21) |
| 6 | 555.75 | 1109.48 | 1109.60 | LSITGTYDLK | (SEQ ID NO: 4) |
| 7 | 601.93 | 1802.77 | 1802.95 | LQHLENELTHDIIT | (SEQ ID NO: 22) |
| 8 | 917.88 | 1833.74 | 1832.92 | VFSNGADLSGVTEE | (SEQ ID NO: 7) |
| 9 | 1288.09 | 2574017 | 2573.33 | TLNQPDSQLQLTTG | (SEQ ID NO: 8) |
| | $PLA_2$-s from BALF | | | Human alpha 1-antitrypsin | |
| 1 | 686.44 | 685.43 | 685.44 | IVDLVK | (SEQ ID NO: 2) |
| 2 | 538.8 | 1075.58 | 1075.61 | LSSWVLLMK | (SEQ ID NO: 3) |
| 3 | 1110.62 | 1109.61 | 1109.60 | LSITGTYDLK | (SEQ ID NO: 4) |
| 4 | 754.85 | 1507.69 | 1507.71 | GTEAAGAMFLEAIP | (SEQ ID NO: 5) |
| 5 | 821.42 | 1640.83 | 1640.86 | ITPNLAEFAFSLYR | (SEQ ID NO: 6) |
| 6 | 917.46 | 1832.90 | 1832.92 | VFSNGADLSGVTEE | (SEQ ID NO: 7) |
| 7 | 858.77 | 2573.28 | 2573.33 | TLNQPDSQLQLTTG | (SEQ ID NO: 8) |

Effects of $PLA_2$-s and SFA on PLC activity. It has been shown that a number of proteins can stimulate $PLA_2$ activity by depleting product inhibition (15). As shown above, while CF BALF could stimulate pancreatic $PLA_2$ and bee venom $PLA_2$, it had little effect on snake venom $PLA_2$. This suggests that stimulating pancreatic or bee venom $PLA_2$ by truncated α1-AT was not due to product inhibition depletion. The inventors speculated that truncated α1-AT might interact with membrane phospholipid head group and enhance $PLA_2$ penetration. Unlike pancreatic and bee venom $PLA_2$, snake venom $PLA_2$ acts as a dimer that was probably not affected by truncated α1-AT-membrane interaction.

To test this hypothesis, the inventors tested the effect of intact and truncated α1-AT on PLC, an enzyme that cleaves the phosphate bond on phospholipids to yield diacylglycerol. The inventors employed the fluorescent method to determine PLC activity. Unlike the $PLA_2$ reaction, the FI decreased in the presence of PLC in the reaction mixture and the decrease was PLC-dose dependent (FIG. 41). The decrease in FI was because of the release of more hydrophobic diacylglycerol from PC into the environment that caused fluorescence quenching. When pancreatic lipase was added to the reaction mixture after 2 min of PLC reaction, the fluorescence intensity markedly increased with time because of the hydrolysis of diacylglycrol and the release of fluorescent-labeled fatty acid (FIG. 41). In the absence of PLC in the reaction mixture, lipase only yielded a moderate increase in FI, presumably due to contamination of pancreatic $PLA_2$ in the commercial product.

Interestingly, the purified serum $PLA_2$-s (intact α1-AT) and BALF $PLA_2$-s (truncated α1-AT) effectively inhibited PLC activity, but they had no effect on the lipase activity (FIG. 42). However, an amount of serum SFA (albumin) that was 5 to 10-times more than $PLA_2$-s had little effect on the PLC activity.

Effects of commercial products of human albumin and α1-AT on $PLA_2$ activity. Two different human serum albumin products, one globulin free (A8763) and one fatty acid free (A3782) were purchased from Sigma Chemical Co. The fatty acid-free albumin, as described in Sigma product information sheet, was prepared from globulin-free product. The fatty acid-free albumin exhibited the stimulating and inhibitory effects on $PLA_2$ similar to that shown by the purified SFA and plasma (FIG. 43A). Although the globulin-free albumin stimulated PLA2 similarly as the fatty acid-free albumin, it had much less $PLA_2$ inhibitory activity (FIG. 43B). It appeared that more Sigma albumin was needed to display the effects on $PLA_2$ than the newly purified SFA. For example, Sigma fatty acid free albumin at 320 μg displayed similar inhibitory and stimulating effects as 128 μg of the newly isolated SFA. This was not due to impurity in Sigma protein because the Sigma albumin showed only a single protein band and migrated at the same distance as SFA on the SDS gel.

It is known that the broad protein peak of albumin as seen on anionic column chromatogram is a result of oxidation of the SFA sulfhydryl group (18). It is interesting to note that $PLA_2$-s activity distributed along the broad protein peak, whereas SFA activity was found mainly in the major protein peak (FIG. 36). The major protein peak is known to be the SFA which has the lowest fatty acid content among other forms of albumin (18). This seems consistent with the results that the commercial product of fatty acid-free albumin had much higher SFA activity than the globulin-free albumin (FIG. 43). Even the fatty acid-free albumin also has heterogeneous forms of albumin (47). This may explain that twice the amount of commercial product of fatty acid-free albumin was required to reach the optimal SFA activity as compared to the purified SFA. These results imply that deficient SFA activity in albumin, such as resulted from oxidation or high content of fatty acid binding, may impair its function as a regulator in $PLA_2$-mediated inflammation processes.

Human serum α1-AT was obtained from Sigma Chemical Co. and it stimulated $PLA_2$ activity and inhibited PLC activity similar to that displayed by the purified serum and BALF $PLA_2$-s (FIG. 44A). In addition, the $PLA_2$-stimulating activity and PLC-inhibiting activity (FIG. 44B) of the commercial product of α1-AT was not affected by heating the protein in boiling water for 5 min.

Effects of phospholipid membrane charge on $PLA_2$ stimulation by truncated α1-AT To determine whether stimulating $PLA_2$ by truncated α1-AT was phospholipid-charge dependent, the inventors prepared three different groups of liposomes: 100% PC liposomes, 90% PC-10% PG liposomes, and 50% PC-50% PG liposomes. In the $PLA_2$ fluorescent assay the inventors used each of these groups of liposome as substrate to test the effects of truncated α1-AT on $PLA_2$ activity. The results show that $PLA_2$ did not hydrolyze 100% PC liposome phospholipid (e.g., no fluorescence intensity increase) even at 37° C.; truncated α1-AT also did not stimulate $PLA_2$ activity (FIG. 45A). Using 90% PC-10% PG liposome as substrate, $PLA_2$ increased fluorescence intensity in a $PLA_2$-dose dependent manner, but the presence of truncated α1-AT did not significantly enhance the $PLA_2$ activity (FIG. 45A). However, with 50% PC-50% PG liposome as substrate, $PLA_2$ not only exhibited an enzyme dose-dependent activity, its activity was two-times higher than that with 90% PC-10% PG liposomes (FIG. 45B). Also, with 50% PC-50% PG liposome as substrate, $PLA_2$ activity was markedly stimulated by truncated α1-AT (FIG. 45B).

Effect of mixing lysoPC and truncated α1-AT or intact α1-AT on $PLA_2$ activity was also determined by the fluorescent assay. The reaction mixture containing 27.3 nmol UL, 10 mM $Ca^{2+}$ in the absence or presence of specified amount of egg yolk lysoPC, truncated α1-AT, intact α1-AT, or human serum albumin in 3 ml Tris buffer (pH 7.4) was incubated at 37° C. for 2 min followed by addition of 5 ng $PLA_2$. Reaction was continued at 37° C. for 2 min. Total fluorescence intensity (TFI) within 2 min was determined as described in the materials and methods section. As shown in Table 7, pre-incubation of truncated or intact α1-AT with lysoPC, a $PLA_2$ product that causes fluorescence intensity increase in the fluorescent assay, had little effect on $PLA_2$-stimulating effect.

TABLE 7

Effect of mixing lysoPC and truncated α1-AT or intact α1-AT on $PLA_2$ activity determined by the fluorescent assay.

| Experimental condition | TFI | % of control |
|---|---|---|
| $PLA_2$ (5 ng) (control) | 37.62 | 100 |
| Truncated α1-AT (6 μg, 0.12 nmol) + $PLA_2$ (5 ng) | 57.23 | 152.1 |
| Intact α1-AT (20 μg, 0.38 nmol) + $PLA_2$ (5 ng) | 68.96 | 183.3 |
| LysoPC (9 nmol) + $PLA_2$ (5 ng) (control) | 19.70 | 100 |
| LysoPC (9 nmol) + Truncated α1-AT (6 μg, 0.12 nmol) + $PLA_2$ (5 ng) | 31.82 | 161.6 |
| LysoPC (9 nmol) + Intact α1-AT (20 μg, 0.38 nmol) + $PLA_2$ (5 nmol) | 29.81 | 151.4 |
| $PLA_2$ (5 ng) (control) | 47.43 | 100 |
| Albumin (20 μg, 0.32 nmol) + $PLA_2$ (5 ng) | 66.20 | 139.6 |
| LysoPC (9 nmol) + $PLA_2$ (5 ng) (control) | 40.68 | 100 |
| LysoPC (9 nmol) + Albumin (20 μg, 0.32 nmol) + $PLA_2$ (5 ng) | 46.01 | 113.1 |
| $PLA_2$ (5 ng) (control) | 24.23 | 100 |
| Albumin (20 μg, 0.32 nmol) + $PLA_2$ (5 ng) | 48.19 | 198.9 |
| LysoPC (9 nmol) + $PLA_2$ (5 ng) (control) | 23.75 | 100 |
| LysoPC (9 nmol) + Albumin (20 μg, 0.32 nmol) + $PLA_2$ (5 ng) | 35.91 | 151.2 |

Inhibiting $PLA_2$ and truncated α1-AT activity by annexin. The inventors previously described that lung annexins (annexin I and annexin VIII) inhibited $PLA_2$ activity and suppressed the stimulation of $PLA_2$ by CF BALF using the radioactively labeled liposome method (30) (FIG. 46A). Here, using the fluorescent assay of the present invention, the inventors also demonstrate that annexin I markedly inhibited both $PLA_2$ activity and the effect of truncated α1-AT on $PLA_2$ stimulation (FIG. 46B).

Example 7

Endogenous Serum sPLA2-Induced Activity

The activity of serum specific fraction of albumin (SFA) is regulated by the secretory phospholipase $A_2$ ($sPLA_2$). To determine the endogenous $sPLA_2$-induced SFA activity, it is necessary to quantify the $sPLA_2$ activity to correlate with the SFA activity. The inventors have recently developed a new $sPLA_2$ fluorescent assay substrate that is specific for $sPLA_2$ and more sensitive and stable than the substrates previously used.

An amount of 2 mg of 100% phosphatidylglycerol (PG) and 0.014 mg of BODIPY-PC are dissolved in 1 ml 100% ethanol and stored at −20° C. before use. The mixture of PG-BODIPY-PC in ethanol is stable at −20° C. over a six-month period, more stable than liposomes composed of the same components that are prepared in buffer following sonication. Preparation of PG-BODIPY-PC in ethanol does not require sonication.

After the components are dissolved in ethanol, the ethanol solution can be used for determining sPLA2 activity in biological samples including serum (plasma) or tissues. The assay using ethanol PG-BODIPY-PC solution is also simpler than using a liposomal PG-BODIPY-PC substrate that requires sonication. An example of using a 96-well microplate for a triplicate assay with using PG-BODIPY-PC ethanol solution as substrate and human serum sPLA2 as the enzyme source is described as follows.

An amount of 0.099 ml of 0.01 M Tris-HCl buffer containing 10 mM $CaCl_2$ (pH 7.4) is added to each well followed by addition of 11 of serum and mixing. An amount of 9.9 μl of PG-BODIPY-PC ethanol solution is added to a 0.66 ml of 0.01 M Tris-HCl-10 mM $CaCl_2$ buffer in a trough, mixed thoroughly, and then an aliquot of 0.2 ml of the substrate-buffer mixture is added to each well using a multiple tips pipette with gentle mixing. The reaction mixture in each microplate well contains 11 of serum and 31 of substrate in a final volume of 0.3 ml. The microplate is immediately placed in a temperature-controlled (30° C.) microplate reader (PerkinElmer microplate reader accessory) attached to a PerkinElmer Luminescence Spectrometer LS50B (PerkinElmer Instruments, Norwalk, Conn., USA). The fluorescence intensity (FI) in each well is recorded every 20 sec for 90 cycles at 488 nm excitation (excitation slit: 2.5 nm) and 530 nm emission (emission slit: 5.0 nm). To assay $sPLA_2$ in the presence of EGTA, 0.01 M Tris-HCl (pH 7.4) containing 10 mM $Ca^{2+}$ and 20 mM EGTA is used as the assay buffer.

A comparison of the activity of $sPLA_2$-IIA in human serum as measured using 100% PG-BODIPY-PC in ethanol and 100% PG-BODIPY-PC liposomes prepared in sucrose-Tris buffer (Tsao, et al. Clin Chim Acta 2007; 379:119-126) is shown in FIGS. 47 and 48. The advantages of using 100% PG and BODIPY-PC in ethanol over liposomes in buffer are several: (1) omit sucrose-Tris buffer, (2) easy to prepare, (3) stable at −20° C. for storage, and (4) enhance sPLA2 activity (FIGS. 47-48).

Example 8

Continuous $PLA_2$ Fluorescent Assay

Materials. Porcine pancreatic $PLA_2$, dioleoyl phosphatidylcholine (DOPC), phosphatidylglycerol (PG), globulin free albumin, and fatty acid free albumin were purchased from Sigma Chemical (St. Louis, Mo.). Fluorescence labeled bis-BODIPY, $C_{11}$-PC (1,2-bis-(4,4-difluoro-5,7-dimethyl-4-bora-3a,4a-diaza-s-indacene-3-undecanoyl)-sn-glycero-3-phosphocholine) (BODIPY-PC) and C1-BODIPY® C12 (4,4-difluoro-5-methyl-4-bora-3a,4a-diaza-s-indacene-3-dodecanoic acid) (BODIPY-FA) were obtained from Invitrogen Molecular Probes (Eugene, Oreg.). Sequencing grade-modified trypsin was from Promega (Madison Wis.). Recombinant human $sPLA_2$-IIA was kindly provided by Dr. Wonhwa Cho in the Department of Chemistry, University of Illinois at Chicago, Ill., USA.

Isolating human plasma and serum. Obtaining serum samples from human subjects was approved by the Institutional Review Board of the University of Wisconsin School of Medicine and Public Health. Informed consent was obtained from all subjects or their authorized representatives for the collection of the samples. Serum samples were obtained from adult healthy volunteers and patients. For isolating plasma, blood from the subjects was drawn into vacutainer tubes containing 15% (w/v) $K_3$EDTA (BD, Franklin Lake, N.J., USA). The tubes were centrifuged at 2,000×g for 20 min at 16° C. to obtain plasma. For isolating serum, peripheral blood was centrifuged at 2,000×g for 20 min after clotting taking place. Patients diagnosed with chronic obstructive pulmonary disease (COPD) and patients with sepsis (sampled at the time of diagnosis) were recruited in this study. Septic shock was diagnosed according to clinical criteria defined as the presence of a suspected or known infection and sepsis-induced dysfunction of at least one organ (cardiovascular, renal, respiratory, hematologic, or unexplained metabolic acidosis). Eligible patients were admitted to the intensive care unit at University of Wisconsin Hospitals and Clinics, Madison, Wis. Patients were excluded from the study if they were admitted to intensive care unit more than three hours after suspicion of sepsis or if they received antibiotic treatment prior to enrollment and obtaining of the blood sample. Investigators were blinded to patients' clinical course and outcome and the patients received treatment at the discretion of their clinicians.

Determining $sPLA_2$ activity and $sPLA_2$-plasma (serum, albumin)-BODIPY-PC-liposome interactions. The $PLA_2$ assay of the present invention was conducted using liposomes composed of 50% DOPC-50% PG labeled with BODIPY-PC as the substrate either in a 3-ml quartz cuvette or in a 96-well plate (33). The reaction mixture of the assay carried out in a quartz cuvette contained 10 mM $CaCl_2$, 20 µg liposome phospholipids, and 10 ng $PLA_2$ in a final volume of 3 ml of 0.01M Tris-HCl, pH 7.4. The amounts of all the components in the reaction mixture were reduced 10-fold when the assay was conducted in a microplate well. The commercially-available porcine pancreatic $PLA_2$ was mainly used as the enzyme source in this study. The $PLA_2$ working solution (2.5 µg of protein in 0.5 ml 0.01 M Tris-HCl, pH 7.4) was freshly prepared before use.

To determine the interactions between $PLA_2$ and albumin or serum, the substrates of 50% DOPC-50% PG liposomes labeled with BODIPY-FA were used in some of the assays. DOPC-PG-BODIPY-FA liposomes were prepared by mixing 2 mg DOPC, 2 mg PG, and 0.032 mg BODIPY-FA in chloroform. The stock solution of BODIPY-FA was prepared by dissolving 1 mg BODIPY-FA in 1 ml of methanol. The chloroform of the DOPC-PG-BODIPY-FA solution was evaporated to dryness and liposomes were prepared in 2 ml sucrose-Tris buffer (0.25 M sucrose, 50 mM Tris-HCl, 0.02% sodium azide) as described previously (33).

The reaction was initialized by adding the protein solution ($PLA_2$, serum, plasma, or albumin) and the fluorescence intensity of the reaction was immediately determined at 488 nm excitation (slit 2.5) and 530 nm emission (slit 5.0) at room temperature using a luminescence spectrometer LS50B (Perkin-Elmer Instruments, Norwalk, Conn.). An initial reading was recorded as zero time and subsequent readings were taken every 5-10 sec for 2-4 min. The activity was expressed as fluorescence intensity (FI) vs. time (sec) after initial reading was subtracted.

Isolating and characterizing factors in human serum that affect $PLA_2$ activity. To determine the factor(s) in the serum that may affect the $PLA_2$ activity, a total of 7 ml of human sera from four healthy volunteers was used for a series of column chromatography isolation. The activity of the factor(s) that affects $PLA_2$ reaction was determined using the single cuvette method with DOPC-PG-BODIPY-PC as the substrate. The serum was first applied to a Sephadex G100 (Pharmacia, Piscataway, N.J.) column (2.6×55 cm) equilibrated with Tris-EDTA-NaCl buffer (0.01 M Tris-HCl, 5 mM 2-mercaptoethanol, 1 mM EDTA and 0.15 M NaCl, 0.02% $NaN_3$, pH 7.4). The proteins were eluted with the Tris-EDTA-NaCl buffer at a flow rate of 12 ml per hour and collected in 2 ml per tube. Protein in each fraction was detected by absorbance at 280 nm. An aliquot of 40 µl or 150 µl of each fraction collected from the column was added to the $PLA_2$ reaction mixture to determine the unknown factor activity. Fractions that had FI inhibitory effect in the presence of $PLA_2$ were pooled, equilibrated with 0.01M Tris-HCl, pH 7.4, and concentrated to about 1 ml. The concentrated pool was applied to a high performance liquid chromatography (HPLC) anionic exchange MonoQ column (5×50 mm) (Pharmacia) pre-equilibrated with 0.01 M Tris-HCl buffer, pH 7.4. The column was eluted with 0.01 M Tris buffer with an ascending gradient of 1M NaCl in Tris buffer. The column was first eluted for 10 min with 0.01 M Tris buffer, then with 25% of 1 M NaCl for 100 min, 50% of 1M NaCl for 30 min, and finally with 100% of 1 M NaCl for 10 min. The flow rate was 1 ml/min and the collected fraction volume was 1 ml per fraction tube. Protein in each fraction was determined by absorbance at 280 nm and its effect on $PLA_2$ activity was determined.

The fractions from HPLC MonoQ column chromatography that affected the $PLA_2$ activity were pooled, concentrated and applied to a reverse phase HPLC Vydac C4 column (4.6×250 mm) (Separations Groups, Hesperia, Calif.). The column was eluted with a gradient of solvent A (0.1% trifluoroacetic acid, TFA) and solvent B (90% acetonitrile in 0.088% TFA) at a flow rate of 1 ml/min. The elution program was setup as: 0-10 min 0% B, 10-25 min 0-30% B, 25-65 min 30-70% B, 65-80 min 70-100% B. Protein in each fraction was determined by absorbance at 215 mm and 280 nm and its effect on the $PLA_2$ activity was determined.

The purity of the protein was analyzed by sodium dodecyl sulfate polyacrylamide gel electrophoresis (SDS-PAGE) using 10% SDS Ready gel and Mini-PROTEAN 3 Cell Assembly Unit (Bio-Rad, Hercules, Calif.) under denaturing conditions. Proteins on the SDS gel were visualized by Coomassie brilliant blue staining.

Peptide sequence determination of serum protein that affects PLA2 activity. An amount of 5 μg of the purified serum protein that affected the $PLA_2$ activity was run by SDS-PAGE. The Coomassie brilliant blue stained protein band on SDS gel was excised and placed into a 0.5 ml microcentrifuge tube. The gel was treated in 100 μl of 25 mM $NH_4HCO_3$/50% acetonitrile to remove the Coomassie blue stain. The decolored gel was dried in vacuum centrifuge. The protein was reduced in 100 mM dithiothreitol followed by modification with 55 mM iodoacetamide. Then the protein was digested with trypsin (20 μl of 0.006 mg/ml) at 37° C. for 24 hr. The peptides were collected by washing the gel with water followed by washing with 5% trifluoroacetic acid and 50% acetonitrile. The washes were combined and dried in vacuum centrifuge. The dried peptides were used for mass and peptide sequence determination using the methods of "matrix-assisted laser desorption ionization" (MALDI) and tandem mass spectrometry (MS/MS) method using the TOF instruments conducted at the University of Wisconsin Biotechnology Center (UWBC) on campus.

Effects of plasma and serum on $PLA_2$ activity. The effects of plasma or serum on $PLA_2$ activity were investigated by using plasma or serum from healthy subjects (HS) and pancreatic $sPLA_2$ as the enzyme source. In the reaction mixture in a cuvette containing liposomes (50% DOPC-50% PG labeled with BODIPY-PC) as the substrates, pancreatic $sPLA_2$ generated a time-dependent increase in fluorescence intensity (ΔFI) (FIG. 49). Without $sPLA_2$, the levels of ΔFI remained no significant change during the 2-min reaction. Presence of 1.75 μl of plasma or serum in the reaction mixture markedly increased ΔFI in the $sPLA_2$ reaction. However, an increase in plasma or serum, for example, to 5 μl in the $PLA_2$ reaction mixture, ΔFI started to decrease to the level below the baseline in the first 30 sec and then gradually increased afterward to the baseline level. Increasing the amount of plasma or serum to 10 μl reduced ΔFI farther from the baseline level and yielded negative ΔFI values through the 2-min reaction. Increasing the plasma or serum to 20 μl had a similar effect as 10 μl of plasma or serum. In the absence of $sPLA_2$ but presence of calcium, or absence of calcium but presence of $sPLA_2$, plasma or serum at 1.75 μl or 10 μl had no effect on FI. The effects of plasma or serum on the $sPLA_2$ reaction remained no change after plasma or serum was set on ice for more than 5 h or stored at −70° C. for more than a month. The effects of serum from subjects with COPD were tested. COPD subject's serum at 1.75 μl had similar stimulating effect on ΔFI in the $PLA_2$ reaction as that from healthy subject. However, presence of 10 μl of serum from COPD subject only decreased ΔFI in the $PLA_2$ reaction to the level as that affected by 5 μl healthy subject's serum (FIG. 49).

The effects of 1.75 μl (for $PLA_2$-s) and 10 μl (for SFA) of plasma were determined from multiple plasma samples from several HS, COPD, and patients with cystic fibrosis (CF). Total fluorescence intensity (TFI) was obtained by adding up of all recorded ΔFI within 2 min of the reaction time. The results of TFI and albumin level of the assayed plasma samples are summarized in Table 8.

TABLE 8

Total Fluorescence Intensity (TFI) of SFA, $PLA_2$-s, and albumin content in plasma.

| Subjects | TFI of SFA | TFI of $PLA_2$-s | Albumin (g/dL) |
|---|---|---|---|
| HS | −56.66 ± 1.15 (8) | 62.21 ± 2.45 (8) | 3.94 ± 0.09 (8) |
| CF | −29.28 ± 5.64 (5) | 61.97 ± 5.40 (5) | 3.66 ± 0.14 (5) |
| COPD | −17.10 ± 1.92 (3) | 56.01 ± 10.80 (3) | 2.90 ± 0.31 (3) |

The data is presented as mean ± SEM. TFI is the sum of ΔPI recorded within 2 min of reaction time. Plasma samples were obtained from HS (healthy subjects), CF (cystic fibrosis subjects) and COPD (chronic obstructive pulmonary disease subjects). The number of subjects is shown in the parenthesis. Each sample was assayed in duplicate.
*$p < 0.05$ (t-test) compared to HS.
The value of TFI of PLA2 without plasma was 23.37 ± 4.77 for 29 assays.

There were no significant differences among the values of $PLA_2$-s TFI of the plasma samples of HS, CF, and COPD. However, the values of $PLA_2$-i TFI of CF and COPD were only 52% and 30% of that of HS, respectively. The amounts of albumin in the CF and COPD samples were 93% and 74% of that of HS, respectively. The marked difference in $PLA_2$-i TFI between HS and CF and COPD prompted us to determine the $PLA_2$-i factor in the plasma or serum.

Isolation, characterization, and determination of the factor(s) in the human serum that affect ΔFI in $sPLA_2$ reaction. Because plasma and serum had the same effects on $PLA_2$ activity, a pool of 5 ml of serum from healthy subjects was used as the source for isolation of the $PLA_2$-i factor. After serum was applied to a Sephadex G100 column, the factors that increased or decreased ΔFI in the $PLA_2$ assay were in the fractions containing proteins in the range of molecular weights between 10-70 kDa (data not shown). After the Sephadex G100 column fractions that affected ΔFI were pooled, processed, and applied to an anionic exchange MonoQ column, fractions collected between 60 and 90 min contained factors that increased percentage of total ΔFI of $sPLA_2$ (100% assigned for $sPLA_2$ activity) (FIG. 50A). However, fractions that decreased percentage of total $sPLA_2$ activity was mainly in the fractions collected between 65 and 75 min (eluted between 0.07 M and 0.17 M NaCl gradient). After the fractions eluted between 65 and 75 min from MonoQ column were further purified by the HPLC reverse phase Vydac C4 column, two major protein peaks were obtained (FIG. 50B). Only the protein fraction marked Protein-I contained the stimulating and inhibitory effects on ΔFI in the $sPLA_2$ assay. SDS gel analysis showed that Protein-I was highly homogenous with an apparent molecular weight of 62 kDa (FIG. 50B).

The fractions of Protein-I were pooled and equilibrated in 0.01 M Tris-HCl buffer, pH 7.4 to eliminate the organic solvent used for the reverse phase column chromatography, and its effect on ΔFI in $sPLA_2$ assay was determined. Protein-I exhibited similar effects on ΔFI in the $sPLA_2$ assay as that observed with serum or plasma (FIG. 51). At low protein level (e.g., less than 30 μg), Protein-I increased ΔFI, at high protein level (e.g., 256 μg), Protein-I produced negative ΔFI below the baseline. After treating Protein-I in boiling water for 5 min, Protein-I lost all of its ΔFI increasing and decreasing effects in the $sPLA_2$ assay. Protein-I itself had no effect on the FI in the assay.

All determined peptide sequences of trypsin-digested Protein-I (Upper Case) were identical to the matched human albumin peptide sequences (GenBank/NCBI, accession No. AAA98797) shown in the numeric numbers: YLYEIAR (162-168), QTALVELVK (550-558), LVNEVTEFAK (66-75), AVMDDFAAFVEK (570-581), KVPQVSTPTLVEVS (438-451), RPCFSALEVDETYV (509-522), VFDEFK-PLVEEPQN (397-410). The results of the peptide sequences and the apparent molecular weight shown in FIG. 52B of Protein-I confirmed that Protein-I was albumin. The inventors then tested the effects of commercially available albumin products, globulin-free albumin and fatty acid-free albumin on ΔFI in the $sPLA_2$ assay. Presence of globulin-free or fatty acid-free albumin in low amount (0.08 mg) in the $sPLA_2$ reaction mixture increased ΔFI (FIGS. 52A and 52B), similar to that observed in reactions containing plasma, serum, or Protein-I. With increasing amounts of albumin to 0.32 mg in the reaction mixture, the fatty acid-free albumin reduced ΔFI in the first 60 sec to the level below the baseline, and then gradually increased ΔFI to above the baseline level (FIG. 52A). With increasing the amount of fatty acid-free albumin to 0.64 mg in the $sPLA_2$ reaction, ΔFI was reduced far below the baseline during the 2-min reaction (FIG. 52A).

In contrast, globulin-free albumin at 0.32 mg to 0.64 mg had much less inhibitory effect on ΔFI in the $PLA_2$ reaction (FIG. 52B). Although fatty acid-free albumin and globulin-free albumin showed a single protein band on the SDS gel, both proteins yielded multiple protein fractions after each protein was passed through the anionic MonoQ column; the patterns of column chromatograms of both proteins were similar (FIGS. 52C and 52D). Some fractions from fatty acid-free albumin and globulin-free albumin had similar ΔFI-increasing effects when certain amounts of the protein in these fractions were added to the $sPLA_2$ assay (FIGS. 52C and 52D blue).

Under the $sPLA_2$ assay conditions that determine the ΔFI-decreasing effect with large amounts of protein, only a small fraction of protein eluted between 87 and 92 min from the column loaded with fatty acid-free albumin had the ΔFI-decreasing effect. The amount of protein in these fractions was only about 5% of total albumin recovered from the MonoQ column. This fraction of albumin is known throughout this document as the "Specific Fraction of Albumin" (SFA). Unlike fatty acid-free albumin, none of the protein fractions of globulin-free albumin collected from MonoQ column had significant ΔFI-decreasing effect under the same assay conditions (FIGS. 52C and 52D red).

To test whether or not globulin-free albumin's lack of ΔFI-decreasing effect in the $PLA_2$ assay was due to contamination in the globulin-free albumin that might inhibit the ΔFI-decreasing effect, the inventors added 0.64 mg of globulin-free albumin and 0.64 mg fatty acid-free albumin to the $PLA_2$ reaction mixture. There was no difference in TFI between the reaction containing (globulin-free albumin+fatty acid-free albumin) and the reaction containing fatty acid-free albumin (−97.15±7.0 vs.-91.87±2.03 from 2 assays, respectively). Similar to the pancreatic $PLA_2$ assay, serum and fatty acid-free albumin also had ΔFI-increasing and ΔFI-decreasing effects on the recombinant human $sPLA_2$-IIA activity in the fluorescent assay with BODIPY-PC labeled liposomes (FIG. 53). Therefore, there is no significant difference in regards to determination of the effects of serum or albumin on the activities between $sPLA_2$-IIA and pancreatic $sPLA_2$ by the in vitro fluorescent assay.

Determining $sPLA_2$-induced albumin-liposome interaction using BODIPY-FA-labeled liposomes as substrates. BODIPY-PC used in liposomes was the substrate of $sPLA_2$ which generated fluorescently labeled fatty acid and lysoPC. Clearly, albumin effects on ΔFI-increasing and ΔFI-decreasing signals in the $sPLA_2$ assay with BODIPY-PC liposomes as substrates probably involved interactions of albumin with three fluorescently labeled components, PC, fatty acid, and lysoPC. Thus, mixed fluorescent signals from the $sPLA_2$ reaction and albumin-liposome interaction were produced. To eliminate the FI change that could be generated by $sPLA_2$, the inventors used fluorescent probe-labeled FA (BODIPY-FA) to replace the BODIPY-PC in liposomes so the fluorescent probe was no longer the $sPLA_2$ substrate.

With BODIPY-FA-labeled liposomes as substrates, the inventors observed that $sPLA_2$ did not produce significant ΔFI in the assay mixture conducted in a single cuvette (FIG. 54A). Without $sPLA_2$, presence of plasma, serum in the assay mixture containing BODIPY-FA liposomes did not produce significant changes in ΔFI. However, combining plasma (serum or albumin) and $sPLA_2$ in the reaction mixture generated a time-dependent increase in ΔFI; there was no significant difference in ΔFI produced by plasma or serum. However, the presence of fatty-acid free albumin in the $sPLA_2$ reaction mixture increased ΔFI much higher than that generated by the same amount of globulin-free albumin (FIG. 54A). The BODIPY-FA-labeled liposome assay could be easily performed in 96-well microplate, similar to the $sPLA_2$ assay previously described (33).

Three different kinds of liposomes labeled with BODIPY-FA were used as substrates to test the $sPLA_2$-induced serum-liposome interactions. Liposomes made of 50% DOPC-50% PG yielded the highest ΔFI values in the reaction mixture (214.81±7.02, n=3), next was liposomes made of 100% PG (170.96±4.20, n=3); liposomes made of 100% PC did not yield any FI change in the reaction (−2.74±0.53, n=3). Similar results were obtained by using 10 μl BODIPY-FA-labeled DOPC-PG mixture prepared in 100% ethanol as substrate in microplate assay (data not shown). This substrate preparation further simplifies the assay procedure by omitting sonication. Substrates in ethanol were stable at −20° C. for at least over 6 months.

The inventors next examined the effects of serum from healthy individuals, subjects with COPD or sepsis on $sPLA_2$-induced albumin-BODIPY-FA-liposome interactions. The assay was conducted in 96-well microplate under two different conditions: assay 1 was performed in the absence of exogenous $sPLA_2$, and assay 2 was carried out in the presence of exogenous pancreatic $PLA_2$. In the absence of exogenous PLA2 in the assay reaction, only the serum from septic patients yielded significant amounts of ΔFI, whereas serum from healthy and COPD subjects did not produce any ΔFI (FIG. 54B). In the presence of exogenous $PLA_2$, the ΔFI values generated by the serum from healthy subjects were nearly 2× higher than that generated by the serum from COPD or septic patients (FIG. 54C). Subtraction of the ΔFI values in FIG. 54B (Serum−Exogenous $PLA_2$ assay) from the ΔFI values in FIG. 54B (serum+exogenous $PLA_2$ assay) yielded the serum-liposome interaction values among the three groups of subjects more strikingly different (FIG. 54D). The average value (termed as SFA activity in unit of ΔFI/min/μl serum) in the serum from 7 healthy individuals, 3 COPD subjects, and 3 septic patients were 198.7±4.1, 93.0+14.1, and 26.5±7.3, respectively.

SFA activity was dependent on the phospholipid composition in the substrate. Negatively charged phospholipid (PG) in substrate was required for determining the serum SFA activity (FIG. 55). SFA was completely inactive with using 100% DOPC as substrate. A combination of 50% DOPC and 50% PG was better substrate than 100% PG substrate.

Determining $sPLA_2$ activity by the continuous fluorescent assay is based on the measurement of FI change due to the cleavage of the fatty acyl group at the 2-position of fluorescent probe BODIPY-PC embedded in liposomes by $sPLA_2$ (26). The presence of plasma or serum in the assay mixture in absence of $sPLA_2$ did not have any effect on FI as compared to the background. However, co-presence of $sPLA_2$ and plasma or serum, FI changed in addition to that generated by $sPLA_2$. For example, addition of a small amount of plasma or serum (e.g., 1.7 μl in 3 ml reaction volume) into the $sPLA_2$ assay mixture markedly increased the change of FI (ΔFI). Moderate increase in plasma or serum (e.g., 5 μl) did not increase ΔFI proportionally, rather, a biphasic characteristic effect was observed; ΔFI decreased to yield negative value in the beginning of the reaction and then gradually increased to the positive level with increasing reaction time.

In the presence of more than 10 μl of plasma or serum in the 3 ml $sPLA_2$ assay mixture, FI rapidly decreased and negative ΔFI values were obtained during the period of assay. Plasma and serum had the same effects. The additional FI changes could be due to fluorescence perturbation of the substrate or products by plasma or serum, or due to the effects on the $sPLA_2$ activity. Analysis of the components in the serum showed that albumin was the only constituent that increased or decreased FI in the $sPLA_2$ reaction. No other serum proteins had these dual effects in the $sPLA_2$ assay.

It has long been demonstrated that some proteins including albumin affect $PLA_2$ activity in vitro. By keeping liposome substrate concentration constant but varying the amounts of human plasma, serum, or albumin, this study showed similar results; low amounts of plasma, serum, or albumin increased FI and high amount decreased FI. Increase in FI could be due to removal of $sPLA_2$ products by albumin that might result in $sPLA_2$ activity increase, and also could enhance the fluorescence signal due to removal of fluorescent products from substrate membranes. Decrease in FI to the level lower than the baseline initial FI reading by high content of plasma, serum, or albumin suggests the possibility that albumin might shield the emission of substrate liposome fluorescent energy. Such phenomenon may be similar to the mechanism of substrate depletion enforced by albumin in the $PLA_2$ reaction, as previously suggested (32).

However, most previous studies were conducted with using radiometric assay which determines the end products. The radiometric assay cannot determine albumin-substrate dynamic interaction during the assay. The continuous fluorescent assay could determine the dynamical albumin-substrate interaction.

Previous studies showed that albumin alone could interact with model membranes (50). However, the inventors' study showed that a wide range of the amounts of albumin had little effect on the liposome fluorescence intensity. Only when $PLA_2$ was added to the albumin and liposome mixture, was the fluorescence intensity markedly reduced in a time-dependent and albumin dose-dependent manner. The decrease in the fluorescence intensity was likely due to the interaction between albumin and liposomes induced by $PLA_2$. Under such conditions, albumin not only binds or aggregates liposomes, it may also block the $PLA_2$ action on the membrane. The $PLA_2$-induced albumin-membrane interaction was not previously reported. Under the assay conditions without $sPLA_2$, a wide range of amounts of plasma, serum, and albumin had insignificant effect on liposome FI, suggesting a lack of albumin-liposome interaction in the absence of $sPLA_2$. Other proteins such as annexins also bind and aggregate vesicles in a calcium-dependent manner and inhibit $PLA_2$ (51, 1). However, annexin alone binds and aggregates liposomes and the annexin-membrane binding does not require $PLA_2$ (51, 1). The requirement of large amounts of albumin to decrease the liposome fluorescence intensity suggests that albumin may interact with liposomes on the bilayer membrane surface and thus inhibit $PLA_2$ action and prevent the fluorescence emission from liposomes. This albumin property may have a role in cellular protection against the action of secretory $PLA_2$.

In this study, the inventors observed similar multiple fractions from fatty acid-free and globulin-free albumin passed through the MonoQ Column (FIG. 52C-D). The fluorescent assay showed that not all heterogeneous forms of albumin interact with liposomes in the same way in response to $sPLA_2$ actions. At low albumin concentrations, most fractions of fatty acid-free albumin and globulin-free albumin increased ΔFI similarly. However, at high albumin concentrations, only a small fatty acid-free albumin fraction that was about 5% of total albumin (named specific fraction of albumin or SFA) had the activity to produce negative ΔFI in response to $sPLA_2$. The SFA activity was largely deficient in the globulin-free albumin fractions. The SFA is part of the SFA fraction which has the lowest fatty acid content among other forms of albumin (18). It is not clear why the commercial globulin-free albumin product was SFA deficient whereas human serum samples the inventors assayed had the SFA activity.

As described in the commercial products, fatty acid-free albumin was produced from globulin-free albumin by removal of fatty acids. Apparently, removal of fatty acids from globulin-free albumin restored the SFA activity. This suggests that fatty acid bound to SFA could deplete the capability of SFA to interact with liposomes in response to the $sPLA_2$ reaction. It is noted that proteins of commercial albumins were eluted about 20 min earlier than proteins from serum from MonoQ column (FIG. 52C-D vs. FIG. 50A). This is probably due to variable column conditions or to the presence of other proteins in the serum that might affect the protein retention time in the column. Nevertheless, the fractions that had SFA activity were relatively in the same locations in the major fatty acid-free SFA protein peak in the chromatograms of the commercial product of fatty acid-free albumin and the human serum.

The FI values generated from $sPLA_2$-albumin (plasma or serum) assay using BODIPY-PC labeled liposomes as substrates were combinations of the FI values from $sPLA_2$ reaction and albumin-liposome interaction. To eliminate $sPLA_2$-produced FI signals, BODIPY-FA labeled liposomes were used as substrates because FA is a $sPLA_2$ reaction product. Based on the nature of BODIPY-FA, the probe is quenched when it is incorporated into liposome membranes. FI increases while BODIPY-FA is removed from liposome membranes. Therefore, if albumin interacts with liposomes, binds and removes BODIPY-FA from liposomes, the inventors would expect an increase in FI.

As a result, addition of albumin (plasma or serum) to the $sPLA_2$ reaction mixture yielded a time-dependent increase in FI, whereas $sPLA_2$ alone did not generate any change in FI. Without $sPLA_2$, plasma, serum, or albumin alone did not change FI. This again demonstrates that $sPLA_2$ induces albumin interacting with liposomes, and the interaction further drives albumin to bind and remove BODIPY-FA embedded in liposomes, thus results in FI increase. In this assay only positive ΔFI values were obtained, despite the amount of albumin present in the assay. Similar to the $sPLA_2$ reaction, calcium is also required for the $sPLA_2$-induced albumin-liposome interactions, and incorporation of negatively charged PG in liposomes greatly enhanced the $sPLA_2$-induced albumin-liposome interactions.

Without liposome membranes, BODIPY-FA alone could not serve as substrate. It is interesting to note that substrate of BODIPY-FA and DOPC-PG prepared in ethanol produced similar results as substrate liposomes prepared in buffer. Although phospholipids dissolved in ethanol are single molecules, they form liposomes spontaneously once phospholipid ethanol solution is added to the buffer (52, 53). Albumin-liposome interaction or albumin-FA binding requires the presence of calcium, negatively charged liposomes, and $sPLA_2$.

To determine the SFA activity in the serum with using BODIPY-FA liposome as substrate, two assays were carried out for each serum sample: assay one was conduced with addition of exogenous $sPLA_2$ into the assay mixture; assay two was conducted in absence of exogenous $sPLA_2$. The levels of exogenous $sPLA_2$-induced albumin-liposome interactions in the serum from healthy individuals were 40-60% higher than that in the serum from subjects with COPD and sepsis. In the absence of exogenous $sPLA_2$, serum from healthy and COPD subjects did not produce any significant change in FI. However, serum from septic patients had marked high levels of FI increase in the absence of exogenous $sPLA_2$, presumably produced by the endogenous $sPLA_2$-induced albumin-liposome interactions. As previously reported, serum from septic patients contained high levels of endogenous $sPLA_2$ activity (33). Subtracting endogenous $sPLA_2$-induced albumin-liposome interaction level from exogenous $sPLA_2$-induced SFA-liposome level (namely $sPLA_2$-SFA activity) revealed that the $sPLA_2$-SFA activity in the serum from COPD and septic patients was about 50% and 80% lower than that from healthy subjects, respectively (FIG. 54D). In part, deficiency in sPLA2-SFA activity in patients' serum is probably due to lower quantity of serum albumin. Because total serum albumin of COPD (Table 8) and septic patients (3.1+0.7 for 3 septic patients) were only about 20-30% lower than healthy subjects, the inventors speculate that SFA in COPD and sepsis patients' serum was deficient.

The $sPLA_2$-SFA-liposome interaction assay of the present invention shows that $sPLA_2$ triggers albumin to interact with liposomes to bind fatty acids. The assay sensitively determines the binding activity changes in albumin under pathophysiological conditions. It is not clear whether the lack of SFA activity in the serum from subjects with systemic inflammation is due to protein deficiency or to the modification of SFA fatty acid binding sites. Nevertheless, the $sPLA_2$-SFA-liposome assay of the present invention provides a sensitive, simple method to determine the serum albumin activity including transporting fatty acids and possibly other metabolites and drugs.

The present invention is not intended to be limited to the foregoing examples, but encompasses all such modifications and variations as come within the scope of the appended claims. It should be noted that the above description, attached figures and their descriptions are intended to be illustrative and not limiting of this invention. Many themes and variations of this invention will be suggested to one skilled in this art and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Griffiths R J. Prostaglandins and inflammation. In Inflammation: Basic Principles and Clinical Correlates, 3rd ed., J. I. Gallin and R. Snyderman, editors. Lippincott Williams & Wilkins, Philadelphia. 1999; 349-360.
2. Murakami M et al J Biochem 2002; 131:285-292.
3. Balsinde J et al. Annu Rev Pharmacol Toxicol 1999; 39:175-189.
4. Valentin E et al. Biochim Biophys Acta 2000; 1488:59-70.
5. Vadas P, Pruzanski W. Phospholipase A2 activation is the pivotal step in the effector pathway of inflammation. In: Phospholipase A2, ed. By Wong P Y K, Dennis E A. Plenum Press, New York 1990; p. 83-101.
6. Lai C Y et al. Biochem Biophys Res Comm 1988; 167:488-493.
7. Kramer R M et al. J Biol Chem 1989; 264:5768-5775.
8. Seilhamer J J et al. J Biol Chem 1989; 264:5335-5338.
9. Nevalainen T J et al. Biochim Biophys Acta 2000; 1488: 83-90.
10. Buckland A G et al. Biochim Biophys Acta 2000; 1488: 71-82.
11. Funk C D. Science 2001; 294:1871-1875
12. Yedgar S et al. Biochim Biophys Acta 2000; 1488:182-187.
13. Kim, T. S. et al. J. Biol. Chem. 272:2542-2550.
14. Meshulam et al. J. Biol. Chem. 267:21465-21470.
15. Conricode K M et al. Biochim Biophys Acta 1989; 1003: 36-43.
16. Carter D C et al. Adv Protein Chem 1994; 45:152-203.
17. Curry S et al. Biochim Biophys Acta 1999; 1441:131-140.
18. Noel et al. J Biol Chem 1972; 247:7391-7406.
19. Ascoli G A et al. Chirality 18; 9:667-679
20. Doweiko J P et al. Parenter Entemal Nutr 1991; 15:212-214.
21. Doumas et al. Clin Chim Acta 1971; 31:87-96.
22. Parviainen M T et al. Scand J Clin Lab Invest 1985; 45:561-564.
23. Penrose J F., Austen K F, Lam B K. Leukotrienes: Biosynthetic pathways. Release, and receptor-mediated actions with relevance to disease states. In Inflammation: Basic Principles and Clinical Correlates, 3rd ed., J. I. Gallin and R. Snyderman, editors. Lippincott Williams & Wilkins, Philadelphia. 1999; 361-372.
24. Davis P B et al. Am J Respir Crit. Care Med 1996; 154:1229-1256.
25. Barton A D et al. J Lab Clin Med. 1976; 88:423-426.
26. Bruce M C et al. Am Rev Respir Dis. 1985; 132:529-535.
27. Gilljam H et al. Scan J Clin Lab Invest 1986; 46:511-518.
28. Miele L et al. DNA Cell Biol 1997; 16:749-759.
29. Freedman S D et al. Proc Natl Acad Sci USA 1999; 96:13995-14000.
30. Tsao F H C. 2001; U.S. Pat. No. 6,180,596.
31. Martin G S et al. N Engl J. Med. 2003, 348:1546-1554
32. Conricode K M et al. Biochim Biophys Acta 1989; 1003: 36-43.
33. Tsao F H C et al. Clin Chim Acta 2007; 379:119-126.
34. Ruggiero V et al. Mediators of inflammation 1993; 2:S43-S50.
35. Blanque R et al. General pharmacology 1998; 31:301-306.
36. Endo Y et al. Brit J Pharmacol 1999; 128:5-12.
37. Dinges M M et al. Infect Immun 2001; 7169-7172.
38. Ostberg J R et al. J Leukoc Biol 2000; 68:815-820.
39. Pappas P et al. Chem-Biologic Interact 2003; 143-144: 55-62.
40. Sears B. The Anti-Inflammation Zone. Regan Books, HarperCollins Publishers. 2005
41. Tsao F H C et al. Am J Respir Cell Mol Biol 1998; 18:120-128.
42. Tsao F H C. Biochim Biophys Acta 1990; 1045:29-39

43. Tsao et al Biochim. Biophys. Acta 1991; 1081:141-150.

44. Heinrikson R L, Kezdy F J. A novel bifunctional mechanism of surface recognition by phospholipase $A_2$. In “Biochemistry, Molecular Biology, and Physiology of Phospholipase A2 and Its Regulatory Factors”, ed. Mukheijee A B. Plenum Press, New York, 1990; p. 37-4

45. Cantin A et al. Pediatr Pulmon 1989; 7:12-17.

46. Bligh E G, et al. Can J Biochem Physiol 1955; 37:911-917.

47. Moraga F et al. Arch. Biochem. Biophys. 2001; 221-226.

48. Banda M J et al. J. Biol. Chem. 1988; 263: 4481-4484.

49. Vissers M C et al. J. Clin. Invest. 1988; 82:706-711.

50. Galantai R et al. Internat J Pharmaceu 2000; 195:207-218

51. Semple et al. Biochim Biophys Acta 2001; 1510:152-166.

52. Maurer N et al. Biophysic J 2001; 80:2310-2326.

We claim:

1. A method for measuring the activity of a specific fraction of albumin (SFA) in a mammalian subject, the method comprising the steps of:

providing a substrate comprising a fluorescently-labeled carboxylic acid and a negatively-charged phospholipid in an organic solvent;

mixing the substrate with phospholipase $A_2$ in a biological test sample from the subject;

measuring a change in fluorescence intensity to determine the SFA activity in the test sample; and comparing the SFA activity in the test sample to SFA activity in a control sample, wherein a decrease in SFA activity of the test sample as compared to the SFA activity of the control sample indicates that the subject has developed or is about to develop inflammation.

2. The method of claim 1, wherein the organic solvent is alcohol.

3. The method of claim 2, wherein the alcohol is ethanol.

4. The method of claim 1, wherein the subject is human.

5. The method of claim 1, wherein the biological sample is selected from plasma, serum, bronchoalveolar lavage fluid, white blood cells, alveolar macrophages, synovial fluid, sputum, urine, amniotic fluid, peritoneal fluid, cerebrospinal fluid, pleural fluid, and pericardial fluid.

6. The method of claim 1, wherein the fluorescence intensity is measured at defined intervals over a specific period of time.

7. The method of claim 1, wherein the negatively-charged phospholipid is selected from phosphatidylglycerol (PG), phosphatidylcholine (PC), phosphatidylserine (PS), phosphatidylinositol (PI), phosphatidic acid (PA), a PG/PC mixture, and combinations thereof.

8. The method of claim 7, wherein the negatively-charged phospholipid is phosphatidylglycerol (PG).

9. The method of claim 1, wherein the carboxylic acid is a fatty acid.

10. The method of claim 9, wherein the fatty acid has a hydrocarbon chain length from about 6 to 18 carbons.

11. The method of claim 10, wherein the fluorescently-labeled fatty acid is 4,4-difluoro-5-methyl-4-bora-3a,4a-diaza-s-indacene-3-dodecanoic acid (BODIPY-FA).

12. The method of claim 1, wherein the substrate comprises 4,4-difluoro-5-methyl-4-bora -3a,4a-diaza-s-indacene-3-dodecanoic acid (BODIPY-FA), phosphatidylglycerol (PG), and dioleoyl PC.

13. The method of claim 1, wherein a decrease in the SFA activity of the test sample as compared to the SFA activity of the control sample indicates that the subject has developed or is about to develop chronic obstructive pulmonary disease (COPD), cystic fibrosis (CF) or sepsis.

14. A method for measuring the activity of a secretory phospholipase ($sPLA_2$) in a mammalian subject, the method comprising the steps of:

providing a substrate comprising a fluorescently-labeled phospholipid and a negatively-charged phospholipid in an organic solvent;

mixing the substrate with phospholipase $A_2$ in a biological test sample from the subject;

measuring a change in fluorescence intensity to determine the $sPLA_2$ activity in the test sample; and comparing the $sPLA_2$ activity in the test sample to $sPLA_2$ activity in a control sample, wherein an increase in the $sPLA_2$ activity of the test sample as compared to the $sPLA_2$ activity of the control sample indicates that the subject has developed or is about to develop inflammation.

15. The method of claim 14, wherein the organic solvent is alcohol.

16. The method of claim 15, wherein the alcohol is ethanol.

17. The method of claim 14, wherein the subject is human.

18. The method of claim 14, wherein an increase in the $sPLA_2$ activity of the test sample as compared to the $sPLA_2$ activity of the control sample indicates that the subject has developed or is about to develop chronic obstructive pulmonary disease (COPD), cystic fibrosis (CF) or sepsis.

19. The method of claim 14, wherein the substrate comprises 1,2-bis-(4,4-difluoro-5,7-dimethyl-4-bora-3a,4a-diaza-s-indacene-3-undecanoyl)-sn-glycero-3-phosphocholine (BODIPY-PC) and dioleoyl PC.

20. A kit for measuring the activity of a specific fraction of albumin (SFA), the kit comprising:

a fluorescently-labeled carboxylic acid;

a mixture of neutral and negatively-charged phospholipid;

phospholipase $A_2$;

a positive control comprising SFA from a healthy subject; and instructions for use.

* * * * *

SEQUENCE LISTING

```
<160> NUMBER OF SEQ ID NOS: 23

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asp Lys Ile Thr Pro Asp Leu Ala Glu
            20                  25                  30

Phe Ala Phe Ser Leu Tyr Arg Gln Leu Ala His Gln Ser Asp Ser Thr
        35                  40                  45

Asn Ile Phe Phe Ser Pro Val Ser Ile Ala Ala Ala Phe Ala Met Leu
    50                  55                  60

Ser Leu Gly Ala Lys Gly Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Phe Leu Lys Leu Phe Asp
        115                 120                 125

Lys Phe Leu Glu Asp Phe Lys Lys Leu Tyr His Ser Glu Ala Phe Thr
    130                 135                 140

Val Asn Phe Gly Thr Asp Glu Glu Ala Lys Lys Gln Ile Asn Asp Tyr
145                 150                 155                 160

Val Glu Lys Gly Thr Gln Gly Lys Ile Val Asn Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300
```

```
Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390


<210> SEQ ID NO 2
<211> LENGTH: 6
<212> TYPE: PRT
<213> ORGANISM: Homo sapiens

<400> SEQUENCE: 2

Ile Val Asp Leu Val Lys
1               5


<210> SEQ ID NO 3
<211> LENGTH: 9
<212> TYPE: PRT
<213> ORGANISM: Homo sapiens

<400> SEQUENCE: 3

Leu Ser Ser Trp Val Leu Leu Met Lys
1               5


<210> SEQ ID NO 4
<211> LENGTH: 10
<212> TYPE: PRT
<213> ORGANISM: Homo sapiens

<400> SEQUENCE: 4

Leu Ser Ile Thr Gly Thr Tyr Leu Asp Lys
1               5                   10


<210> SEQ ID NO 5
<211> LENGTH: 14
<212> TYPE: PRT
<213> ORGANISM: Homo sapiens

<400> SEQUENCE: 5

Gly Thr Glu Ala Ala Gly Ala Met Phe Leu Glu Ala Ala Pro
1               5                   10


<210> SEQ ID NO 6
<211> LENGTH: 14
<212> TYPE: PRT
<213> ORGANISM: Homo sapiens

<400> SEQUENCE: 6

Ile Thr Pro Asn Leu Ala Glu Phe Ala Phe Ser Leu Tyr Arg
1               5                   10


<210> SEQ ID NO 7
<211> LENGTH: 14
<212> TYPE: PRT
<213> ORGANISM: Homo sapiens

<400> SEQUENCE: 7
```

```
Val Phe Ser Asn Gly Ala Asp Leu Ser Gly Val Thr Glu Glu
1               5                   10


<210> SEQ ID NO 8
<211> LENGTH: 14
<212> TYPE: PRT
<213> ORGANISM: Homo sapiens

<400> SEQUENCE: 8

Thr Leu Asn Gln Pro Asp Ser Gln Leu Gln Leu Thr Thr Gly
1               5                   10


<210> SEQ ID NO 9
<211> LENGTH: 4
<212> TYPE: PRT
<213> ORGANISM: Homo sapiens

<400> SEQUENCE: 9

Phe Gly Glu Arg
1


<210> SEQ ID NO 10
<211> LENGTH: 7
<212> TYPE: PRT
<213> ORGANISM: Homo sapiens

<400> SEQUENCE: 10

Tyr Leu Tyr Glu Ile Ala Arg
1               5


<210> SEQ ID NO 11
<211> LENGTH: 9
<212> TYPE: PRT
<213> ORGANISM: Homo sapiens

<400> SEQUENCE: 11

Gln Thr Ala Leu Val Glu Leu Val Lys
1               5


<210> SEQ ID NO 12
<211> LENGTH: 12
<212> TYPE: PRT
<213> ORGANISM: Homo sapiens

<400> SEQUENCE: 12

Ala Val Met Asp Asp Phe Ala Ala Phe Val Glu Lys
1               5                   10


<210> SEQ ID NO 13
<211> LENGTH: 12
<212> TYPE: PRT
<213> ORGANISM: Homo sapiens

<400> SEQUENCE: 13

Ala Val Met Asp Asp Phe Ala Ala Phe Val Glu Lys
1               5                   10


<210> SEQ ID NO 14
<211> LENGTH: 14
<212> TYPE: PRT
<213> ORGANISM: Homo sapiens

<400> SEQUENCE: 14

Lys Val Pro Gln Val Ser Thr Pro Thr Leu Val Glu Val Ser
1               5                   10
```

<210> SEQ ID NO 15
<211> LENGTH: 14
<212> TYPE: PRT
<213> ORGANISM: Homo sapiens

<400> SEQUENCE: 15

Arg Pro Cys Phe Ser Ala Leu Glu Val Asp Glu Thr Tyr Val
1 5 10

<210> SEQ ID NO 16
<211> LENGTH: 14
<212> TYPE: PRT
<213> ORGANISM: Homo sapiens

<400> SEQUENCE: 16

Val Phe Asp Glu Phe Lys Pro Leu Val Glu Glu Pro Gln Asn
1 5 10

<210> SEQ ID NO 17
<211> LENGTH: 4
<212> TYPE: PRT
<213> ORGANISM: Homo sapiens

<400> SEQUENCE: 17

Leu Val Asp Lys
1

<210> SEQ ID NO 18
<211> LENGTH: 4
<212> TYPE: PRT
<213> ORGANISM: Homo sapiens

<400> SEQUENCE: 18

Glu Leu Asp Arg
1

<210> SEQ ID NO 19
<211> LENGTH: 5
<212> TYPE: PRT
<213> ORGANISM: Homo sapiens

<400> SEQUENCE: 19

Val Pro Met Met Lys
1 5

<210> SEQ ID NO 20
<211> LENGTH: 7
<212> TYPE: PRT
<213> ORGANISM: Homo sapiens

<400> SEQUENCE: 20

Ser Pro Leu Phe Met Gly Lys
1 5

<210> SEQ ID NO 21
<211> LENGTH: 8
<212> TYPE: PRT
<213> ORGANISM: Homo sapiens

<400> SEQUENCE: 21

Gln Ile Asn Asp Tyr Val Glu Lys
1 5

<210> SEQ ID NO 22

-continued

```
<211> LENGTH: 14
<212> TYPE: PRT
<213> ORGANISM: Homo sapiens

<400> SEQUENCE: 22

Leu Gln His Leu Glu Asn Glu Leu Thr His Asp Ile Ile Thr
1               5                   10


<210> SEQ ID NO 23
<211> LENGTH: 12
<212> TYPE: PRT
<213> ORGANISM: Homo sapiens

<400> SEQUENCE: 23

His Asp Gln Asp His Pro Thr Phe Asn Lys Ile Thr
1               5                   10
```